(12) United States Patent
Tsegaye

(10) Patent No.: US 11,884,928 B2
(45) Date of Patent: *Jan. 30, 2024

(54) METHODS FOR GENETIC ENGINEERING KLUYVEROMYCES HOST CELLS

(71) Applicant: Amyris, Inc., Emeryville, CA (US)

(72) Inventor: Yoseph Tsegaye, San Jose, CA (US)

(73) Assignee: Amyris, Inc., Emeryville, CA (US)

( * ) Notice: Subject to any disclaimer, the term of this patent is extended or adjusted under 35 U.S.C. 154(b) by 568 days.

This patent is subject to a terminal disclaimer.

(21) Appl. No.: 16/646,013

(22) PCT Filed: Sep. 12, 2018

(86) PCT No.: PCT/US2018/050635
§ 371 (c)(1),
(2) Date: Mar. 10, 2020

(87) PCT Pub. No.: WO2019/055495
PCT Pub. Date: Mar. 21, 2019

(65) Prior Publication Data
US 2020/0263188 A1   Aug. 20, 2020

Related U.S. Application Data

(60) Provisional application No. 62/667,089, filed on May 4, 2018, provisional application No. 62/560,006, filed on Sep. 18, 2017.

(51) Int. Cl.
| C12N 9/22 | (2006.01) |
|---|---|
| C12N 15/62 | (2006.01) |
| C12N 15/113 | (2010.01) |
| C12N 15/81 | (2006.01) |
| C07K 16/28 | (2006.01) |
| C07K 16/32 | (2006.01) |

(52) U.S. Cl.
CPC ........ *C12N 15/815* (2013.01); *C07K 16/2887* (2013.01); *C07K 16/32* (2013.01); *C12N 9/22* (2013.01); *C12N 15/113* (2013.01); *C12N 2310/20* (2017.05); *C12N 2800/80* (2013.01)

(58) Field of Classification Search
CPC ............................ C12N 15/113; C12N 15/815
See application file for complete search history.

(56) References Cited

U.S. PATENT DOCUMENTS

| 8,685,737 B2 | 4/2014 | Serber et al. |
|---|---|---|
| 9,476,065 B2 | 10/2016 | Horwitz et al. |
| 11,390,874 B2 | 7/2022 | Jiang |
| 2020/0263188 A1 | 8/2020 | Tsegaye |
| 2020/0263205 A1 | 8/2020 | Walter |

FOREIGN PATENT DOCUMENTS

| WO | 2012/149470 A1 | 11/2012 |
|---|---|---|
| WO | 2012/176981 A1 | 12/2012 |
| WO | 2015/095804 A1 | 6/2015 |
| WO | 2015/138855 A1 | 9/2015 |

OTHER PUBLICATIONS

U.S. Appl. No. 17/841,429, filed Jun. 15, 2022, for "Methods for Genomic Integration in Pichia and Other Host Cells".
International Search Report and Written Opinion in PCT Application PCT/US2018/050635 dated Jan. 4, 2019; 13 pages.
Horwitz, A.A. et al.; "Efficient Multiplexed Integration of Synergistic Alleles and Metabolic Pathways in Yeasts via CRISPR-Cas"; *Cell Systems*; vol. 1, No. 1; Jul. 1, 2015; pp. 88-96.
Krijger J-J et al.; "A novel, lactase-based selection and straing improvement strategy for recombinant protein expression in Kluyveromyces lactis, art 112"; *Microbial Cell Factories*; vol. 11, No. 1; Aug. 20, 2012; pp. 1-12.
International Search Report and Written Opinion in PCT Application PCT/US2018/050732 dated Nov. 8, 2019; 14 pages.
Chen, X.J. et al.; "A gene-cloning system for Kluyveromyces lactis and isolation of a chromosomal gene required for killer toxin production"; Journal of Basic Microbiology; vol. 28, No. 4; Jan. 1, 1988; pp. 211-220.
Dicarlo, J.E. et al.; "Genome engineering in *Saccharomyces cerevisiae* using CRISPR-Cas systems"; Nucleic Acid Research; vol. 41, No. 7; Mar. 4, 2013; pp. 4336-4343.
Lobs, A-K. et al.; "CRISPR-Cas9-0enabled genetic disruptions for understanding ethanol and ethyl acetate biosynthesis in Kluyveromyces marxianus"; *Biotechnology for Biofuels*; vol. 10, No. 1; Jun. 24, 2017; 14 pages.
Walter, J.M. et al.; "CRISPR-Cas-Assisted Multiplexing (CAM): Simple Same-Day Multi-Locus Engineering in Yeast"; *Journal of Cellular Physiology*; vol. 231, No. 12; Dec. 1, 2016; pp. 2563-2569.
Heus, J.J. et al.; "Chromatin structures of *Kluyveromyces lactis* centromeres in *K. tactis* and *Saccharomyces cerevisiae*"; *Chromosoma*; 1993; vol. 102; pp. 660-667.
Hoshida, H. et al.; "Non-homologous end joining-mediated functional marker selection for DNA cloning in the yeast *Kluyveromyces marxianus*"; *Yeast*; 2014; vol. 31; pp. 29-46.
Iborra, F. et al.; "*Kluyveromyces marxianus* Small DNA Fragments Contain Both Autonomous Replicative and Centromeric Elements that also Function in *Kluyveromyces lactis*"; *Yeast*; 1994; vol. 10; pp. 1621-1629.
Liachko, I. et al.; "An autonomously replicating sequence for use in a wide range of budding yeasts"; *FEMS Yeast Res.*; 2014; vol. 14; pp. 364-367.
Abdel-Banat, B. M.A. et al.; "Random and targeted gene integrations through the control of non-homologous end joining in the yeast *Kluyveromyces marxianus*"; *Yeast*; vol. 27; 2010; pp. 29-39.

(Continued)

*Primary Examiner* — Maryam Monshipouri
(74) *Attorney, Agent, or Firm* — Kilpatrick Townsend and Stockton LLP

(57) ABSTRACT

The invention provides methods for genetically engineering *Kluyveromyces*. The methods can be used to genetically engineer *Kluyveromyces* to produce and secrete full-length antibodies or antibody fragments. The invention also provides methods for production and secretion of antibodies.

5 Claims, 9 Drawing Sheets
Specification includes a Sequence Listing.

(56) References Cited

OTHER PUBLICATIONS

International Search Report and Written Opinion in PCT Application PCT/US2018/050613 dated Jan. 4, 2019; 14 pages.

Gao, S. et al.; "Multiplex gene editing of the Yarrowia lipolytica genome using the CRISPR-Cas9 system"; Journal of Industrial Microbiology and Biotechnology; vol. 43, No. 8; Jun. 27, 2016; pp. 1085-1093.

Goncalves, A.M., et al.; "Pichia pastoris: A Recombinant Microfactory for Antibodies and Human Membrane Proteins"; Journal of Microbiology and Biotechnology; vol. 23, No. 5; May 1, 2013; pp. 587-601.

Naatsaari, L. et al.; "Deletion of the Pichia pastoris KU70 Homologue Facilitates Platform Straing Generation for Gene Expression and Synthetic Biology"; PLOS One; Jul. 29, 2012; 14 pages.

Vogl, T. et al.; "New opportunities by synthetic biology for biopharmaceutical production in Pichia pastoris"; Current Opinion in Biotechnology; vol. 24, No. 6; Dec. 24, 2013; pp. 1094-1101.

Weninger, A. et al.; "Combinatorial optimization of CRISPR/Cas9 expression enables precision genome engineering in the methylotrophic yeast *Pichia pastoris*"; Journal of Biotechnology; vol. 235; Mar. 22, 2016; pp. 139-149.

Arruda, A. et al.; "A constitutive expression sytem for Pichia pastoris based on the PGK1 promoter"; Biotechnol. Lett.; vol. 38; 2016; pp. 509-517.

Cho, et al.; ACS Synthetic Biology; vol. 7; Mar. 15, 2018; pp. 1085-1094.

Chakraborty, S.; Prime-editors (nickases), hRad51-Cas9 nickase fusions and dCas9 have the same problem as conventional CRISPR-Cas9 of plasmid/Cas9 integration after making a double stranded break; retrieved from the internet at https://doi.org/10.31219/osf.io/Jt6pe; Dec. 1, 2019.

Non-Reducing

Reducing

Non-Reducing

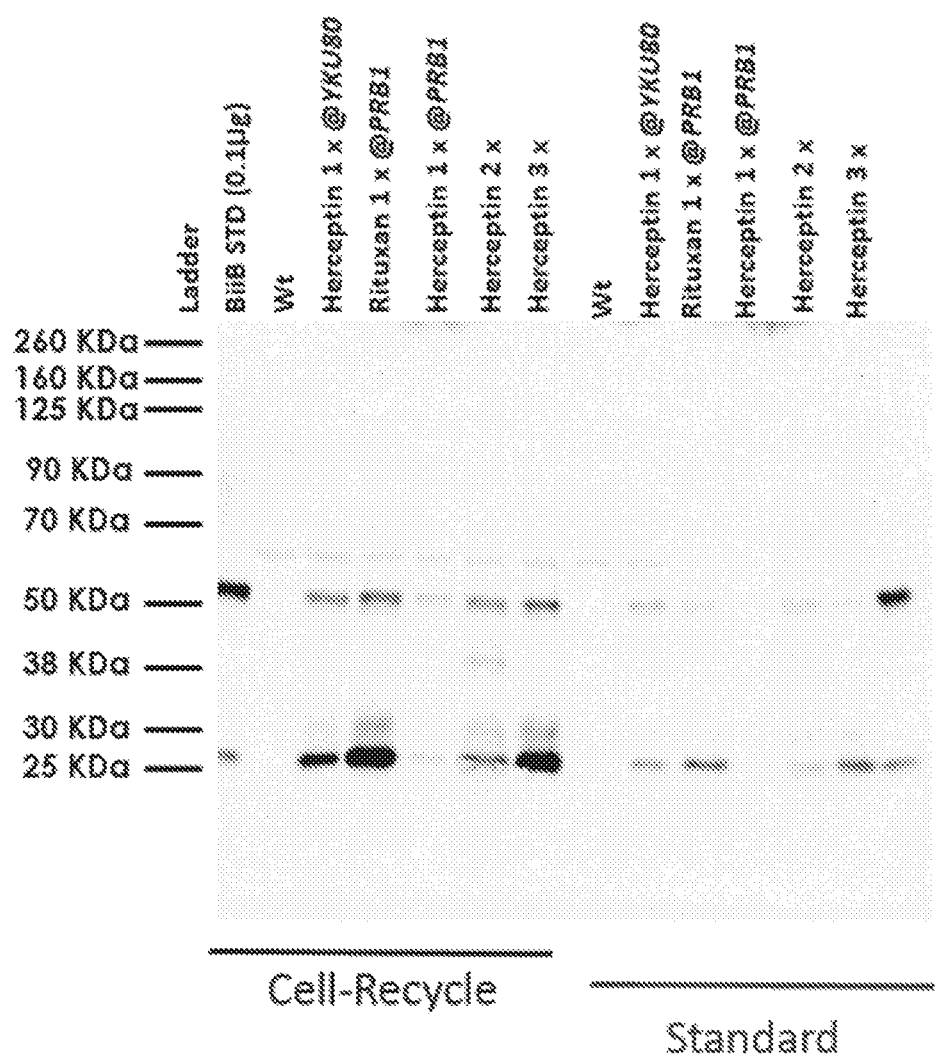

FIG. 3

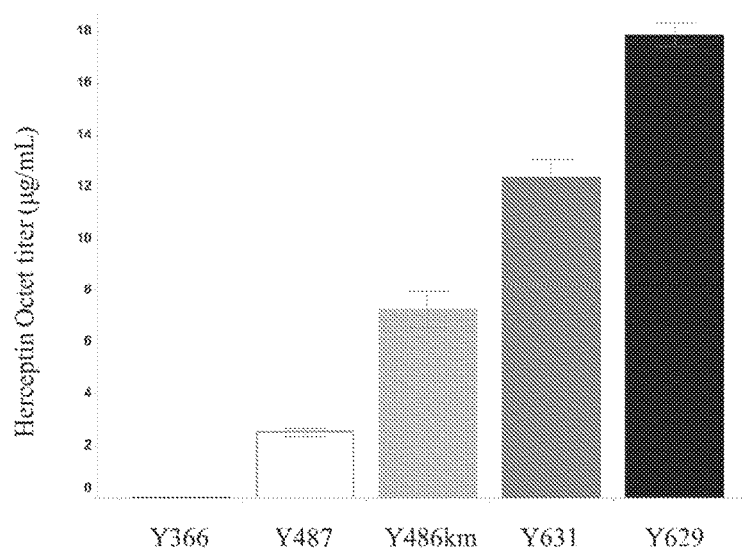

Fig. 10. Antibody titer increases with copy of Herceptin integrated in the *K. marxianus* genome.
Y366, wild type *K. marxianus* strain. Y487 (white bar), one copy of Herceptin integrated at *PRB1* locus.
Y486km (light grey bar), one copy of Herceptin integrated at *yku80* locus. Y631 (dark grey bar), two copies of Herceptin integrated at *YKU80* and *PEP4*. Y629 (black bar), three copies of Herceptin integrated at *YKU80*, *PEP4*, and *PRB1*. Error bars = ±1 standard derivation. N = 8.

Non-Reducing

METHODS FOR GENETIC ENGINEERING *KLUYVEROMYCES* HOST CELLS

CROSS REFERENCES TO RELATED APPLICATIONS

The present application is a US National Phase Application Under 371 of PCT/US2018/050635 filed Sep. 12, 2018, which claims priority to U.S. Provisional Patent Application No. 62/560,006, filed on Sep. 18, 2017 and U.S. Provisional Patent Application No. 62/667,089 filed on May 4, 2018, each of which is incorporated herein by reference in its entirety.

REFERENCE TO SUBMISSION OF A SEQUENCE LISTING AS A TEXT FILE

The instant application contains a Sequence Listing which has been submitted electronically in ASCII format and is hereby incorporated by reference in its entirety. Said ASCII copy, created on Aug. 4, 2023, is named 101928-1180394_000320US_SL.txt and is 45,391 bytes in size.

FIELD OF THE INVENTION

The methods and compositions provided herein generally relate to the fields of molecular biology and genetic engineering.

BACKGROUND

Genetic engineering techniques to introduce targeted modification into a host cell genome find use in a variety of fields. Fundamentally, the determination of how genotype influences phenotype relies on the ability to introduce targeted insertions or deletions to impair or abolish native gene function. In the field of synthetic biology, the fabrication of genetically modified microbes capable of producing compounds or proteins or interest requires the insertion of customized DNA sequences into a chromosome of the host cell; industrial scale production generally requires the introduction of multiple genes in a host cell genome.

For certain host cells, particularly for conventional yeast cells (e.g., *Saccharomyces cerevisiae*), genetic tools are well developed to perform targeted genomic gene deletions and integrations. A variety of non-conventional yeast cells are attractive hosts for industrial applications (e.g., small molecule and protein production). However, the tools for engineering these species are generally poor. For example, the genus *Kluyveromyces*, in particular *K. marxianus*, is an attractive yeast host for the production of industrial products and antibodies due to its fast growth, high acid tolerance and high temperature tolerance. However, making targeted genomic changes to *K. marxianus* has been historically time-consuming due to a high basal rate of non-homologous end joining (NHEJ) and difficulty of maintaining a stable plasmid. CRISPR-based disruption of genes in *K. marxianus* was recently reported for the first time, but no genes were integrated and disruption relied upon NHEJ. Currently, neither meganuclease-mediated, targeted, single genomic integrations nor multiplexed integrations have been reported in *K. marxianus*. Such integrations would dramatically reduce the genetic engineering cycle time by at least 50%.

It would be particularly desirable to use non-conventional yeast cells for the production of antibodies. Currently, monoclonal antibodies for therapeutic purposes are made in Chinese Hamster Ovary (CHO) or other mammalian cell lines. After decades of cell line and process development, productivities of up to 0.5 g/L/day over 12 days have been achieved. The time required from identification of DNA construct to filing of investigational new drug (IND) for small scale production) is about 15 months. See Genentech website. In addition, after decades of improvement, CHO cell line productivity is unlikely to be improved significantly, and demand for monoclonal antibodies is expected to surge as therapies for more widespread and chronic conditions (e.g., Alzheimer's disease) are introduced. Thus, there are two issues with CHO cells—a long timeline for production of a new antibody, and insufficient capacity to supply future needs. To date, full-length monoclonal antibodies with proper glycosylation have been produced by an engineered yeast, *Pichia pastoris* (e.g., Glycofi, purchased by Merck).

To address these problems, currently known methods for genomic modification for various *Kluyveromyces* host cells are in need for improvement. The present invention addresses these and other needs.

SUMMARY

The present invention provides methods for modifying a target site in a *Kluyveromyces* host cell genome. The methods comprise contacting a *Kluyveromyces* host cell, which has a reduced non-homologous end joining (NHEJ) activity with a nucleic acid encoding a nuclease capable of cleaving the target site; and a donor DNA molecule capable of homologous recombination at the cleaved target site, whereby homologous recombination in the host cell results in integration of the donor linear nucleic acid at the target site. A transformed host cell in which the donor DNA molecule is integrated into the target site is then selected.

In some embodiments, the nuclease is an RNA-guided DNA endonuclease and the method further comprises introducing into the cell a guide RNA capable of guiding the RNA-guided endonuclease to the target site. The guide RNA may be on a plasmid comprising stability element derived from *K. marxianus*. The RNA-guided DNA endonuclease may be a Cas9 endonuclease. The nucleic acid encoding the nuclease may be pre-integrated into the genome.

In some embodiments, the step of introducing into the cell a guide RNA may be carried out by contacting the host cell with a linear nucleic acid comprising a nucleic acid sequence encoding the guide RNA or the guide RNA, itself. In these embodiments, the nucleic acid encoding the guide RNA is positioned between a promoter and a terminator, and the guide RNA is transiently expressed from the linear nucleic acid in the host cell. The linear nucleic acid may comprise annealed tracrRNA and crRNA oligonucleotides.

In some embodiments, the methods of the invention further comprise contacting the cell with a linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker. The circular extrachromosomal nucleic acid may further comprise a stability element derived from *K. marxianus*. The stability element may comprise a centromere sequence (CEN) sequence at least 95% identical to SEQ ID NO: 2 and an autonomously replicating sequence (ARS) consensus sequence at least 90% identical to SEQ ID NO: 3. In other embodiments, the stability element is at least 90% identical to a sequence less than 750 bp in length and comprising residues 202 to 876 of SEQ ID NO: 1. In other embodiments, the stability element is at least 95% identical to SEQ ID NO: 1.

The circular extrachromosomal nucleic acid may further comprise a coding sequence for a guide RNA capable of guiding the nuclease to the target site. In these embodiments, the circular extrachromosomal nucleic acid may further comprise a sequence that encodes a crRNA activity and a tracrRNA activity. The crRNA activity and the tracrRNA activity may be expressed as a single contiguous RNA molecule.

In some embodiments of the invention, the nuclease is a meganuclease, for example, F-CphI.

The donor nucleic acid used in the methods of the invention may comprise a nucleic acid sequence encoding a polypeptide. For example, polypeptide may be an antibody light chain, an antibody heavy chain or an antibody light chain linked to an antibody heavy chain. In some embodiments, the methods comprise contacting the host cell with two donor nucleic acids, a first donor nucleic acids encoding an antibody light chain and a second donor nucleic acid encoding an antibody heavy chain. The methods may further comprise recovering the Kluyveromyces host cell which secretes a full-length antibody formed from the antibody heavy chain and the antibody light chain. The recovered host cell may be capable of secreting at least 19 microgram per milliliter of the full-length antibody.

In the methods of the invention, the donor nucleic acid may be codon optimized according to Kluyveromyces preferred codons. The Kluyveromyces host cell may be a K. marxianus host cell.

In some embodiments, the NHEJ is reduced by integrating the nucleic acid encoding the nuclease at YKU70 or YKU80 loci.

The invention further provides Kluyveromyces host cell made by the method of the invention.

The invention further provides methods of producing and secreting an antibody by culturing a Kluyveromyces host cell of the invention in a culture medium containing a carbon source for a first time period, separating the Kluyveromyces host cell from the culture medium; adding a culture medium containing a carbon source to the separated Kluyveromyces host cell and culturing the separated Kluyveromyces host cell in the culture medium for a second time period. In these methods, the antibody may be a full-length antibody. The first time period may be at least 3 days. In some embodiments, the culture medium added is a fresh culture medium which does not contain antibodies.

Even though, CHO cells are the current choice host for production of monoclonal antibodies, the major limitations are it takes a long timeline for production of a new antibody in CHO cells mainly due to long engineering cycle time (about 3 months) and its long doubling time (about 19-24 hours). Kluyveromyces marxianus is an emerging industrial host with potential for a wide variety of applications. K. marxianus may also be the fastest growing eukaryote on the planet, capable of doubling in just 52 minutes (Gombert et al. 2016 and this makes K. marxianus an attractive host for production of monoclonal antibodies due to its fast growth rate and less time it takes to engineer the strain (engineering cycle time of about 2 weeks).

BRIEF DESCRIPTION OF THE DRAWINGS

FIGS. 2A-2C: Western blot analysis of the secretion of Herceptin and Rituxan in K. marxianus strain NRRL-7571 under non-reducing (FIG. 2A), non-reducing with Endo $H_f$ treatment (FIG. 2B) and reducing with Endo $H_f$ treatment (FIG. 2C) conditions using 4% glucose from cane syrup source in a standard (72 hrs. growth) process or cell-recycle process (as described herein).

FIG. 3: Antibody titer increases with copy of Herceptin integrated in the K. marxianus genome. Y366, wild type K. marxianus strain. Y487 (white bar), one copy of Herceptin integrated at PRB1 locus. Y486km (light grey bar), one copy of Herceptin integrated at yku80 locus. Y631 (dark grey bar), two copies of Herceptin integrated at YKU80 and PEP4. Y629 (black bar), three copies of Herceptin integrated at YKU80, PEP4, and PRB1. Error bars=±1 standard derivation. N=8.

DEFINITIONS

Figure 1A:
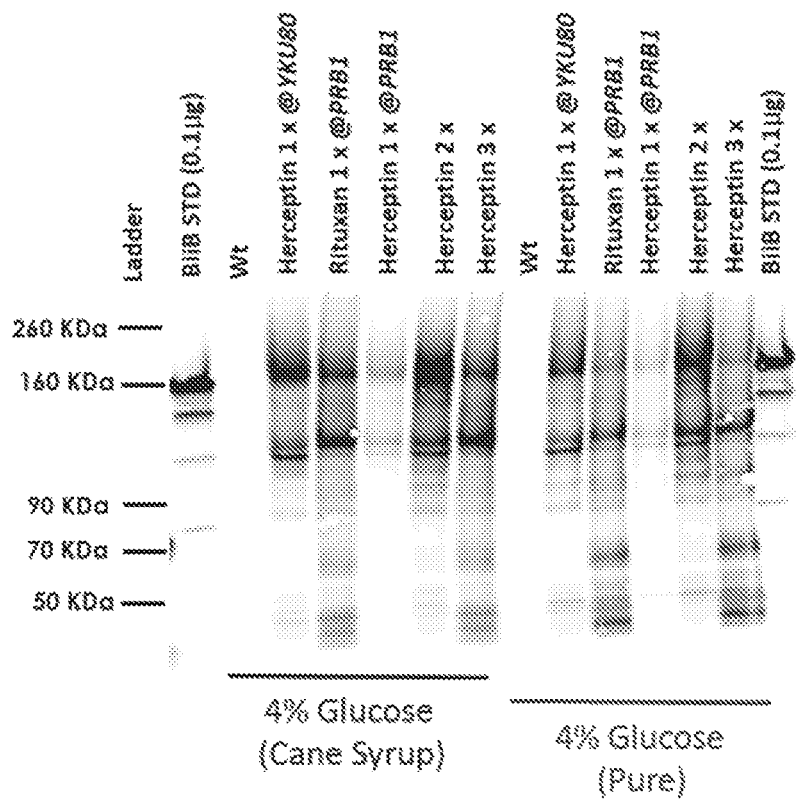
FIGS. 1A and 1B: Western blot analysis of the secretion of Herceptin and Rituxan in K. marxianus strain NRRL-7571 under non-reducing (A) or reducing (B) conditions in 4% glucose either from cane syrup source or when pure glucose is used. Samples in the reducing condition gel were Endo $H_f$ treated before samples were loaded on protein gel.

As used in this specification and the appended claims, the singular forms "a," "an," and "the" include plural reference unless the context clearly dictates otherwise.

The term "nucleic acid" or "nucleotide" refers to deoxyribonucleic acids (DNA) or ribonucleic acids (RNA) and polymers thereof in either single- or double-stranded form. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, guide RNA, or micro RNA A "promoter" is defined as one or more a nucleic acid control sequences that direct transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

As used herein, the term "marker-less" refers to integration of a donor DNA into a target site within a host cell genome without accompanying integration of a selectable marker. In some embodiments, the term also refers to the recovery of such a host cell without utilizing a selection scheme that relies on integration of selectable marker into the host cell genome. For example, in certain embodiments, a selection marker that is episomal or extrachromasomal may be used to select for cells comprising a plasmid comprising a gRNA. Such use is considered marker-less, as long as the selectable marker is not integrated into the host cell genome.

As used herein, the term "operably linked" refers to a functional linkage between nucleic acid sequences such that the sequences encode a desired function. For example, a coding sequence for a gene of interest, e.g., a selectable marker, is in operable linkage with its promoter and/or regulatory sequences when the linked promoter and/or regulatory region functionally controls expression of the coding sequence. It also refers to the linkage between coding sequences such that they may be controlled by the same linked promoter and/or regulatory region; such linkage between coding sequences may also be referred to as being linked in frame or in the same coding frame. "Operably linked" also refers to a linkage of functional but non-coding sequences, such as an autonomous propagation sequence or origin of replication. Such sequences are in operable linkage when they are able to perform their normal function, e.g., enabling the replication, propagation, and/or segregation of a vector bearing the sequence in a host cell.

As used herein, the term "transformation" refers to a genetic alteration of a host cell resulting from the introduction of exogenous genetic material into the host cell.

As used herein, the term "selecting a host cell expressing a selectable marker" also encompasses enriching for host cells expressing a selectable marker from a population of transformed cells.

As used herein, the term "selectable marker" refers to a gene which functions as guidance for selecting a host cell comprising a marker, for example, a marker expressed by a circular, extrachromosomal nucleic acid in the host cell, as described herein. The selectable markers may include, but are not limited to: fluorescent markers, luminescent markers and drug selectable markers, and the like. The fluorescent markers may include, but are not limited to, genes encoding fluorescence proteins such as green fluorescent protein (GFP), cyan fluorescent protein (CFP), yellow fluorescent protein (YFP), red fluorescent protein (dsRFP) and the like. The luminescent markers may include, but are not limited to, genes encoding luminescent proteins such as luciferases. Drug selectable markers suitable for use with the methods and compositions provided herein include, but are not limited to, resistance genes to antibiotics, such as ampicillin, streptomycin, gentamicin, kanamycin, hygromycin, tetracycline, chloramphenicol, and neomycin. In some embodiments, the selection may be positive selection; that is, the cells expressing the marker are isolated from a population, e.g. to create an enriched population of cells comprising the selectable marker. In other instances, the selection may be negative selection; that is, the population is isolated away from the cells, e.g. to create an enriched population of cells that do not comprise the selectable marker. Separation can be by any convenient separation technique appropriate for the selectable marker used. For example, if a fluorescent marker is used, cells can be separated by fluorescence activated cell sorting, whereas if a cell surface marker has been inserted, cells can be separated from the heterogeneous population by affinity separation techniques, e.g. magnetic separation, affinity chromatography, "panning" with an affinity reagent attached to a solid matrix, or other convenient technique.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, the term "complementary" or "complementarity" refers to specific base pairing between nucleotides or nucleic acids. In some embodiments, for example, and not to be limiting, base pairing between a guide RNA (gRNA) and a target site or region in the genome of a host cell is described. Complementary nucleotides are, generally, A and T (or A and U), and G and C. The gRNAs described herein can comprise sequences, for example, a DNA targeting sequence that is perfectly complementary or substantially complementary (e.g., having 1-4 mismatches) to a genomic sequence in a host cell.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-guided DNA endonuclease, Cas9, in complex with a gRNA to recognize and cleave foreign nucleic acid.

As used herein, the terms "cleave," "cleavage" and/or "cleaving" with respect to homing endonuclease, zinc-finger nuclease, TAL-effector nuclease, or an RNA-guided endonuclease, for example, Cas9, refers to the act of creating a break in a particular nucleic acid. The break can leave a blunt end or sticky end (i.e., 5' or 3' overhang), as understood by those of skill in the art. The terms also encompass single strand DNA breaks ("nicks") and double strand DNA breaks.

As used herein, the term "Cas9" refers to an RNA-guided nuclease (e.g., of bacterial or archeal orgin, or derived therefrom). RNA-guided nucleases include the foregoing Cas9 proteins and homologs thereof, and include but are not limited to, Cpf1 (See, e.g., Zetsche et al., Cell, Volume 163, Issue 3, p 759-771, 22 Oct. 2015).

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. Variants of any of the Cas9 nucleases provided herein can be optimized for efficient activity or enhanced stability in the host cell. Thus, engineered Cas9 nucleases, for example, codon optimized Cas9 nucleases for expression in *Kluyveromyces* are also contemplated.

As used herein, the phrases "introducing" or "contacting" in the context of introducing a nucleic acid or protein into a host cell refers to any process that results in the presence of a heterologous nucleic acid or polypeptide inside the host cell. For example, the terms encompass introducing a nucleic acid molecule (e.g., a plasmid or a linear nucleic acid) that encodes the nucleic acid of interest (e.g., an RNA molecule) or polypeptide of interest and results in the transcription of the RNA molecules and translation of the polypeptides. The terms also encompass integrating the nucleic acid encoding the RNA molecules or polypeptides into the genome of a progenitor cell. The nucleic acid is then passed through subsequent generations to the host cell, so that, for example, a nucleic acid encoding an RNA-guided endonuclease is "pre-integrated" into the host cell genome. In some cases, introducing refers to translocation of a nucleic acid or polypeptide from outside the host cell to inside the host cell. Various methods of introducing nucleic acids, polypeptides and other biomolecules into host cells are contemplated, including but not limited to, electroporation, contact with nanowires or nanotubes, spheroplasting, PEG 1000-mediated transformation, biolistics, lithium acetate transformation, lithium chloride transformation, and the like.

As used herein the phrase "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein the term "homologous recombination" refers to a cellular process in which nucleotide sequences are exchanged between two sufficiently identical molecules of DNA. Two DNA molecules have "sufficient" sequence identity if the two sequences have at least 70%, at least 75%>, at least 80%>, at least 85%>, at least 90%>, at least 95%>, at least 99%>, or 100%, identity between recombination regions, over a length of, for example, at least 15 base pairs, at least 20 base pairs, at least 50 base pairs, at least 100 base pairs, at least 250 base pairs, at least 500 base pairs, or more than 500 base pairs. Those of skill in the art readily understand how to determine the identity of two nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, *J. Mol. Biol.* 48: 443 (1970). For a discussion of effective lengths of homology between recombination regions, see Hasty et al. (*Mol. Cell Biol.* 11:5586-91 (1991)).

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term homology directed repair (HDR) refers to a cellular process in which cut or nicked ends of a DNA strand are repaired by polymerization from a homologous template nucleic acid, for example a donor DNA molecule. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid, for example a donor DNA molecule can be introduced to obtain a specific HDR-induced change of the sequence at the target site. In this way, specific sequences can be introduced at the cut site.

As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers a monoclonal antibody (including full-length monoclonal antibodies), human antibodies, chimeric antibodies, nanobodies, diabodies, multispecific antibodies (e.g., bispecific antibodies), and antibody fragments including but not limited to scFv, Fab, and the like so long as they exhibit the desired biological activity.

As used herein, the term "full-length antibody" includes four polypeptides—two light chains and two heavy chains joined by disulfide bonds to form a "Y" shaped molecule. Each heavy chain includes a constant region and a variable region join by a hinge region. The two constant regions of the two heavy chains form an Fc domain. A full-length antibody may be of any isotype (e.g., IgA, IgD, IgE, IgG, and IgM), which is defined by the heavy chain of the antibody.

As used here, the term full-length antibody refers to an antibody having a structure substantially similar to a native antibody structure. A full length antibody includes two identical heavy chain polypeptides, two identical light chain polypeptides, disulfide linkages connecting the two light chain polypeptides, and a glycosylation pattern. Each heavy chain includes a constant region (e.g., CH1, CH2, and CH3) and a variable region (e.g., VH) joined by a hinge region. The two constant regions of the two heavy chains form an Fc domain (e.g., Fc). Each light chain includes a constant region (e.g., CL) and a variable region (e.g, VL). An antigen-binding fragment (Fab) is a region on an antibody that binds to antigens. It is composed of one constant domain and one variable domain of each of the heavy and light chain (e.g., VH, CH1, VL, and CL). A variable fragment (Fv) refers to a fragment containing a variable region of one heavy chain and a variable region of one light chain (e.g., VH and VL). Further, two constant regions of the two heavy chains form the Fc domain of the antibody (e.g., CH2 and CH3 from each of the two heavy chains). A full-length antibody may be of any isotype (e.g., IgA, IgD, IgE, IgG, and IgM), which is defined by the heavy chain of the antibody.

As used herein, the term "stability element" refers to a nucleic acid sequence of between about 200 and about 1300 bp, usually between about 400 and about 900 bp, and often between about 600 and about 750 bp comprising an autonomously replicating sequence (ARS) consensus sequence and, optionally, a centromere sequence (CEN). A stability element allows an extrachromosomal DNA molecule (either linear or circular) comprising the stability element to remain stable in a host cell for extended periods of culturing in non-selective media. The stability elements of the invention typically provide for stability of an extrachromosomal DNA molecule for at least about 10 generations, usually about 20, and often about 30 or more generations in non-selective media.

ARS and CEN sequences have been well studied in yeast. ARSs are origins of DNA replication in yeast chromosomes and are typically short modular DNA sequences comprising an 11-17 bp core sequence element called the ARS Consensus Sequence (ACS), as well as flanking sequences. CEN sequences are part of the complex structures on chromosomes to which spindle fibers attach during meiosis and mitosis. Such sequences are typically between about 100 and about 200 bp long and can be subdivided into three conserved DNA elements CDEI, CDEII and CDEIII. Exemplary CEN sequences of the invention include SEQ ID NOs: 2, 5, 8, 11, 14, 17, 20, and 23. Exemplary ARS consensus sequences of the invention include SEQ ID NOs: 3, 6, 9, 12, 15, 18, 21 and 24.

Exemplary stability elements of the invention include SEQ ID NOs: 1, 4, 7, 10, 13, 16, 19, and 22. Also included are subsequences of these sequence which comprise the ARS consensus sequence, optionally a CEN sequence, and any intervening sequences. Exemplary stability elements of this type include residues 202-876 or residues 537-1252 of SEQ ID NO: 1 and residues 1 to 566 or residues 348-1043 of SEQ ID NO: 4.

One of skill will recognize that the exemplified sequences noted above can be modified and still provide stability for extrachromosomal DNA molecules. For example, CEN sequences, ARS consensus sequences, or stability elements having at least about 90%, 91%, 92% 93%, 94%, 95%, 96%, 97%, 98%, or 99% sequence identity to the exemplified sequences are contemplated by the invention. Those of skill in the art readily understand how to determine the identity of two nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, J. Mol. Biol. 48: 443 (1970).

DETAILED DESCRIPTION OF THE EMBODIMENTS

The present invention provides methods of modifying one or more target sites in a *Kluyveromyces* host cell genome. In some embodiments, the host cell is used for producing and secreting full length antibodies.

Gap Repair

In the methods of the invention, modification of the target sites may comprise methods which use CRISPR/Cas systems and in vivo assembly of marker and/or gRNA vectors via gap repair, as described in WO2015/095804, which is incorporated herein by reference.

In these methods, the *Kluyveromyces* host cell, which has reduced non-homologous end joining (NHEJ) activity, is contacted with a linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and/or a gRNA. The circular extrachromosomal nucleic acid will typically comprise stability element derived from *Kluyveromyces*, particularly as described in more detail below.

The cell also comprises a nuclease capable of cleaving the target sites and a donor molecule. The target sites can be any desired site within the host genome. For example, target sites may be positioned within genes encoding proteases that degrade polypeptide products made by the host cell or genes encoding glycosyltransferases that add undesired carbohydrates to an expressed polypeptide product. By targeting such genes, unwanted protease activity and/or glycosyltransferase activity can be reduced or eliminated.

Donor DNA molecules are flanked by nucleotide sequences that are homologous to genomic sequences flanking the target site. In some embodiments, the donor DNA molecule comprises a homologous sequence at the 5' terminus that is about 70%, 75%, 80%, 85%, 90%, 95% or 100% homologous to a 5' region of a selected genomic target site In some embodiments, the donor DNA molecule comprises a homologous sequence at the 3' terminus that is about 70%, 75%, 80%, 85%, 90%, 95% or 100% homologous to a 3' region of a selected genomic target site. In some cases, each of the homologous sequences flanking the donor DNA molecule comprises from about 50 to about 1500 nucleotides.

The donor DNA molecule may comprise any nucleic acid of interest. For example, the donor DNA molecule may comprise a gene of interest that can be knocked in to a host genome. In other embodiments, the donor DNA molecule functions as a knockout construct that is capable of specifically disrupting a target gene upon integration of the construct into the target site of the host cell genome, thereby rendering the disrupted gene non-functional. Examples of nucleic acids of interest include, but are not limited to, a polypeptide-coding sequence, a promoter, an enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In specific embodiments, the nucleic acid of interest does not comprise a nucleic acid encoding a selectable marker.

In some embodiments the polypeptide is an antibody light chain, an antibody heavy chain, or antibody light chain linked to an antibody heavy chain. In some embodiments, a first donor DNA molecule comprising a first nucleic acid sequence encoding an antibody light chain and a second donor DNA molecule comprising a second nucleic acid sequence encoding an antibody heavy chain can be used. Both donor DNA molecules are capable of homologous recombination at a cleaved target site, whereby homologous recombination in the host cell results in integration of nucleic acid sequences encoding the light and heavy chains at two different target sites. Alternatively, the first and second nucleic acid sequences can be present on a single donor DNA molecule and integrated at a single target site. Transformed cells are identified by the presence of the selectable marker on the circular extrachromosomal nucleic acid.

NHEJ activity in the host cell may be disrupted in a number of ways. Typically, a gene locus that is involved in NHEJ activity of the cell is disrupted. For example, the YKU70 gene locus may be disrupted, such that NHEJ activity is reduced in the cell. In some cases, the YKU70 gene locus is disrupted by inserting or integrating a nucleic acid encoding an RNA-guided endonuclease in the YKU70 gene locus. The reduction in NHEJ activity can be a reduction of at least 20%, 30%, 40%, 50%, 60%, 70%, 80%, 90%, 100% or any percent reduction in between these percentages, as compared to a *Kluyveromyces* cell that does not have a disruption in a gene controlling NHEJ in the cell.

In some embodiments, the RNA-guided DNA endonuclease is provided by introducing a nucleic acid encoding the endonuclease into the host cell. For example, an extra chromosomal nucleic acid (e.g., a plasmid or vector) comprising a stability element of the invention and a nucleic acid encoding the RNA-guided DNA endonuclease can be introduced into the cell. In these embodiments, the linear nucleic acid capable of homologous recombination with itself or with one or more additional linear nucleic acids may comprise the sequence encoding the RNA-guided endonuclease. Homologous recombination results in formation of a circular extrachromosomal nucleic acid comprising the sequence encoding the RNA-guided endonuclease. In some embodiments, the plasmid can further comprise a nucleic acid sequence encoding a selectable marker for maintenance of the plasmid in the host cell. In some embodiments the nucleic acid encoding the endonuclease further comprises a promoter sequence.

In some embodiments, the nucleic acid encoding the RNA-guided DNA endonuclease is integrated into genome of the host cell. In certain embodiments, the RNA-guided DNA endonuclease, for example, Cas9, is integrated into the YKU70 gene of the *Kluyveromyces* host cell, thereby reducing NHEJ activity in the yeast cell. In some embodiments, the nucleic acid encoding the RNA-guided DNA endonuclease is under the control of a constitutive promoter. In some embodiments, the RNA-guided DNA endonuclease can be introduced into the host cell prior to, simultaneously with, or after introduction of the first and second linear nucleic acids. In other embodiments, the RNA-guided DNA endonuclease can be introduced into the host cell prior to, simultaneously with, or after introduction of the first linear nucleic acids, the second linear nucleic acid and the donor DNA molecule.

In some embodiments, the linear nucleic acid capable of homologous recombination with itself or with one or more additional linear nucleic acids comprises two internal homologous sequences that are capable of homologously recombining with each other, whereby homologous recombination of the internal homologous sequences results in formation of the circular extrachromosomal nucleic acid comprising a stability element of the invention and expressing a selectable marker. Once circularized, the extrachromosomal nucleic acid includes a coding sequence for a selectable marker, and suitable regulatory sequences such as a promoter and/or a terminator that enables expression of the marker in the host cell. Providing the selectable marker on a circular, extrachromosomal nucleic acid, allows markerless integration of one or more donor DNA molecules into a host cell genome, while avoiding the integration of extraneous sequences (i.e., a selectable marker) into the genome and any deleterious effects associated with prolonged marker expression.

In some embodiments, the methods of the invention provide for markerless recovery of a transformed host cell comprising a successfully integrated donor nucleic acid. Such a cell occurs within a frequency of about one every 1000, 900, 800, 700, 600, 500, 400, 300, 200 or 100 contacted host cells, or clonal populations thereof, screened. In particular embodiments, markerless recovery of a transformed host cell comprising a successfully integrated donor nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated donor nucleic acid occurs within a frequency of about one every 9, 8, 7, 6, 5, 4, 3, or 2 contacted host cells, or clonal populations thereof, screened.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof. Phenotypic readouts, for example, a predicted gain or loss of function, can also be used as a proxy for effecting the intended genomic modification(s).

In other embodiments, the linear nucleic acid comprising a selectable marker is capable of recombining with a second linear nucleic acid encoding, for example, one or more gRNAs. After introduction of the first and second linear nucleic acids, the first and second linear nucleic acids undergo homologous recombination to form a circular, episomal or extrachromosomal nucleic acid comprising the coding sequence for the selectable marker and the one or more gRNAs.

Subsequent to formation of the extrachromosomal nucleic acid comprising the coding sequence for the selectable marker and the gRNA, the gRNA is transcribed from the extrachromosomal nucleic acid and guides the RNA-guided DNA endonuclease expressed in the host cell to a target site in the genome of the host cell, where the endonuclease creates a break at the target site.

The methods of the invention can be used to integrate a plurality (i.e., two or more) donor DNA molecules into a plurality of target sites of the host cell genome. Thus, the *Kluyveromyces* host cell is contacted with a first linear nucleic acid and two or more second linear nucleic acid molecules, wherein each second linear nucleic acid molecule comprises a nucleic acid encoding a different gRNA which targets a different site in the host cell genome. Each different second linear nucleic acid can recombine with the first linear nucleic acid to form two or more different, circular, extrachromosomal nucleic acids in the host cell. It is understood that the term "first linear nucleic acid" and "second linear nucleic acid" includes multiple copies of the same nucleic acid molecule. For example, the host cell can be contacted with two or more second linear nucleic acid molecules, wherein each second linear nucleic acid molecule comprises a nucleic acid encoding a different gRNA to target two, three, four, five, six, seven or more different sites in the host cell genome. In some embodiments, once the gRNA guides the RNA-guided endonuclease to two or more target sites, the endonuclease creates a break at the two or more target sites and two or more donor DNA molecules are integrated into the host cell genome via homologous recombination.

In some embodiments, the linear nucleic acid comprising a selectable marker is a gapped vector comprising a pair of homologous flanking sequences that recombine with a pair of homologous sequences flanking the gRNA cassette in the second linear nucleic acid to form a larger circular vector where the gap has been repaired by inserting the second linear nucleic acid into the gapped vector. In some embodiments each homologous flanking sequence of the pair of homologous flanking sequences in the first nucleic acid contains a recombination region comprising a nucleotide sequence of sufficient length and sequence identity that allows for homologous recombination with the pair of homologous flanking sequences in the second linear nucleic acid, but not with other regions of the first or second linear nucleic acid participating in the in vivo assembly, nor with any genomic regions of the host cell. For in vivo assembly of marker/gRNA vectors via gap repair and for selection of cells capable of homologous recombination and gap repair, see, for example, Horwitz et al. (Cell Systems 1:88-96 (2015)) and WO2015/095804, both of which are incorporated herein in their entireties by this reference.

In some embodiments, the gRNA is introduced into the cell on circular extrachromosomal nucleic acid (i.e., a plasmid) that is not formed through homologous recombination of linear nucleic acid molecules. In these embodiments, the plasmid comprises a stability element of the invention. These embodiments are used, for example, when integration of a single donor DNA molecule is desired.

Using the methods provided herein, one or more target sites in a host cell genome can be sites for integration of nucleic acid sequences encoding the light and heavy chains of full-length antibodies with surprisingly high efficiency compared to conventional CRISPR/Cas systems. The efficiency of alteration in a population of cells can be at least about 5%, 10%, 15%, 20%, 25%, 30%, 35%, 40%, 45%, 50%, 55%, 60%, 65%, 70%, 75% or 80% or higher, or any percentage in between these percentages.

As used throughout, a guide RNA (gRNA) sequence is a sequence that interacts with an RNA-guided DNA endonuclease and specifically binds to or hybridizes to a target nucleic acid within the genome of a cell, such that the gRNA and the targeted nuclease co-localize to the target nucleic acid in the genome of the cell. Each gRNA includes a DNA targeting sequence of about 10 to 50 nucleotides in length that specifically binds to or hybridizes to a target DNA sequence in the genome. For example, the DNA targeting sequence is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. Each gRNA contains a gRNA scaffold sequence that binds to the RNA-guided DNA endonuclease that does not comprise the DNA targeting sequence. In some embodiments, the gRNA comprises a crRNA sequence and a transactivating crRNA (tracrRNA) sequence. In some embodiments, the gRNA does not comprise a tracrRNA sequence.

Generally, the DNA targeting sequence is designed to complement (e.g., perfectly complement) or substantially complement the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%).

Any RNA-guided DNA endonuclease can be used in the methods provided herein. In some embodiments, the RNA-guided DNA endonuclease is an active Cas9 endonuclease such that when bound to a target nucleic acid as part of a complex with a gRNA, a double strand break is introduced into the target nucleic acid. In some embodiments, the double strand break is repaired by HDR to insert a donor DNA molecule into the genome of the host cell. Various Cas9 endonucleases can be used in the methods described herein. For example, a Cas9 nuclease that requires an NGG protospacer adjacent motif (PAM) immediately 3' of the region targeted by the gRNA can be utilized. As another example, Cas9 proteins with orthogonal PAM motif requirements can be used to target sequences that do not have an adjacent NGG PAM sequence. Exemplary Cas9 proteins with orthogonal PAM sequence specificities include, but are not limited to, those described in Esvelt et al. (Nature Methods 10: 1116-1121 (2013)).

In some cases, the Cas9 protein is a nickase, such that when bound to target nucleic acid as part of a complex with a gRNA, a single strand break or nick is introduced into the target nucleic acid. A pair of Cas9 nickases, each bound to a different gRNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation (See, for example, Ran et al. "Double nicking by RNA-guided CRISPR Cas9 for enhanced genome editing specificity," Cell 154(6): 1380-1389 (2013)).

Introducing Guide RNAs into the Host Cell

In some embodiments, the CRISPR/Cas 9 methods described above are carried out without using in vivo assembly of marker and/or gRNA vectors via gap repair, as described in the previous section. In these methods, all other aspects of the invention are as described above, for example, the host cells, the target sites, the RNA guided nucleases, the donor nucleic acids, the guide RNAs, and the like. In these embodiments, the host cell is contacted with a nucleic acid encoding the guide RNA or a guide RNA itself. The nucleic acid may be, for example, a plasmid comprising stability element derived from *K. marxianus*. A transformed host cell comprising the donor nucleic acid integrated at the target site is then selected. In these embodiments, the donor nucleic acid is not capable of homologous recombination with itself or with a linear nucleic acid contacted with the host cell. Otherwise, the donor molecules are identical to those described above.

The guide RNA construct may be transiently expressed from linear DNA cassettes driven by a RNA polymerase III promoter. The gRNA cassettes and linear donor DNAs (wherein at least one of which comprises a selectable marker coding sequence) are co-transformed into a host cell. As in the embodiments described above, the host cell may express the RNA-guided DNA endonuclease (e.g., Cas9) pre-integrated at a chromosomal locus.

In these embodiments, any method for introducing nucleic acids into a host cell may be used, for example, electroporation methods. In some embodiments, crRNA and tracrRNA RNA oligos (IDT products) are annealed in vitro and co-transformed along with linear donor constructs (at least one marked) into a host cell.

Site-Specific Nucleases

In some embodiments, integration of donor nucleic acids into the target sites comprises methods which use extrachromosomal DNA molecules, which may comprise a stability element of the invention and one or more nucleic acid sequence encoding a nuclease, as described in WO 2012/149470, which is incorporated herein by reference. In these methods, all other aspects of the invention are as described above, for example, the host cells, the target sites, the donor nucleic acids, and the like.

In these methods, the donor DNA molecules are introduced into a *Kluyveromyces* host cell, wherein each donor DNA comprises a first homology region and a second homology region. The first and second homology regions share homology with 5' and 3' regions, respectively, of the genomic target site.

An extrachromosomal DNA comprising a stability element as described below and a nucleic acid sequence encoding site-specific nuclease may also be introduced to the host cell. The nuclease is capable of recognizing and cleaving a unique sequence within the target site. Upon induction of a double-stranded break within the target site by the site-specific nuclease, endogenous homologous recombination machinery integrates the donor DNA at the cleaved target site at a higher frequency as compared to a target site not comprising a double-stranded break. This increased frequency of integration obviates the need to co-integrate a selectable marker in order to select transformants having undergone a recombination event.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof.

The methods of the invention can be used for simultaneous genomic integration of a donor DNA molecules using two or more site-specific nucleases.

As noted above, a double-strand break at a selected target site is induced by site specific endonucleases, for example, site-specific recombinases, transposases, topoisomerases, and zinc finger nucleases, and include modified derivatives, variants, and fragments thereof. The nuclease cleaves the target site at a recognition sequence, that is specifically recognized and/or bound by a double-strand break inducing agent. The length of the recognition site sequence can vary, and includes, for example, sequences that are at least 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

In some embodiments, the recognition sequence is palindromic, that is, the sequence on one strand reads the same in the opposite direction on the complementary strand. In some embodiments, the nick/cleavage site is within the recognition sequence. In other embodiments, the nick/cleavage site is outside of the recognition sequence. In some embodiments, cleavage produces blunt end termini. In other embodiments, cleavage produces single-stranded overhangs, i.e., "sticky ends," which can be either 5' overhangs, or 3' overhangs.

In some embodiments, the recognition sequence within the selected target site can be endogenous or exogenous to the host cell genome. When the recognition site is exogenous to the host cell genome, it may be introduced into the host cell genome by any means known to those of skill in the art. For example, the recognition sequence can be introduced using the gap-repair methods described above. Alternatively, an endogenous recognition site could be recognized and/or bound by a modified or engineered double-strand break inducing agent designed or selected to specifically recognize the endogenous recognition sequence to produce a double-strand break. In some embodiments, the modified double-strand break inducing agent is derived from a native, naturally-occurring double-strand break inducing agent. In other embodiments, the modified double-strand break inducing agent is artificially created or synthesized. Methods for selecting such modified or engineered double-strand break inducing agents are known in the art. For example, amino acid sequence variants of the protein(s) can be prepared by mutations in the DNA. Methods for mutagenesis and nucleotide sequence alterations include, for example, Kunkel, (1985) *Proc Natl Acad Sci* USA 82:488-92; Kunkel, et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff, et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double strand break inducing activity are known and generally measure the overall activity and specificity of the agent on DNA substrates containing recognition sites.

Endonucleases useful in the present invention include homing endonucleases, which like restriction endonucleases, bind and cut at a specific recognition sequence. However the recognition sites for homing endonucleases are typically longer, for example, about 18 bp or more. Homing endonucleases, also known as meganucleases, are well known to those of skill in the art and have been classified into the following families based on conserved sequence motifs: an LAGLIDADG homing endonuclease (SEQ ID NO: 22), an HNH homing endonuclease, a His-Cys box homing endonuclease, a GIY-YIG homing endonuclease, and a cyanobacterial homing endonuclease. Examples of homing endonuclease useful in the present invention include, but are not limited to: H-DreI, I-SeeI, I-SceII, I-SceIII, I-SceIV, I-SceV, I-See VI, ISceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, ICmoeI, I-CpaI, I-CpaII, I-CsmI, I-CvuI, I-CvuAIP, I-DdiI, I-DdiII, I-DirI, I-DmoI, I-HmuI, IHmuII, I-HsNIP, I-LlaI, I-MsoI, I-NaaI, I-NanI, I-NclIP, I-NgrIP, I-NitI, I-NjaI, I-Nsp236IP, IPakI, I-PboIP, I-PcuIP, I-PcuAI, I-PcuVI, I-PgrIP, I-PobIP, I-PorI, I-PorIIP, I-PbpIP, ISpBetaIP, I-SeaI, I-SexIP, I-SneIP, I-SpomI, I-SpomCP, I-SpomIP, I-SpomIIP, I-SquIP, ISsp68031, I-SthPhiJP, I-SthPhiST3P, I-SthPhiSTe3bP, I-TdeIP, I-TevI, I-TevII, I-TevIII, IUarAP, I-UarHGPAIP, I-UarHGPA13P, I-VinIP, I-ZbiIP, PI-MgaI, PI-MtuI, PI-MtuHIP PIMtuHIIP, PI-PfuI, PI-PfuII, PI-PkoI, PI-PkoII, PI-Rma43812IP, PI-SpBetaIP, PI-SeeI, PI-TfuI, PI-TfuII, PI-ThyI, PI-TliI, or PI-TliII, or any variant or derivative thereof.

In some embodiments the nuclease is a TAL-effector DNA binding domain-nuclease fusion protein (TALEN). TAL effectors of plant pathogenic bacteria in the genus *Xanthomonas* play important roles in disease, or trigger defense, by binding host DNA and activating effector-specific host genes. The TAL-effector DNA binding domain may be engineered to bind to a desired target sequence, and fused to a nuclease domain, e.g., from a type II restriction endonuclease, typically a nonspecific cleavage domain from a type II restriction endonuclease such as FokI, HhaI, HindIII, Nod, BbvCI, EcoRI, BglI, and AlwI. Thus, in preferred embodiments, the TALEN comprises a TAL effector domain comprising a plurality of TAL effector repeat sequences that, in combination, bind to a specific nucleotide sequence in the target DNA sequence, such that the TALEN cleaves the target DNA within or adjacent to the specific nucleotide sequence. TALENS useful for the methods provided herein include those described in WO10/079430 and U.S. Patent Application Publication No. 2011/0145940.

In some embodiments the nuclease is a site-specific recombinase. A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. In some embodiments, the recombinase is a serine recombinase or a tyrosine recombinase. In some embodiments, the recombinase is from the Integrase or Resolvase families. In some embodiments, the recombinase is an integrase selected from the group consisting of FLP, Cre, lambda integrase, and R.

In some embodiments the nuclease is a transposase. Transposases are polypeptides that mediate transposition of a transposon from one location in the genome to another. Transposases typically induce double strand breaks to excise the transposon, recognize subterminal repeats, and bring together the ends of the excised transposon, in some systems other proteins are also required to bring together the ends during transposition. Examples of transposons and transposases include, but are not limited to, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta 1 elements from *Arabidopsis* (retrotransposon), the P element transposon from *Drosophila*, the Copia, Mariner and Minos elements from *Drosophila*, the Hermes elements from the housefly, the PiggyBack elements from *Trichplusia ni*, Tc1 elements from *C. elegans*, and IAP elements from mice (retrotransposon).

In some embodiments the nuclease is a zinc-finger nuclease (ZFN). ZFNs are engineered double-strand break inducing agents comprised of a zinc finger DNA binding domain and a double strand break inducing agent domain. Engineered ZFNs consist of two zinc finger arrays (ZFAs), each of which is fused to a single subunit of a non-specific endonuclease, such as the nuclease domain from the FokI enzyme, which becomes active upon dimerization.

Stability Element

In some embodiments, circular extrachromosomal nucleic acids and other plasmids used in the methods of the invention may comprise a stability element derived from *K. marxianus*. The stability elements may comprise an ARS consensus sequence, and optionally a CEN sequence, from SEQ ID NOs: 1, 4, 7, 10, 13, 16, 19, or 22. In some embodiments, the stability elements comprises a CEN sequence at least 95% identical to SEQ ID NO: 2 and an ARS consensus sequence at least 90% identical to SEQ ID NO: 3. In some embodiments the stability element is at least 90% identical to a sequence less than 750 bp in length and comprising residues 202-876 or residues 537-1252 of SEQ ID NO: 1 and residues 1 to 566 or residues 348-1043 of SEQ ID NO: 4. In other embodiments, the stability element is at least 95% identical to SEQ ID NO: 1 or SEQ ID NO: 4.

Host Cells

The methods of the invention can be used to modify one or more target sites in a *Kluyveromyces* host cell genome. The host cell can be any member of the genus *Kluyveromyces*, including, for example, *K. marxianus, K. lactis, K. aestuarii K. africanus, K. bacillisporus K. blattae, K. dobzhanskii, K. hubeiensis, K. lodderae, K. nonfermentans, K. piceae, K. sinensis, K. thermotolerans, K. waltii, K wickerhamii*, and *K. yarrowii*.

Cell Culture

The *Kluyveromyces* host cells are cultured using methods well known to those of skill in the art. If a selectable maker is used, the cells are cultured for a period of time sufficient for expression of the selectable marker from the circularized extrachromosomal vector. In some embodiments where the selectable marker is a drug resistance marker, the culturing is carried out for a period of time sufficient to produce an amount of the marker protein that can support the survival of cells expressing the marker in selectable media. In certain embodiments, these conditions also select against the survival of cells not expressing the selectable marker. Selective pressure can be applied to cells using a variety of compounds or treatments that would be known to one of skill in the art. For example, selective pressure can be applied by exposing host cells to conditions that are suboptimal for or deleterious to growth, progression of the cell cycle or viability, such that cells that are tolerant or resistant to these conditions are selected for compared to cells that are not tolerant or resistant to these conditions. Conditions that can be used to exert or apply selective pressure include, but are not limited to, antibiotics, drugs, mutagens, compounds that slow or halt cell growth or the synthesis of biological building blocks, compounds that disrupt RNA, DNA or protein synthesis, deprivation or limitation of nutrients, amino acids, carbohydrates or compounds required for cell growth and viability from cell growth or culture media, treatments such as growth or maintenance of cells under conditions that are suboptimal for cell growth, for instance at suboptimal temperatures, atmospheric conditions (e.g., % carbon dioxide, oxygen or nitrogen or humidity) or in deprived media conditions. The level of selective pressure that is used can be determined by one of skill in the art. This can be done, for example, by performing a kill curve experiment, where control cells and cells that comprise resistance markers or genes are tested with increasing levels, doses, concentrations or treatments of the selective pressure and the ranges that selected against the negative cells only or preferentially over a desired range of time (e.g., from 1 to 24 hours, 1 to 3 days, 3 to 5 days, 4 to 7 days, 5 to 14 days, 1 to 3 weeks, 2 to 6 weeks). The exact levels, concentrations, doses, or treatments of selective pressure that can be used depends on the cells that are used, the desired properties themselves, the markers, factors or genes that confer resistance or tolerance to the selective pressure as well as the levels of the desired properties that are desired in the cells that are selected and one of skill in the art would readily appreciate how to determine appropriate ranges based on these considerations.

The culturing can be performed in a suitable culture medium in a suitable container, including but not limited to a cell culture plate, a flask, or a fermentor. In some embodiments, the culture medium is an aqueous medium comprising assimilable carbon, nitrogen and phosphate sources. Such a medium can also include appropriate salts, minerals, metals and other nutrients. In some embodiments, in addition to the selection agent, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter). Materials and methods for the maintenance and growth of cell cultures are well known to those skilled in the art of microbiology or fermentation science (see, for example, Bailey et al., Biochemical Engineering Fundamentals, second edition, McGraw Hill, N.Y., 1986). Consideration must be given to appropriate culture medium, pH, temperature, and requirements for aerobic, microaerobic, or anaerobic conditions, depending on the specific requirements of the host cell, the fermentation, and the process. In some embodiments, the culturing is carried out for a period of time sufficient for the transformed population to undergo a plurality of doublings until a desired cell density is reached. In some embodiments, the culturing is carried out for a period of time sufficient for the host cell population to reach a cell density (OD600) of between 0.01 and 400 in the fermentation vessel or container in which the culturing is being carried out. In other embodiments, the culturing is carried for a period of at least 12, 24, 36, 48, 60, 72, 84, 96 or more than 96 hours. In some embodiments, the culturing is carried out for a period of between 3 and 20 days. In some embodiments, the culturing is carried out for a period of 1, 2, 3, 4, 5, 6, 7, 8, 9, 10, 11, 12, 13, 14, 15, 16, 17, 18, 19, 20 or more than 20 days.

In some embodiments of the methods described herein, the methods further comprise the step of eliminating the circularized extrachromosomal vector from the host cell, for example, once a selected host cell has been identified as comprising the desired genomic integration(s). Plasmid-based systems generally require selective pressure on the plasmids to maintain the foreign DNA in the cell. In some embodiments, elimination of a plasmid encoding the selective marker from a selected cell can be achieved by allowing the selected cells to undergo sufficient mitotic divisions such that the plasmid is effectively diluted from the population. Alternatively, plasmid-free cells can be selected by selecting for the absence of the plasmid, e.g., by selecting against a counter-selectable marker (such as, for example, URA3) or by plating identical colonies on both selective media and non-selective media and then selecting a colony that does not grow on the selective media but does grow on the non-selective media.

Methods of Producing a Product of Interest

As noted above, the donor DNA can be used integrate any desired nucleic acid sequence into the genome of the *Kluyveromyces* host cell. Thus, the methods of the invention may comprise culturing a host cell comprising one or more integrated donor DNA molecules of interest encoding one or more proteins of interest under conditions suitable for production of the protein and recovering the protein produced by the host cell. Methods for preparing purified proteins from cell cultures are well known to those of skill in the art. In some embodiments, the protein of interest is a protein selected from the group consisting of an antibody, an enzyme, a hormone, a growth factor, an anticoagulant, blood factors, an engineered protein, an interferon, an interleukin, a thrombolytic, a viral protein or a bacterial protein. For example, the host cells of the invention can be used to produce enzymes capable of hydrolyzing plant carbohydrates, such as cellulases and inulinases.

In some embodiments, one or more secretion signal sequences (e.g., two, three, four, five, six, seven, eight, nine, or ten secretion signal sequences) may be inserted in the donor DNA molecules. The secretion signal sequence encodes a secretion signal peptide that is recognized by the molecular machinery of the host cell, which then secretes the protein from the cell. The choice of a secretion signal peptide may depend on the type of the host cell. For example, a secretion signal sequence may be used in antibody production. In some embodiments, a secretion signal sequence may be placed at the 5' end of the light chain sequence. In some embodiments, a secretion signal sequence may be placed at the 5' end of the heavy chain sequence. In one example, when one donor DNA molecule contains both a light chain sequence and a heavy chain sequence, a secretion signal sequence may be placed at the 5' end of each of the light and heavy chain sequences.

The host cells and methods of the invention can be used to produce high titers of a desired polypeptide. For example, titers can be between about 5 mg/L and about 30 mg/L, usually between about 10 mg/L and about 25 mg/L and often between about 15 mg/L and about 20 mg/L. In certain embodiments, the titers of a desired polypeptide (e.g., full-length antibodies) can be between about 5 mg/L and about 50 g/L, or between about 15 mg/L and about 10 g/L.

In some embodiments, the nucleic acid sequence(s) encoding the polypeptide of interest may be codon optimized according to codon frequencies of the host cell. Using the codon with the highest occurrence frequency in the host cell may reduce unwanted mutations and improve translation efficiency. The donor DNA molecules may also include appropriate expression control elements known in the art, including promoters, enhancers, selection markers, and transcription terminators well known to those of skill in the art. Methods for expressing therapeutic proteins are known in the art. See, for example, Paulina Balbas, Argelia Lorence (eds.) *Recombinant Gene Expression: Reviews and Protocols* (*Methods in Molecular Biology*), Humana Press; 2nd ed. 2004 edition (Jul. 20, 2004); Vladimir Voynov and Justin A. Caravella (eds.) *Therapeutic Proteins: Methods and Protocols* (*Methods in Molecular Biology*) Humana Press; 2nd ed. 2012 edition (Jun. 28, 2012).

The methods and compositions described herein are also useful in introducing multiple modifications in the genome of the host cell and thus provide particular advantages for constructing recombinant organisms comprising optimized biosynthetic pathways, for example, towards the conversion of biomass into biofuels, pharmaceuticals or biomaterials. Functional non-native biological pathways have been successfully constructed in microbial hosts for the production of a number of valuable products, including precursors to the antimalarial drug artemisinin, fatty acid derived fuels and chemicals (e.g., fatty esters, fatty alcohols and waxes), methyl halide derived fuels and chemicals, polyketide synthases that make cholesterol lowering drugs, and polyketides.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Methods for Producing Antibodies

In some embodiments, the Kluyveromyces host cell is a vehicle that includes the necessary cellular components needed to express an antibody from its corresponding nucleic acid sequence(s). As noted above, one or more donor DNA molecules may be used to deliver the nucleic acid sequence(s) into the host cell. In some embodiments, a full length antibody is produced. A first nucleic acid sequence encoding an antibody light chain and a second nucleic acid sequence encoding an antibody heavy chain may each be inserted into single donor DNA molecule. In other embodiments, the first and second nucleic acid sequences encoding the antibody light chain and the antibody heavy chain, respectively, may be inserted into the same donor DNA molecule.

In some embodiments, the nucleic acid sequence(s) encoding the light and heavy chains of the full-length antibody may be codon optimized according to codon frequencies of the host cell, as described above.

When one donor DNA molecule contains both a light chain sequence and a heavy chain sequence, a linker sequence (e.g., a cleavable inker sequence) may be placed between the light chain sequence and the heavy chain sequence. For example, a nucleic acid sequence encoding the full-length antibody may include, in tandem series in this order from the 5' end to the 3' end, the light chain sequence, the linker sequence (e.g., a cleavable linker sequence), and the heavy chain sequence. In another example, the nucleic acid sequence encoding the full-length antibody may include, in tandem series in this order from the 5' end to the 3' end, the heavy chain sequence, the linker sequence (e.g., the cleavable linker sequence), and the light chain sequence. When the light chain sequence and the heavy chain sequence are each inserted in a separate donor DNA molecule, a linker sequence may be placed between the secretion signal sequence in the light or heavy chain sequence. For example, a nucleic acid sequence encoding the light chain may include, in tandem series in this order from the 5' end to the 3' end, the secretion signal sequence, the linker sequence, and the light chain sequence.

In particular embodiments, a linker may be a cleavable linker that contains one or more elements that can be selectively cleaved, e.g., after a protein is formed. In some embodiments, a cleavable linker may be a self-cleavable linker, which may function by making the ribosome skip the synthesis of a peptide bond between a glycine amino acid and a proline amino acid near the C-terminus of the self-cleavable linker. In other embodiments, a linker may be a protease cleavable linker, which contains a protease cleavage site that is specifically recognized by a protease, e.g., a serine protease (e.g., factor Xa, enteropeptidase, proteinase K, chymotrypsin, trypsin, elastase, plasmin, thrombin, acrosomal protease, complement C1, keratinase, collagenase, fibrinolysin, and cocoonase), a cysteine protease (e.g., HRV3C protease, papain, bromelain, cathepsin, calpain, caspase-1, sortase, TEV protease, and hepatitis C virus peptidase 2), a threonine protease, an aspartic protease, a glutamic protease, a metalloprotease, and an asparagine peptide lyase.

In some embodiments, the host cell does not comprise a nucleic acid that encodes the full-length antibody Herceptin (trastuzumab), the full-length antibody Rituxan (rituximab), or the full-length antibody BIIB. In some embodiments, the host cell does not express a full-length antibody Herceptin (trastuzumab), the full-length antibody Rituxan (rituximab), or the full-length antibody BIIB.

The host cells of the invention are capable of secreting a population of antibodies or antibody fragments, wherein at least 40%, 50%, 60%, 70%, 80%, 90%, or 95% the population of antibodies or antibody fragments are full-length antibodies. In some embodiments, these percentages may be determined by weight when comparing the weight of the full-length antibodies to the weight of the population of antibodies or antibody fragments. In some embodiments, these percentages may be determined by densitometry of the Western blot bands.

EXAMPLES

In the present invention, secretion of two full-length antibodies, Herceptin (trastuzumab) and Rituxan (rituximab) in K. marxianus with high titers (≥19 µg/mL) has been achieved. The high titers were achieved using codon-optimization of the amino acid sequences for heavy chain, light chain and secretion tag according to K. marxianus preferred codons. The DNA expression constructs were cloned in as a convergent split cassette at the same locus under strong constitutive native glycolytic promoter. The copy number of the cassette (two/three copies appear to be optimal) was varied. A cell recycle process gave a significant improvement in titer using 4% glucose (from sugar cane source). In addition, a K. marxianus production strain with three copy numbers of Herceptin was run in 0.5 L fermentation tank and gave high titers of full length antibody (estimated titer≥30 µg/mL). The stains were constructed using CRISPR tools and the deletion of NHEJ pathways. Copy number of gene integration and locus specific integrations were controlled by performing targeted genomic integration. The production of these two antibodies was generated in the strain NRRL-7571 background. These results show that K. marxianus is an attractive emerging host for the production and secretion of antibodies.

Materials and Methods

Preparation of K. marxianus Host Strain for CRISPR-Cas

A wild-type K. marxianus strain (NRRL-7571) was used. A S. cerevisiae codon-optimized version of the Streptococcus pyogenes Cas9 gene was fused to an SV40 nuclear localization sequence and cloned into an integration cassette under the expression of the S. cerevisiae TEF1 promoter with a CYC1 terminator (Horwitz 2015, DiCarlo et al 2013a). The construct, marked with an hphA (hygromycin resistance) cassette, was stably integrated at the YKU70 locus of wild-type K. marxianus NRRL-7571 strain. Correct integration at YKU70 locus was verified by colony PCR reactions.

Guide-RNA Expression Cassettes

Cas9 protein is targeted to cut sites by association with a generic structural RNA and a specific targeting RNA. The standard "chimeric" configuration was adopted, in which the targeting and structural RNAs are fused to create a single gRNA. Expression of the gRNA construct was driven by the SNR52 polymerase III promoter, with a SUP4 terminator. The gRNA cassette was cloned into low copy, stable vector using the K. marxianus chromosome V CEN elements by gap repair directly into a Cas9-expressing host strain (Orr-Weaver et al., 1983). In order to gap repair the gRNA cassette/s directly into the expression vector in the host strain, we first generated full-length gRNA cassettes with _500 bp flanking homology to the linearized vector. We co-transformed host cells with single or multiple DNA fragments (for multiplexing) containing gRNA cassettes bearing flanking homology to the linear plasmid. Plasmid and gRNA are supplied in the Sequence Listing and in Table 1. The compositions and methods related to gap repair and other features are described in WO2015/095804, which is incorporated herein by reference. The compositions and methods of markerless genomic integrations are described in WO2012/149470, which is incorporated herein by reference in its entirety. See, also, De Kok et al. (2014) ACS Synth. Biol. 21; 3(2):97-106. doi: 10.1021/sb4001992; Serber et al., U.S. Pat. No. 8,221,982.

Selection of Target Sites and Generation of Donor DNA

Cas9 sites were selected as described previously (Horwitz et al. 2015). Expression constructs for Herceptin and Rituxan were designed as convergent, split expression cassettes using the shorter pre-alpha leader. We codon optimized both monoclonal antibody sequences for *K. marxianus*. Donor DNA constructs with 500 bp of flanking homology were generated using standardized linkers for assembly as described in U.S. Pat. No. 8,110,360, which is hereby incorporated by reference in its entirety. See also, Horwitz, 2017. Full Sequences are provided in the Sequence Listing.

Genomic Integrations of Markerless DNA

In order to integrate antibody constructs into the genome of our host strains using CRISPR, we used the optimized *S. cerevisiae* LiAc methods to co-transform donor DNA and the appropriate gRNA reagents into each Cas9-expressing strain (Gietz and Woods, 2002). Cells were grown overnight in yeast extract peptone dextrose (YPD) media at 30° C. with shaking, then diluted to an optical density (OD) 600 of 0.1 in flasks and grown again at 30° C. with shaking to OD600 of 0.6. Cells were spun down, resuspended in sterile water, spun down, resuspended in 100 mM lithium acetate, spun down, and resuspended in 100 mM lithium acetate (404) per transformation. Transformation was done in PCR plate and the mix included the following: 208 µL 50% PEG 3350, 31 µL 1M lithium acetate, 8.4 µL boiled salmon sperm DNA (10 mg/ml), and 654 DNA and cells. Cells were recovered overnight in nonselective YPD media before plating to selective, nourseothricin-containing media to maintain the gRNA plasmid. Each marker-less integrations were confirmed using a colony PCR.

TABLE 1

CRISPR gRNA sequences

| Target | 19 bp gRNA recognition sequence |
|---|---|
| ΔYKU80 | GCCGCGGGCAACAGCCCGC SEQ ID NO: 19 |
| ΔPRB1 | GATGGTGCCGAGGCGGCGG SEQ ID NO: 20 |
| ΔPEP4 | GCTACAAGCGAGCCCGGCT SEQ ID NO: 21 |

Cultivation of *K. marxianus* mAb Production Strains

Colonies of production strains were picked into 15 mL falcon tubes containing 4 mL of YPD media and grown at 30° C. overnight. 10 µL of culture was inoculated in 25 mL of YPD media containing 4% of glucose (pure or from cane syrup source) and grown for 72 hrs. Cells were spun down and clarified supernatant was analyzed for production of mAbs. In "cell recycle" process, the cell pellet was resuspended with 25 mL of fresh YPD media containing 4% of glucose (pure or from cane syrup source) and grown for another 72 hrs fresh media at 30° C.

Endo H$_f$ Treatment, SDS-PAGE and Western Blot

Endoglycosidases treatment was done using Endo H$_f$ (New England Biolabs, Cat. No. P0703S) according to the manufacturer's instructions. For non-reducing samples, 1x Glycoprotein Denaturing Buffer was replaced with 5% SDS solution. All monoclonal antibody samples were mixed with NuPAGE LDS Sample Buffer (Thermofisher, Cat. No. NP008) and denatured at 70° C. for 10 min before running non-reduced samples on 3-8% Tris-Acetate precast protein gels (Thermofisher, Cat. No. EA0375). For reduced samples, NuPAGe Sample reducing Buffer (Thermofisher, Cat. No. NP009) was used as reducing agent. Reduced samples were run on 4-12% Bis-Tris precast protein gels (Thermofisher, Cat. No. NP0321). For Western blot analysis, Goat anti-human IgG (H+L) (LiCor, Cat. No. 925-32232) was used at a 1:10,000 dilution to detect heavy chain, light chain or full length antibody.

Antibody Titer Measurements

Antibody titer was measured by Octet (ForteBio) or using an ELISA assay. ELISA assay was done using IgG1 Human ELISA Kit (Thermofisher, Cat. No. EHIGG1) according to the manufacturer's instructions.

Results

Secretion of Herceptin and Rituxan

The codon optimized sequences of heavy and light chains of Herceptin (anti-HER2) and Rituxan (anti-CD20) monoclonal antibodies were initially integrated at either YKU80 or PRB1 locus using constructs designed as convergent, split expression cassettes. Both the heavy chains and the light chains (of Herceptin and Rituxan) used the codon optimized shorter pre-alpha leader sequence and gene expression was driven using the native strong glycolytic promoter, pTEF. Strains were constructed as described above (see Materials and Methods) and transformants were selected on nourseothricin. Correct integrations were verified by colony PCR.

Figure 1B:
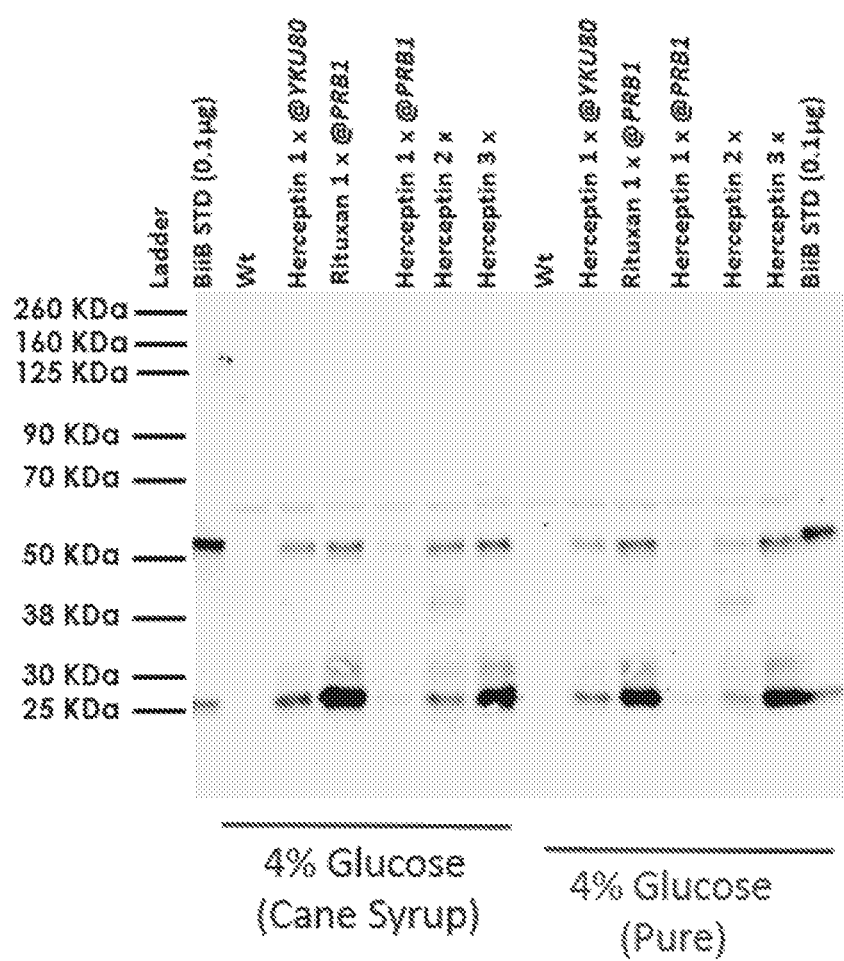

The full length antibody secretion was initially assessed by growing cells in 4% glucose either using a cane syrup source or using pure glucose. Supernatant samples were analyzed using Western blot analysis (FIGS. 1A and 1B). The data indicates the following.

The secretion of two full-length monoclonal antibodies was observed for both Herceptin and Rituxan.

An initial titer measurement using octet shows a strain with three copies of Herceptin (Herceptin 3×) produced 18.9 µg/mL antibody.

Please note all the experiments in FIGS. 1A and 1B were done under cell recycle condition (See Section 3.2.2).

Secretion of Herceptin and Rituxan Under Cell Recycle Versus Standard Conditions A cell recycle process was explored to increase antibody production. The rationale behind considering a cell recycle process is the process may influence the distribution of sugar consumption in production strains by minimizing the sugar flux to biomass and pushing the sugar to antibody production. The cell recycling process may allow maintaining high cell density production under conditions of minimal growth.

In this experiment, a pair of flask cells were grown in YPD media containing 4% of glucose (cane syrup source) and grown for 72 hrs. In a standard process, cells were spun down and clarified supernatant was analyzed for production of mAbs. In cell recycle process, however, the cell pellet was resuspended with another fresh YPD media containing 4% of glucose (cane syrup source) and grown for another 72 hrs at 30° C. Standard and cell-recycle samples were analyzed for antibody production using Western blot analysis and loaded on a same gel side by side.

Figure 2A:
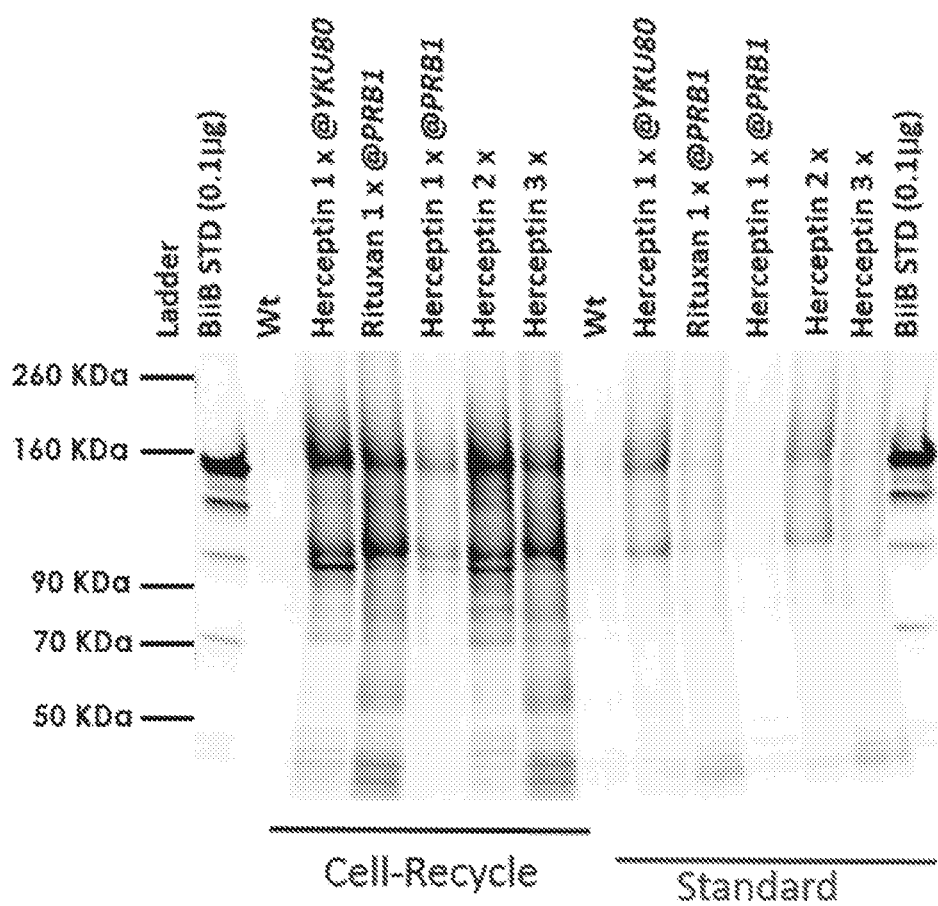
Figure 2B:
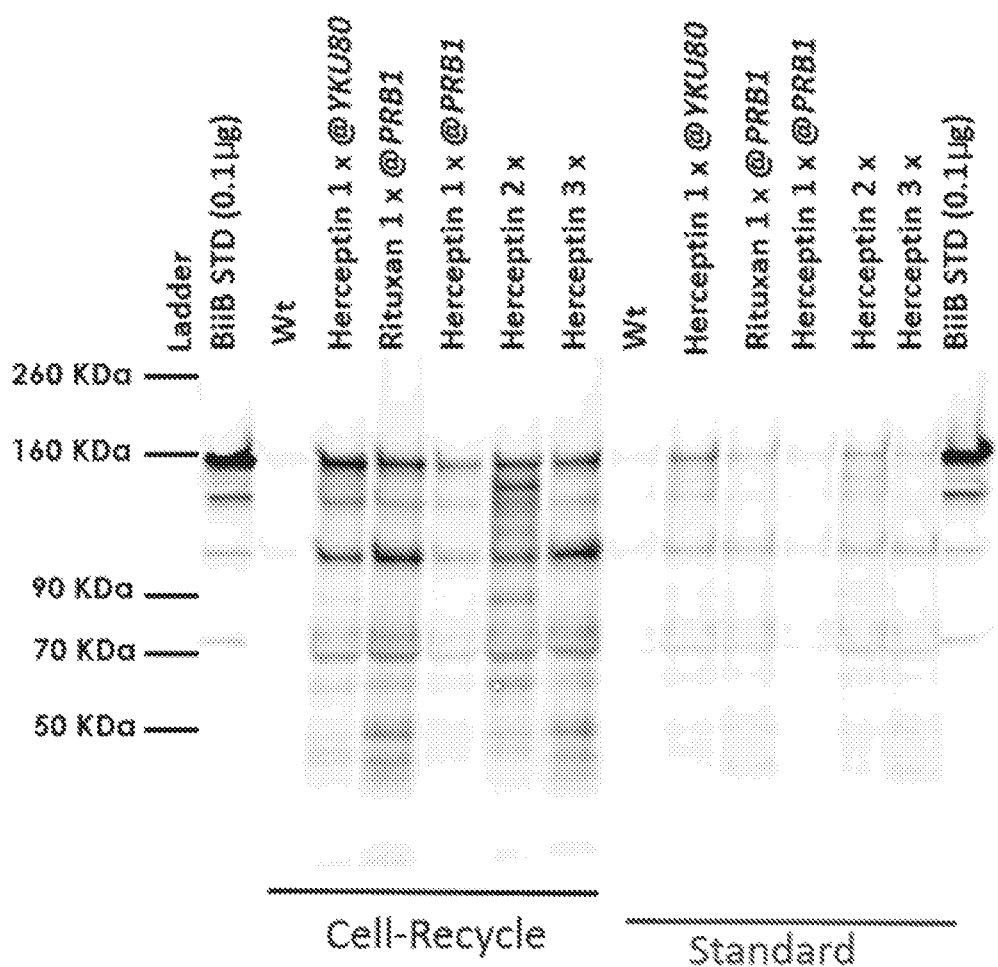

The Western blot result clearly shows that cell recycle process improved titer significantly for all strains tested and is superior over the standard process (FIGS. 2A-2C). In addition, measurement of titer of a three copy Herceptin strain (Herceptin 3×) under cell recycling process gave a titer of 18.9 µg/mL (using cell recycling process and measured by Octet; see FIG. 3). *K. marxianus* secreted both full-length Herceptin and Rittman. Expression or secretion of Herceptin from YKU80 locus gave a better protein production/secretion than expression from PRB1 locus (FIGS. 2A-2C).

Figure 4:
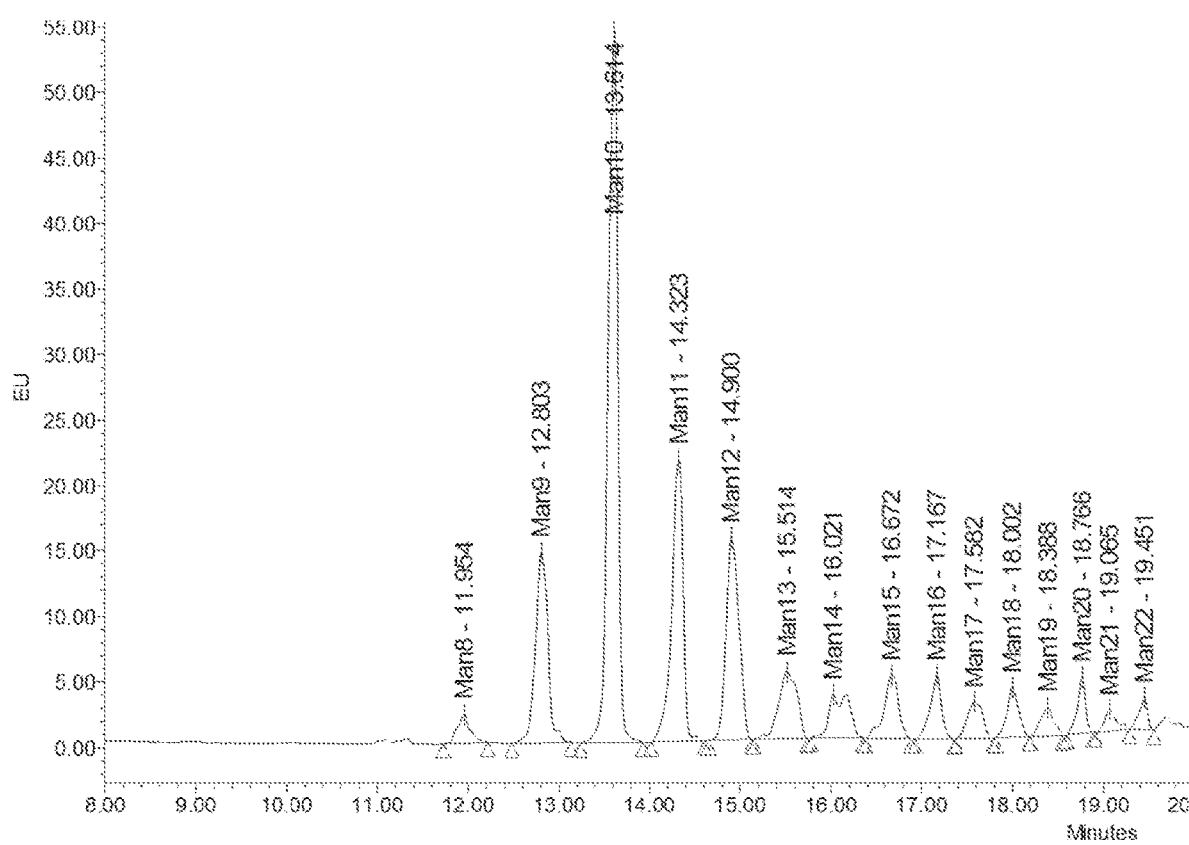
FIG. 4: Mass spectrometry analysis of the glycosylation pattern of the product produced by Herceptin producing strain Y629.

In order to determine the effect of copy number on monoclonal antibody production/secretion, we integrated a second and a third copy of Herceptin at PEP4 locus and PEP4/PRB1 loci respectively. Increasing copy number improved titer significantly and three copies provided the highest titer (FIG. 3). An initial titer measurement using Octet shows a strain with three copies of Herceptin produced a titer of 18.9 µg/mL and Octet measurements (FIG. 3). Treatment of *K. marxianus* secretion samples with Endo $H_f$ gave sharp Western Blot bands (FIGS. 2B and 2C) indicating *K. marxianus* hyperglycosylate secreted proteins and warrants future direction in glyco-engineering. A production supernatant sample, using Herceptin producing strain Y629, was analyzed for N-glycan profile analysis. Mass spectrometer result showed high mannose glycosylation pattern which was expected for *K. marxianus* (FIG. 4).

In a proof of concept experiment, a *K. marxianus* production strain, Y629, with 3 copies of Herceptin was run in a 0.5-liter bioreactor (Sartorius, Germany) with 270 mL fermentation media containing 15 g/L $NH_4H_2PO_4$, 20 g/L total reducing sugar (TRS) from cane syrup (Brotas, Brazil), and a trace metal and vitamin solution. The fermenter was maintained at 30° C. and pH 6.5 with the addition of $NH_4OH$. In an initial batch phase, the fermenter was aerated at 2 volume per volume per minute (VVM) and agitation ramped to maintain 30% dissolved oxygen. After the initial sugar was consumed, the rise in dissolved oxygen triggered pulse-feed mode (10 g/L at a minimum feed rate of 6 g/L) until the culture reaches 150 mmol/L/hr oxygen uptake rate (OUR). Between pulses, there was no delivery of sugar until the dissolved oxygen rises greater than 30% to trigger the next feed pulse. The minimum feed-rate during growth phase was 6 g/L/hr with a programmed increase of 10% of the feed-rate when the time between the end of a pulse and the subsequent $pO_2$ spike is less than 20 minutes. At the end of pulse-feed mode (150 mmol/L/hr OUR), the feeding algorithm was switched to an aerobic constant feed (ACF) with a constant agitation. During ACF, the initial delivery of sugar was at 6 g/L/hr with the controller adjusting the feed-rate to maintain 30% dissolved oxygen.

Figure 5A:
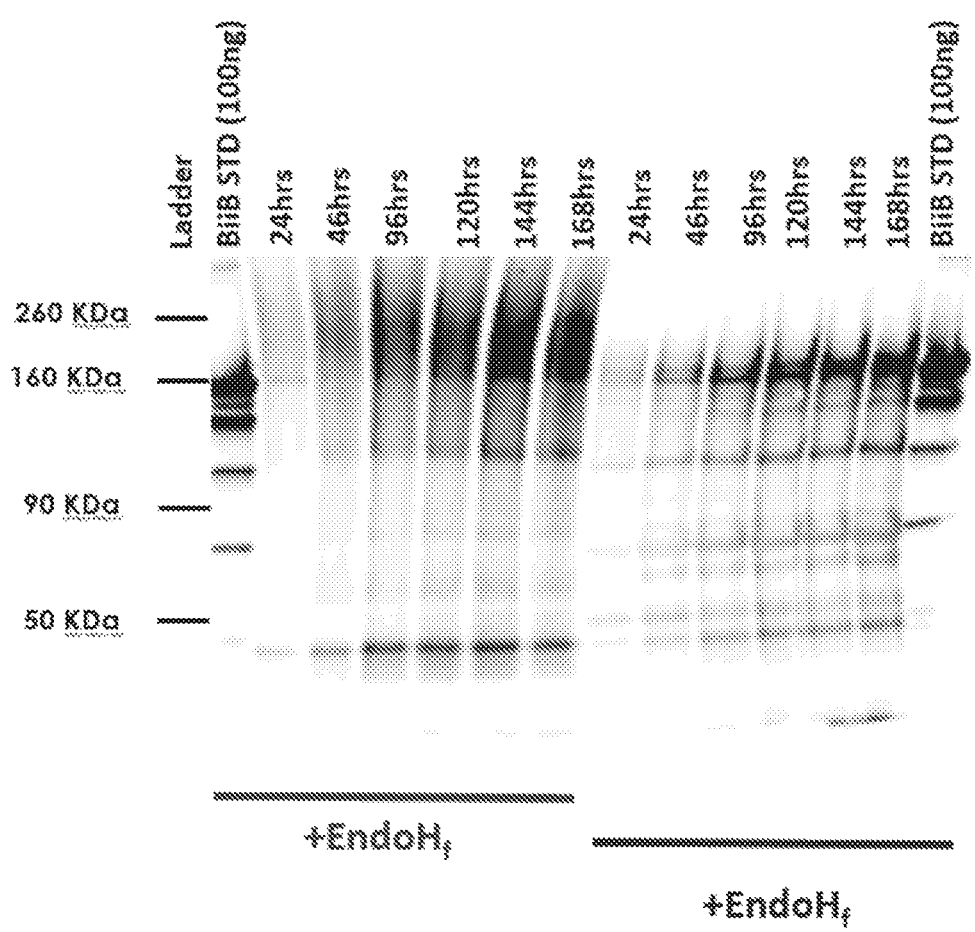
FIGS. 5A and 5B: Measurement of the secretion of Herceptin in a bioreactor using Western blot analysis under non-reducing (FIG. 5A) and reducing (FIG. 5B) conditions. The bioreactor fermentation experiment was run for seven days and samples were withdrawn each day and stored before analysis. All samples were diluted 1:10 before processing in order to avoid overloading of a protein gels. For Endo $H_f$ treated samples, the dilution is 1:20 due to the procedure of EndoH treatment (see materials and methods).
Figure 5B:
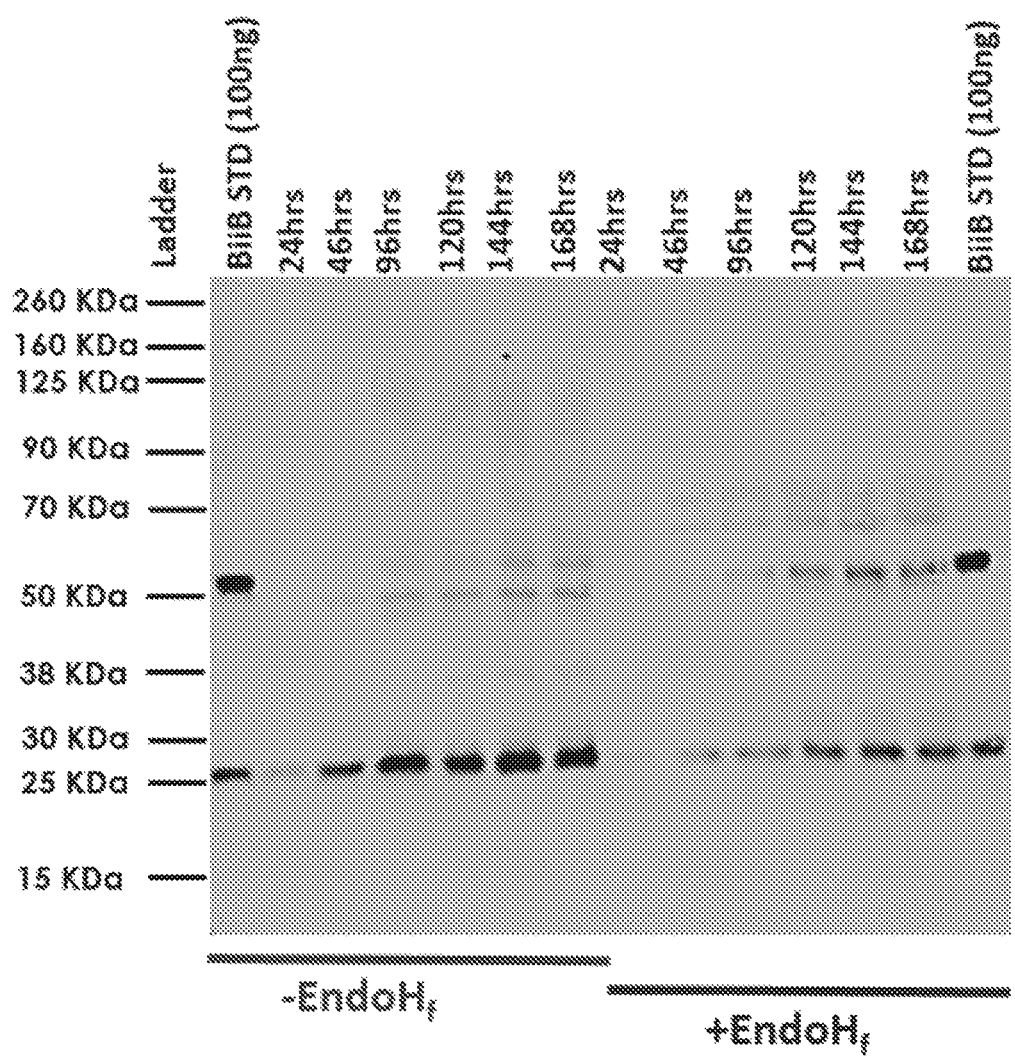

Our fermentation recipe is programmed to reduce the feeding delivery as the dissolved oxygen drops below 30% and subsequently increase feed delivery if dissolved oxygen rises above 30%. The fermentation process continued for seven days and accumulated broth was removed daily and consequently assayed for antibody production. The result shows that titers appear to be significantly improved in bioreactors (FIGS. 5A and 5B) and titer improvement was related to the length of fermentation. Samples from each time point were analyzed using Western Blot analysis and sample dilutions of 1:10 (and a 1:20 dilution for Endo $H_f$ treated samples) was necessary in order to avoid overloading on protein gels (FIGS. 5A-5C).

Measurement of Secretion of Herceptin in a Bioreactor

*K. marxianus* production strains were inoculated in a 0.5-litre fermenter (Sartorius, Germany). We had implemented a fermentation process that continued for seven days and accumulated broth was removed daily and consequently assayed for antibody production. The result shows that titers were significantly improved in bioreactors as compared to flask experiments described above (FIGS. 5A and 5B). Samples from each time point were analyzed by Western blot analysis and a 1:10 dilution of samples (and a 1:20 dilution for Endo $H_f$ treated samples) was necessary in order to avoid overloading on a protein gels.

Additional Experiments on Antibody Production

Table 2 below provides a summary additional experiments for *K. marxianus* (KM) producing BIIB, Herceptin and Rituxan in shake plate. HC/LC, HC and LC sequences are split in two DNA constructs and integrated at the same locus by homology recombination. All BIIB and Herceptin/Rituxan sequences were fused to *S. cerevisiae* pre-pro-alpha and pre-alpha secretion tag, respectively, unless noted. NA, not available. The heavy chain (HC) and light chain (LC) sequences of the BIIB antibody can be found as SEQ ID NO: 18 in PCT publication WO2009043051 (Biogen) as SEQ ID NO: 18 and SEQ ID NO:4, respectively. However, for this construct, the full-length IgG expression was not detected, although antibody fragments were detected.

TABLE 2

| Species | Antibody | Strain | Engineering | Octet Titer (µg/mL) | Full-length antibody secreted |
|---|---|---|---|---|---|
| KM | None | Y366 | yku70 Δ, Prepared for multiplexing | 0 ± 0.00 | No |
| KM | BIIB | Y350 | pep4 Δ ::pTEF > HC/LC, prb1 Δ :: pTEF > HC/LC, mnn4 Δ ::pGAL1 > HC/LC, yku70 Δ | NA | No |
| KM | Herceptin | Y486km | yku80 Δ ::pTEF > HC/LC, yku70 Δ | 7.26 ± 0.71[b] | Yes |
| KM | Herceptin | Y487 | prb1 Δ ::pTEF > HC/LC, yku70 Δ | 2.52 ± 0.16[b] | Yes |
| KM | Herceptin | Y631 | yku80 Δ ::pTEF > HC/LC, pep4 Δ ::pTEF > HC/LC, yku70 Δ | 12.39 ± 0.70[b] | Yes |
| KM | Herceptin | Y629 | yku80 Δ ::pTEF > HC/LC, pep4 Δ ::pTEF > HC LC, prb1 Δ ::pTEF > HC/LC, yku70 Δ | 17.88 ± 0.47[b] | Yes |
| KM | Rituxan | Y543 | prb1 Δ ::pTEF > HC/LC, yku70 Δ | NA | Yes |

[b]Titers were achieved using the cell recycle shake plate model.

One or more features from any embodiments described herein or in the figures may be combined with one or more features of any other embodiment described herein in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Gombert A K, Madeira J V Jr, Cerdán M E and González-Siso M I (2016) *Kluyveromyces marxianus* as a host for heterologous protein synthesis. Appl Microbiol Biotechnol 100:6193-6208.

Lane M M, Burke N, Karreman R, Wolfe K H, O'Byrne C P, Morrissey J P (2011) Physiological and metabolic diversity in the yeast *Kluyveromyces marxianus*. 100(4): 507-19.

Horwitz A A, Walter J M, Schubert M G, Hawkins K, Hernday A D, Mahatdejkul-Meadows T, Szeto W, Chandran S S, Jack D. Newman J D (2015) Efficient Multiplexed Integration of Synergistic Alleles and Metabolic Pathways in Yeasts via CRISPR-Cas. Cell Syst. July 29; 1(1):88-96, 2015.

DiCarlo, J. E., Norville, J. E., Mali, P., Rios, X., Aach, J., and Church, G. M. (2013a). Genome engineering in *Saccharomyces cerevisiae* using CRISPR-Cas systems. Nucleic Acids Res. 41, 4336-4343.

DiCarlo, J. E., Conley, A. J., Penttila, M., Jantti, J., Wang, H. H., and Church, G. M. (2013b). Yeast oligo-mediated genome engineering (YOGE). ACS Synth Biol 2, 741-749.

Orr-Weaver, T. L., Szostak, J. W., and Rothstein, R. J. (1983). Genetic applications of yeast transformation with linear and gapped plasmids. Methods Enzymol. 101, 228-245.

```
Informal Sequence Listing:
Centromeric DNA elements (CDE) are underlined.
Centromere sequence (CEN) is in bold. (SEQ ID NO: 2)
ARS consensus sequence is double underlined. (SEQ ID NO: 3)
```

SEQ ID NO: 1

```
         1         11         21         31         41
         GGATCCGATC TCCTTTCATT TCTGATAAAA GTAAGGCTTC TCTATTTACC

51   TTTTAACCTA CATATTCATA GTTGGAAGTT ATCCTTCTAA GTACGTATAC

101   AATATTAATT CAACGTAAAA ACAAAACTTA CTGTAAATAT GTGTAAAAAA

151   AATCTATTAA ATTCATGGCA GTTTCAAGAA AAGAAAACTA TTATGGTCTG

201   GTCACGTGTA TACAAATTAT TAATTTAAA ACTATATAAT TTATTATTTT

251   TTTATTTTGA AGTTTAGAGT AATTTTAGTA GTATTTTATA TTTTAAATAA

301   ATATGCTTTA AATTTTTACT TAATATTTTA TTATTTTAA ATACAACGTT

351   TTTATTTAAA ACAAAATTAT AAGTTAAAAA GTTGTTCCGA AAGTAAAATA

401   TATTTTATGG GTTTTACAAA AATAAATTAT TTTTAATGTA TTTTTTTAAT

451   TATATTTTTG TATGTAATTA TATCCACAGG TATTATGTTG AATTTAGCTG

501   TTTTAGTTTA CCTGTGTGGT ACTATGATTT TTTTAGAACT CTCCTCTTAG

551   AAATAGGTGG TGTTGCGGTT GACTTTTAAC GATATATCAT TTTCAATTTA

601   TTTATTTTAA AGTGACATAG AGAGATTCCT TTTAATTTTT TAATTTTTAT

651   TTTCAATAAT TTTAAAAATG GGGGACTTTT AAATTGGAAC AAAATGAAAA

701   ATATCTGTTA TACGTGCAAC TGAATTTTAC TGACCTTAAA GGACTATCTC

751   GAACTTGGTT CGGAAATCCT TGAAATGATT GATATTTTGG TGGATTTTCT

801   CTGATTTTCA AACAAGTAGT ATTTTATTTA ATATTTATTA TATTTTTTAC

851   ATTTTTTTAT ATTTTTTATA TGTTTTGGAAG GTAAAGCAAC AATTACTTTC

901   AAAATATATA AATCAAACTG AAATACTTAA TAAGAGACAA ATAACATTCA

951   AGAATCAAAT ACTGGGTTAT TAATCAAAAG ATCTCTCTAC ATGCGCCCAA

1001   ATTCACTATT TAAATTTACT ATACCACTGA CAGAATATAT GAACCCAGAT

1051   TAAGTAGCCA GAGGCTCTTC CACTATATTG AGTATATAGC CTTACATATT
```

```
1101 TTCTGCGCAT AATTTACTGA TGTAAAATAA ACAAAAATAG TTAGTTTGTA

1151 GTTATGAAAA AAGGCTTTTG GAAAATGCGA AATACGTGTT ATTTAAGGTT

1201 AATCAACAAA ACGCATATCC ATAGTGGATA GTTGGATAAA ACTTCAATTG

1251 ATGCGGCCGC
```

Centromeric DNA elements (CDE) are underlined.
Centromere sequence (CEN) is in bold. (SEQ ID NO: 5)
ARS consensus sequence is double underlined. (SEQ ID NO: 6)

SEQ ID NO: 4

```
        1         11         21         31         41
        GATCCAAGTC TGAAGGTTGG TTTGGCACTA ACTTTACTCT TGTTATATTC

51 AGAATTGTAT CAAGTTTATT TGGTAGAGTG GAGCCTTTTT TTATCCGTAA

101 CACTTTTTCC CTGCTCCATT TTGAAAAACG ATTTCAGGCC ATCTTGGCTA

151 TTCCGAATGA ATTTGGAATA TGTTTAAATT AATAAAAATA AATAAAATA

201 AAATAAAATA AAATAAAAAT TAAATCAAAT TAAATTAAAT TAAATTAAAT

251 TAAATTAAAT TAAATAAAAA TAAATACAAC CAATACAACA TGGTAATATT

301 CTTGCATCGT AATGAATATT AAATATCACT TTATTAATCT CATCATG```<u>TTT</u>

351 <u>TATTGTTTT</u>T GTAAGGACTT AATATATTT GAATCAATAT TCTTTCAATT

```
401 ACTAGTACTT TTTTTATATG ACTAAAATTG TTACACATTG GACTGACAGT

451 AATTTTTAAA ATTTATGATT TATTCTTACT TTATATCTTT AAAAGTAGAA

501 ATATTATACG GACGCTTTGA ATACAATTGA CAACTTATCT TACTAGTGTG

551 AATCAACCCT ATCGATGTAG TACTCTTAAA ATACGGCCTT CTTGATAAAG

601 TGTTAAATTC ATTTGGGTAA TGATTTTTCG AAACCCACAT TGAATGAACG

651 ATCTAAATAA ATATAGGATG CAAAAGCATT TTAATAATTC AGAAACAAAC

701 AAATTATTAA ACAGGAGCAG TTGAACGGTA TGTTAGCGAG TTTTGTAAAG

751 GGTGAGTACA TTTATAGCTC TATTGAACAT AATAAATACA TATAAATAGT

801 ATTTTTTGAC CCTCTATGAA GATGGCTTAC CAGCAACTTA TGTCTTTTAA
```

851 TT<u>TCACGTGAC</u> TACTAAACAA AAAAATATGT TATTTAAAAA ATATTTATTT

901 AAATTTTTAA ACTATTATAG ATTATTTGTG AATGCATTAT TTTTTAATTT

951 ATTAATTAAA AGAATTGCTA TTTACTTAAA ATAAGAATAA AAGCTTTTTA

1001 TTTTTTTAAA AGAAAAATAT ATTAAAAACA CTT<u>TTCCGAA AGT</u>TAAAATA

```
1051 ATTTTATATT TATCGGTAGC TGCAATTTAT AGACATAATA TTTTATATTT

1101 TTTAAAATTT ATTATTATTT TGTTTGAAAT AATAACGTCG GTGAGTGTTT

1151 AAGGTGAACT AAGACTGAAA AAGTACATAA TTTTTGTTAA TTTTATGATA

1201 TGATC
```

Centromeric DNA elements (CDE) are underlined.
Centromere sequence (CEN) is in bold. (SEQ ID NO: 8)
ARS consensus sequence is double underlined. (SEQ ID NO: 9)

SEQ ID NO: 7

```
        1         11         21         31         41
        AACAGATTGG TGGGTGGTCA ACGCACAAGC GATATCCCAA CACAGTCGGA

51 AAAACTCTCG TTCATTCCAA AACTGATTGC TTCAGATCAC AACTCCGCTG

101 GAGAAGATGA GTCCGTCACT TTCTTTCAAG ATTTGATTAA CGTTGATCGT

151 TTGAAACGTC TCAGAAATGT CACTGGTATG TCTATCGAAA TCGTGCTTGG
```

```
201 GACGCATAGA GAAATCCCAC AGCAACAGCA GCAGCAGCAG GAGTCACCTG
251 TAGCAGAAGG TGTTCCGGTC GCCCAGGATA ATGGACATGT AACCACGAAC
301 GACAATGCGG CAAATACTTC ATTGGAAGAA CCAAGTTCAC CCATTGACCA
351 GGTTTATGGA TACCTCCTAC AACAGAACAT GTCTACGTTG CCAGAAGTTA
401 CACTTTCGGA AAGTGATATC GCTATGAGCT ACCCGACGGA TCCAGTACCC

451 TCTTACAGCA GCAACTTTAA CAACTTTGCT CTGCCTACTA TTGCCGATGA
501 CAAACAAGAA TTAGAACAGA TGAGATTAAA GGAGCTAGAA AGTGAACCTC
551 CTATCTGAAC ACTTAACGAG AAATATTTAT ATGTGTGTTT TTGTTTGTAT
601 GTATGTATGT ATGTATGCCT GTGTATCATT AAATATATTA GCGGATCCCG
651 GAGTTTTTAT TATCGTGTTC TTTTCATTAT ATAGTGAACC TAAAGTGACT
701 TTCAATTCCA AATTATGGAA AGATTCCTGG CATTATGCCT TATAATAATC
751 ACTTGTTTAC AACATTCCAT TAACAACACA TGTACACTCA AATTCCATTC
801 CATAAAACCA AAAAAAACCT TATTGAATTC TCCAGACCTC TCTGTCGGCT
851 TGACTTTGCT TGCTCAATTC GCGTTTGGCT GAAGATCACT CCAGAACCTA
901 GGACGTCATT ATTGAAATCT GATCACGTGA TTCGCATATT CATATAGACG

951 TATATTTTTC GCCACTTTTC TCTCTTGAAA AAAGTTGTG CTAGATGAAC
1001 TTTGAGAACA AAACACATTG AAAGAAAAGT GGAACATTAT AATAATTGGA
1051 AAGAATAGTA GATTGGGTGG CCAAGTGGAA GAATTTAGTA ACTTTAGTGG
1101 TTAGAGCTTG TTTGAACGAC CAATCCAGTA AACTAATCAA CCATTGAACA
1151 ATGAGTATTC CTATCTTTGG AGATCAAGTT ACCGAAGAGA GAGCAGAAAA
1201 TGCTCGTATG AGTGCCTTTG TTGGTGCCAT CGCCGTTGGT GATCTAGTGA
1251 AAACTACACT AGGTCCAAAA GGTATGGATA AGTTACTTCA AAGTGCATCC
1301 AATAGCTCGA GTTTGGTTAC AAACGATGGT GCTACCATTC TAAAATCTAT
1351 TCCTTTGGAC AACCCTGCTG CCAAGGTGCT TGTTAACATC AGTAAAGTGC
1401 AAGATGATGA AGTTGGTGAC GGTACAACAA GTGTTACTGT TCTAAGTGCA
1451 GAATTATTGA GGGAAGCTGA AAAACTTGTT GAACAAGGCA GAATTCACCC
1501 ACAAACTATC ATCGAGGGTT ACAGAATTGC TTCTGCTGCT GCCCTCTCTG
1551 CATTGGAAAA GGCTGCTGTG GACAACTCCA AGAATAAAGA AGAATTTTAC
1601 AATGATTTGA TCAGCATCGC CAACACAACG CTATCTTCTA AAATTCTATC
1651 TCAAGATAAG GCTCACTTCT CTAAGTTGGC TACCGATGCT ATCTTAAGAT
1701 TAAAGGGCTC TACGAACTTG GAACACATTC AAATTATTAA GATCATTGGT
1751 GGTAAATTAT CGGATTCTTT CCTAGATGAA GGTTTCATTT TGCCAAAGAG
1801 ATTTGGTACC AACCAACCAA AACGTGTTGA AAATGCGAAG ATTTTGATTG
1851 CCAACACTTC TCTAGATACA GACAAGGTTA AAATCTTTGG TACCAAATTT
1901 AAGGTCGACT CTACTTCCAA GTTAGCTGAA CTAGAAAAAG CTGAGCGTGA
1951 AAAAATGAAG AGAAAGATAG AAAAGATTGC ACAATTCAAC ATTAATACCT
2001 TTATCAACAG ACAATTAATC TATGACTACC CTGAACAGAT GTTTACCGAC
2051 ATGGGTATCA ACTCCATCGA ACATGCTGAC TTTGAAGGTG TTGAAAGATT
2101 AGCACTTGTC ACTGGCGGTG AGGTTGTTTC TACATTTGAC AACCCAGAAA
```

```
2151 AATGTAAGCT AGGTGAATGT AAGTTGATCG AAGAAGTTAT AATTGGTGAG

2201 GAAATCTTTA CTAAATTTAC CGGGTGCAAG TCTGGTGAAG CTTGTACCAT

2251 TGTTCTAAGG GGTGCCACTG AGCAAGTCTT GGATGAAGCA GAAAGATCTC

2301 TACATGATGC CCTATCTGTT CTTTCCCAAA CAACAAAGGA GACTAGAACC

2351 GTTCTTGGTG GTGGTTGTGC AGAAATGATA ATGTCTAAAG CAGTTGATAC

2401 TGCAGCTCAA A
```

Centromeric DNA elements (CDE) are underlined.
Centromere sequence (CEN) is in bold. (SEQ ID NO: 11)
ARS consensus sequence is double underlined. (SEQ ID NO: 12)

SEQ ID NO: 10

```
       1         11         21         31         41
     TCAATTACAA AGGGTGGAAA GTGATGGGGG GAATATCATC TGCACAATTT

51 TGGCTCGCTT TATATAGTGC CGAGATTAGT AGGGTCTGGA TAAAAAGCG

101 AAGGAGAATA GGAAGAGGAA GAAATTTTT TTTCTTCCTC TTTGAAAGGC

151 CGGGTAACAA AGTCTCATCG TCCTCCAACC TAGGGCTTTC CTTTCCGCTT

201 TTTTTTTCTT CTTCTCCTCC AAACAAGACC CAACCATACA CACCCACACA

251 GACAGAAGAA AAAGTGTAAG GATGAGCGTT GTGTCGTTTT TTTTTTTTTT

301 TTTTTTTTTT TTGGCGGAGA ATGTGTGCAC GTGCACAGAC ACACACGGGA

351 GCGGCTGTGC CTCCGTATAC GGCAACTGCC ACGACAACCG AGGGCACAGA

401 TACACGAGGT TATGTCAAAG AGGCGTGCTG GCCTGGGGGG GGGAGGCTGC

451 GGATGCCTGA TACTGGGGCC TGATACTGAG CCCCAAGGCT CAGTCTCGGT

501 CTCTGTCTCA AGCTCAAGCC AATTCCTTCC GGGGAACCCA ACCACCTCCG

551 GATTTTTTCC GAAAGTATCC CCGAACGTCT ATGGATTATC CATGTATACA

601 CAGAACAGGG AGTGAGTGAG TGAGTGCGAA AAACGAAAAA AAATACAGTA

651 AAACATAAAC CAGAGATAGC AGGGAAAAGA GCCGTGGTGC GGCGCACTGC

701 GCGCCGCCCT GGGGACGGCG CCTCTCTCTA GTTCCCCCAG AAAAAAGAGT

751 CACGTGTACA CAGCCGCAGC CGCAGCCGCA GCCGCAGTAT CTCCGTGTCA

801 CATAGATTGG ACTGAACTGG ACTAGACTAG ACTAGACTAG AGAGTAGACG

851 AGAATAGACG AGACTAGACG CTCTGGCGTT TCAGATAACA CCAACACTAT

901 CTATGTTATC ATTACACACA CGATACGTAA TACGTTGGGG CTCCAGCGGT

951 CAAGGTTGGG GGTGTGGCCC ACATACGTAA CGTCTCGCCC TACACCATAC

1001 ACGGCATTTT TGTCTGCCTG CCGGCTTTGG CTTGCGCTTT GGTACTTGGT

1051 ATTTTTTCCT CTTTCTTTT GTTTCCACCT TCAACAGACA TCTACGCTTT

1101 TACAGTTCAA GACATTGAAA TTTCAAGACT AGAACTAGAA TTAGAAATTG

1151 GAAATGAAAT TGGAATTATA ATAGATATTA GAAATAGATA GATATTAGAA

1201 TAGAGATAGA TATTCGAGTA ATAGAAAGGA CAAAAGTCAG GAAGAAGAAA

1251 ACTTAGGGCG AGCAAGCTG CCGTATTAAT CTATTGGAAA ACTGAAATAC

1301 TAGGTTTCAG AGAAGAAGAA CAAACAAAAA GCGCAATAAC CAGCACTTTA

1351 TCCAAGTTAC AAGTGTGAGT GAGTGTATAT CTGCAAGCAA GGTGTGATTG

1401 AGTGAGTGAT CCGCTTGTGA TGGATTCTGT CGCTGATAGC ACCCTTGTTT
```

```
1451  CCAAAGCTGT AGCACAGCCT TCGCCGCATC ATGCTGTGAT AAAGCGTGAA

1501  CATGAGCAGG AAAGAGAAAG ACAAATAGAA GCCGAAGCAG AGGCAGAAGC

1551  AGAGGCAGAA GCAGAAGCAG AAACAGAAAT AGA
``` yku70::pTEF1 > Sp.Cas9

SEQ ID NO: 13

```
GACGGCACGGCCACGCGTTTAAACCGCCGTTATAGATGATCTTTATGACTATCACATAAATTTTGTAACCTTTTTC

ATTGGTTCAAAGGTTAAACCATTTGATGACACGACATTCGCAGATATCTTAAGGTGGGGATCAAAAGTTAATGA

CACTAAAAATTGGTTATATTCTCATGGTCCAAATACAAAACCCATAAATGCATCGACTATTAAGTCTAAGGTCAA

AAGGACAAAGGAAATAAATAGAGTGAAATTTCGCTGTCCTTTAATATTAGACGAAAGAGCAGACTTTGTTGTTT

CTGTTAGTGGATACACAATTATATCTCATGAGATTCCTGCATCGAAATACAAGCTTATATATGATAATGGTACGG

TCAAACAAGAAGCGTACTCCCGTCGTAATATCTTGATGCGGAAACTGGAGAAGTGGTACCAAATGACGAACTT

GCAAAAACCTTTTCATTTGGAGATGAAATAATTGAGTTGTCTGAGGAAGAGAACTCACAAATTCAAAACATATA

CGGAAATTATGACTCATTTTTGAAGCTAATAGGATTTAGATCTACCGAGGAATGCTTATGTTTTTACAATAATATC

GACGCTCGTCCAACGCCGGCGGACCTcgaatccttacatcacacccaatcccccacaagtgatccccacacaccatagcttcaaaat gtttctactccttttttactcttccagattttctcggactccgcgcatcgccgtaccacttcaaaacacccaagcacagcatactaaatttcccctctttc ttcctctagggtgtcgttaattacccgtactaaaggtttggaaaagaaaaaagagaccgcctcgtttcttttttcttcgtcgaaaaaggcaataaaaat ttttatcacgtttcttttttcttgaaaattttttttttttgatttttttctctttcgatgacctcccattgatatttaagttaataaacggtcttcaatttct caagtttcagtttcattttctcttgttctattacaacttttttttacttcttgctcattagaaagaaagcatagcaaACCTCCCGCGACCTCCAAAATCGA

ACTACCTTCACAATGGATAAGAAATACTCTATCGGTTTGGATATTGGTACTAACTCCGTTGGTTGGGCCGTTATC

ACTGATGAATACAAGGTTCCATCTAAGAAGTTCAAAGTTTTGGGTAACACTGATAGACACTCTATCAAGAAGAA

CTTGATTGGTGCTTTGTTATTTGACTCTGGTGAAACCGCTGAGGCTACCCGTTTAAAAAGAACTGCTAGACGTAG

ATACACCCGTCGTAAAAACAGAATCTGTTATTTGCAAGAGATCTTCTCCAACGAAATGGCTAAGGTTGACGACTC

TTTTTTCCATAGATTAGAAGAATCTTTCTTAGTTGAAGAAGATAAGAAGCACGAACGTCATCCAATCTTCGGTAA

CATTGTCGACGAAGTTGCTTACCATGAAAAGTACCCAACTATCTATCACTTGAGAAAGAAATTGGTTGATTCTAC

TGACAAAGCCGACTTGAGATTGATCTACTTGGCTTTAGCTCATATGATCAAATTCCGTGGTCATTTTTTAATTGAA

GGTGATTTGAACCCAGACAACTCTGACGTTGATAAATTGTTCATCCAATTGGTTCAAACCTATAACCAATTGTTTG

AAGAAAACCCAATTAACGCTTCTGGTGTTGATGCTAAGGCTATCTTGTCTGCTAGATTGTCTAAATCTAGAAGAT

TGGAAAACTTAATTGCTCAATTGCCAGGTGAAAAAAAAAACGGTTTGTTCGGTAATTTGATTGCTTTATCCTTGG

GTTTGACCCCAAATTTCAAGTCCAACTTTGATTTGGCTGAAGATGCCAAGTTGCAATTGTCTAAGGATACTTACG

ATGATGATTTAGATAACTTATTGGCTCAAATTGGTGATCAATACGCTGATTTGTTTTTAGCTGCCAAGAATTTGTC

CGACGCCATTTTGTTGTCTGACATCTTGAGAGTCAACACTGAAATTACCAAGGCCCCTTTGTCTGCTTCTATGATT

AAGAGATATGACGAACACCACCAAGACTTGACCTTGTTGAAGGCTTTGGTTAGACAACAATTACCTGAAAGTA

TAAGGAAATTTTTTTCGACCAATCTAAGAACGGTTACGCTGGTTACATTGACGGTGGTGCCTCTCAAGAAGAATT

CTACAAATTCATCAAACCAATCTTGGAAAAGATGGACGGTACTGAAGAATTGTTAGTTAAATTGAACAGAGAAG

ACTTGTTGAGAAAACAAAGAACCTTTGACAACGGTTCCATTCCTCACCAAATCCACTTGGGTGAGTTACACGCTA

TTTTGAGAAGACAAGAAGATTTCTACCCATTCTTAAAGGACAACCGTGAAAAGATTGAAAAGATTTTGACCTTCA

GAATTCCATACTACGTCGGTCCTTTGGCTCGTGGTAACTCCAGATTCGCCTGGATGACTAGAAAGTCCGAAGAA

ACTATTACTCCATGGAACTTCGAAGAAGTCGTTGACAAGGGTGCTTCTGCTCAATCCTTTATCGAAAGAATGACC

AACTTCGACAAAAACTTGCCAAACGAAAAAGTCTTGCCAAAGCACTCTTTGTTGTATGAATACTTTACTGTTTATA

ATGAATTGACTAAAGTTAAGTACGTTACTGAAGGTATGAGAAAACCAGCTTTTTTATCTGGTGAACAAAAAAAA
```

```
GCTATCGTCGATTTGTTGTTCAAAACTAACCGTAAAGTTACCGTCAAGCAATTGAAGGAAGATTACTTCAAGAAG

ATTGAATGTTTTGACTCCGTCGAAATCTCCGGTGTTGAAGACAGATTCAATGCTTCTTTGGGTACTTACCACGAC

TTGTTGAAAATTATCAAGGACAAGGATTTCTTAGATAACGAAGAAAACGAAGACATTTTGGAAGATATTGTCTT

GACTTTGACTTTGTTCGAAGATAGAGAAATGATTGAAGAAAGATTGAAGACTTATGCTCATTTGTTCGACGATA

AGGTCATGAAGCAATTAAAGAGAAGACGTTACACTGGTTGGGGTAGATTGTCTAGAAAATTGATTAACGGTATC

CGTGATAAACAATCTGGTAAGACCATCTTGGATTTCTTAAAGTCTGATGGTTTTGCCAACAGAAACTTCATGCAA

TTGATCCACGACGACTCTTTGACTTTCAAGGAGGACATTCAAAAGGCTCAAGTTTCTGGTCAAGGTGACTCTTTG

CATGAACACATTGCCAACTTGGCTGGTTCTCCAGCTATTAAGAAGGGTATCTTGCAAACTGTTAAGGTTGTTGAT

GAATTAGTTAAGGTCATGGGTAGACACAAGCCAGAAAACATCGTCATCGAAATGGCTAGAGAAAACCAAACTA

CTCAAAAGGGTCAAAAGAATTCTAGAGAAAGAATGAAGAGAATTGAGGAAGGTATTAAGGAATTAGGTTCCCA

AATTTTGAAGGAACATCCAGTCGAAAACACTCAATTGCAAAACGAAAAATTGTACTTGTACTACTTACAAAACGG

TAGAGATATGTATGTCGACCAAGAGTTGGACATCAACAGATTGTCCGACTACGATGTTGATCACATCGTTCCACA

ATCCTTCTTAAAGGACGACTCTATCGACAACAAGGTCTTAACCAGATCCGACAAAAACAGAGGTAAGTCTGACA

ACGTTCCATCCGAAGAAGTTGTTAAAAAGATGAAGAACTACTGGAGACAATTGTTGAACGCCAAATTGATCACT

CAAAGAAAGTTCGATAATTTGACCAAGGCTGAAAGAGGTGGTTTGTCTGAATTGGATAAGGCTGGTTTTATTAA

AAGACAATTGGTTGAGACTAGACAAATCACCAAGCATGTCGCTCAAATTTTAGATTCCAGAATGAACACTAAAT

ACGACGAAAACGATAAGTTAATTAGAGAAGTTAAGGTTATTACCTTGAAGTCTAAGTTGGTTCTGATTTCAGAA

AGGACTTCCAATTTTACAAGGTCAGAGAAATTAACAACTACCATCACGCTCATGATGCTTACTTGAACGCCGTTG

TTGGTACCGCTTTGATTAAAAAGTACCCAAAGTTGGAATCCGAATTTGTCTACGGTGACTACAAGGTCTACGATG

TCAGAAAAATGATCGCTAAGTCCGAACAAGAGATTGGTAAGGCTACTGCCAAGTACTTCTTTTACTCTAACATCA

TGAACTTTTTCAAGACTGAAATCACTTTAGCTAACGGTGAAATTCGTAAGAGACCATTGATTGAAACCAACGGTG

AGACTGGTGAAATCGTTTGGGATAAGGGTCGTGATTTCGCTACTGTTAGAAAGGTCTTATCTATGCCACAAGTT

AACATCGTCAAGAAAACCGAAGTTCAAACTGGTGGTTTTTCTAAGGAATCTATCTTGCCAAAAAGAAACTCTGAT

AAATTGATTGCTAGAAAGAAGGATTGGGACCCAAAGAAGTACGGTGGTTTCGATTCCCCAACCGTCGCTTACTC

CGTCTTGGTTGTCGCTAAAGTTGAAAAGGGTAAGTCCAAGAAATTGAAGTCTGTTAAGGAATTGTTGGGTATCA

CTATCATGGAAAGATCTTCCTTCGAAAAGAACCCAATCGATTTTTAGAGGCCAAGGGTTATAAGGAAGTTAAA

AAGGACTTAATTATTAAGTTGCCAAAGTACTCTTTGTTCGAATTAGAAAACGGTAGAAAAAGAATGTTGGCCTCT

GCTGGTGAGTTGCAAAAAGGTAACGAATTGGCCTTGCCATCTAAGTATGTTAACTTTTTGTACTTGGCCTCTCAT

TACGAGAAGTTGAAGGGTTCCCCAGAAGATAACGAACAAAAGCAATTGTTCGTCGAACAACACAAACATTACTT

GGATGAAATTATCGAACAAATCTCCGAGTTTTCCAAACGTGTTATCTTGGCTGACGCCAATTTGGATAAGGTTTT

GTCTGCTTATAATAAGCATAGAGATAAGCCAATTAGAGAACAAGCCGAGAACATCATTCACTTGTTCACTTTGAC

TAATTTAGGTGCTCCAGCTGCCTTCAAATATTTCGACACCACCATTGATAGAAAGAGATACACCTCCACTAAGGA

AGTCTTGGATGCCACCTTGATTCACCAATCTATCACTGGTTTGTACGAAACTAGAATCGATTTGTCTCAATTAGGT

GGTGATTCCCGTGCCGACCCAAAGAAGAAGAGAAAGGTCTAAACAGGCCCCTTTTCCTTTGTCGATATCATGTA

ATTAGTTATGTCACGCTTACATTCACGCCCTCCCCCACATCCGCTCTAACCGAAAAGGAAGGAGTTAGACAACC

TGAAGTCTAGGTCCCTATTTATTTTTTTATAGTTATGTTAGTATTAAGAACGTTATTTATATTTCAAATTTTTCTTTT

TTTTCTGTACAAACGCGTGTACGCATGTAACATTATACTGAAAACCTTGCTTGAGAAGGTTTTGGCATCCCCGCG

TGCTTGGCCGGCCGTTTAATCAGCGCCCAGAGACTAGCACTGAATGATCAACGGGTAGTTCACACGATGCACGA

GCGCAACGCTCACAATGACAGTCTGGACATCAATAGTCACACTACAGAAGGTGATCTCTCAACTTCAGCAGACC

ATAGCGTGTAATAAATGCATAATTATTTTTCTCTAAAAAAAACTCAGCTGAAATTTTATATAAGTACTACATTTTA
```

```
TATACATATTACATACTGAACAATAAGCGCGTTTGACATTTTAATTTTCGAAGACCGCGAATCCTTACATCACACC
CAGTCCCCCAATAGTTCCCCCACACACCATGCTTCAAAAACGCACTGTACTCCTTTTTACTCTTCCGGATTTTCTCG
GACTCTCCGCATCGCCGCACGAGCCAAGCCACACCCACACACCTCATACCATGTTTCCCCTCTTTGACTCTTTCGT
GCGGCTCCATTACCCGCATGAAACTGTATAAAAGTAACAAAAGACTATTTCGTTTCTTTTTCTTTGTCGGAAAAG
GCAAAAAAAAAATTTTTATCACATTTCTTTTTCTTGAAAATTTTTTTGGGATTTTTTCTCTTTCGATGACCTCCCA
TTGATATTTAAGTTAATAAAAGGTCTCCCGTTTTCCAAGTTTTAATTTGTTCCTCTTGTTTAGTCATTCTTCTTCTCA
GCATTGGTCAATTAGAAAGAGAGCATAGCAAACTGATCTAAGTTTTAATTACCATATGAAAAGCCTGAACTCA
CCGCGACGTCTGTCGAGAAGTTTCTGATCGAAAAGTTCGACAGCGTCTCCGACCTGATGCAGCTCTCGGAGGGC
GAAGAATCTCGTGCTTTCAGCTTCGATGTAGGAGGGCGTGGATATGTCCTGCGGGTAAATAGCTGCGCCGATG
GTTTCTACAAAGATCGTTATGTTTATCGGCACTTTGCATCGGCCGCGCTCCCGATTCCGGAAGTGCTTGACATTG
GGGAATTCAGCGAGAGCCTGACCTATTGCATCTCCCGCCGTGCACAGGGTGTCACGTTGCAAGACCTGCCTGAA
ACCGAACTGCCCGCTGTTCTGCAGCCGGTCGCGGAGGCCATGGATGCGATCGCTGCGGCCGATCTTAGCCAGA
CGAGCGGGTTCGGCCCATTCGGACCGCAAGGAATCGGTCAATACACTACATGGCGTGATTTCATATGCGCGATT
GCTGATCCCCATGTGTATCACTGGCAAACTGTGATGGACGACACCGTCAGTGCGTCCGTCGCGCAGGCTCTCGA
TGAGCTGATGCTTTGGGCCGAGGACTGCCCCGAAGTCCGGCACCTCGTGCACGCGGATTTCGGCTCCAACAATG
TCCTGACGGACAATGGCCGCATAACAGCGGTCATTGACTGGAGCGAGGCGATGTTCGGGGATTCCCAATACGA
GGTCGCCAACATCTTCTTCTGGAGGCCGTGGTTGGCTTGTATGGAGCAGCAGACGCGCTACTTCGAGCGGAGG
CATCCGGAGCTTGCAGGATCGCCGCGGCTCCGGGCGTATATGCTCCGCATTGGTCTTGACCAACTCTATCAGAG
CTTGGTTGACGGCAATTTCGATGATGCAGCTTGGGCGCAGGGTCGATGCGACGCAATCGTCCGATCCGGAGCC
GGGACTGTCGGGCGTACACAAATCGCCCGCAGAAGCGCGGCCGTCTGGACCGATGGCTGTGTAGAAGTACTCG
CCGATAGTGGAAACCGACGCCCCAGCACTCGTCCGAGGGCAAAGGAATAGGGAAATTGATAAGACTTTTCTAG
TTGCATATCTTTTATATTTAAATCTTATCTATTAGTTAATTTTTTGTAATTTATCCTTATATAGTCTGGTTATTCTAA
AATATCATTTCAGTATCTAAAATAGTTCTTTTTTTTTTGAGTTAGATTTTTATGGGGGAGAGTTGAAGTGTTGAA
TTTTCCCACTTTGCTTCGGGATTGTGGGTCATTCTGTCGATAACTGATATCACATCATCAATAGAACCTCTTAGAT
GCACGAGCGCAACGCTCACAATTAATCAGCGCCCAGAGACTAGCACTGAATGATCAACGGGTAGTTCACACAG
GTCCGCCGGCGTTGGACGAGCGCTATCGTATACCATTTATAGATGAAGTCAGGAAACTACCTACTTTATCGAGCT
ATCCAGAACTACTAGAAAGTGATGATTATCAAGTACTCAGTAGAGTCACTGAAACGCTCGTGAATTTTTTCAATT
TGAAAAATGGGTACAAGCCTTCTGATTACCACAGCCCAGCGCTTCAAAGACACTTCACGGTACTCAGAGAGTAT
CTTCTCCAGATTGAAAGTAAGGAAACTAAAGATCAAGATGAAGATGACGAAACTCTTCTGAAAGTCAAACAGAT
TCACGAAAGAATTGCTGCTTCTGCTCAATCAGATGATCCTAAACAGCAAAGACTAGTAAAGTATTTGAAACTATG
GAATTCATATTACAATCGCTATAATAATTTGGAAATTGAATCAAAACCAAAACAGAATAAACGGAGTAAATTTAA
TATATAATATATAATAATATTCTATCGGCGGTTTAAACGCGTGGCCGTGCCGTC
``` gRNA Plasmid

SEQ ID NO: 14

```
TCGCGCGTTTCGGTGATGACGGTGAAAACCTCTGACACATGCAGCTCCCGGAGACGGTCACAGCTTGTCTGTAA
GCGGATGCCGGGAGCAGACAAGCCCGTCAGGGCGCGTCAGCGGGTGTTGGCGGGTGTCGGGGCTGGCTTAAC
TATGCGGCATCAGAGCAGATTGTACTGAGAGTGCAAATACACATCATCGTCCTACAAGTTCATCAAAGTGTTGG
ACAGACAACTATACCAGCATGGATCTCTTGTATCGGTTCTTTTCTCCCGCTCTCTCGCAATAACAATGAACACTGG
GTCAATCATAGCCTACACAGGTGAACAGAGTAGCGTTTATACAGGGTTTATACGGTGATTCCTACGGCAAAAT
TTTTCATTTCTAAAAAAAAAAAGAAAAATTTTTCTTTCCAACGCTAGAAGGAAAAGAAAAATCTAATTAAATTGA
```

-continued

```
TTTGGTGATTTTCTGAGAGTTCCCTTTTTCATATATCGAATTTTGAATATAAAAGGAGATCGAAAAAATTTTTCTA
TTCAATCTGTTTTCTGGTTTTATTTGATAGTTTTTTTGTGTATTATTATTATGGATTAGTACTGGTTTATATGGGTTT
TTCTGTATAACTTCTTTTTATTTTAGTTTGTTTAATCTTATTTTGAGTTACATTATAGTTCCCTAACTGCAAGAGAA
GTAACATTAAAAATGACCACTCTTGACGACACGGCTTACCGGTACCGCACCAGTGTCCCGGGGGACGCCGAGG
CCATCGAGGCACTGGATGGGTCCTTCACCACCGACACCGTCTTCCGCGTCACCGCCACCGGGGACGGCTTCACC
CTGCGGGAGGTGCCGGTGGACCCGCCCCTGACCAAGGTGTTCCCCGACGACGAATCGGACGACGAATCGGACG
CCGGGGAGGACGGCGACCCGGACTCCCGGACGTTCGTCGCGTACGGGACGACGGCGACCTGGCGGGCTTCG
TGGTCGTCTCGTACTCCGGCTGGAACCGCCGGCTGACCGTCGAGGACATCGAGGTCGCCCCGGAGCACCGGGG
GCACGGGGTCGGGCGCGTTGATGGGGCTCGCGACGGAGTTCGCCCGCGAGCGGGGCGCCGGGCACCTCTG
GCTGGAGGTCACCAACGTCAACGCACCGGCGATCCACGCGTACCGGCGGATGGGGTTCACCCTCTGCGCGCCTG
GACACCGCCCTGTACGACGGCACCGCCTCGGACGGCGAGCAGGCGCTCTACATGAGCATGCCCTGCCCCTGAG
TTTAACTTGATACTACTAGATTTTTTCTCTTCATTTATAAAATTTTTGGTTATAATTGAAGCTTTAGAAGTATGAAA
AAATCCTTTTTTTTCATTCTTTGCAACCAAAATAAGAAGCTTCTTTTATTCATTGAAATGATGAATATAAACCTAAC
AAAAGAAAAGACTCGAATATCAAACATTAAAAAAAAATAAAAGAGGTTATCTGTTTTCCCATTTAGTTGGAGTT
TGCATTTTCTAATAGATAGAACTCTCAATTAATGTGGATTTAGTTTCTCTGTTCGTTTTTTTTGTTTTGTTCTCACT
GTATTTACATTTCTATTTAGTATTTAGTTATTCATATAATCTTAACTTGCGGTGTGAAATACCGCACAGATGCGTA
AGGAGAAAATACCGCATCAGGAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGAATAGACCGAGATAGGGTTG
AGTGTTGTTCCAGTTTGGAACAAGAGTCCACTATTAAAGAACGTGGACTCCAACGTCAAAGGGCGAAAAACCGT
CTATCAGGGCGATGGCCCACTACGTGAACCATCACCCTAATCAAGTTTTTTGGGGTCGAGGTGCCGTAAAGCAC
TAAATCGGAACCCTAAAGGGAGCCCCCGATTTAGAGCTTGACGGGGAAAGCCTCTTTGAAAAGATAATGTATG
ATTATGCTTTCACTCATATTTATACAGAAACTTGATGTTTTCTTTCGAGTATATACAAGGTGATTACATGTACGTTT
GAAGTACAACTCTAGATTTTGTAGTGCCCTCTTGGGCTAGCGGTAAAGGTGCGCATTTTTTCACACCCTACAATG
TTCTGTTCAAAAGATTTTGGTCAAACGCTGTAGAAGTGAAAGTTGGTGCGCATGTTTCGGCGTTCGAAACTTCTC
CGCAGTGAAAGATAAATGATCGCAGTTCCCTTGGCGTACTCGTTTTAGAGCTAGAAATAGCAAGTTAAAATAAG
GCTAGTCCGTTATCAACTTGAAAAAGTGGCACCGAGTCGGTGGTGCTTTTTTGTTTTTATGTCTCAGCTTTTGT
TCCCTTTAGTGAGGGTTAATTGCGCGCTTGGCGTAATCATGGTCATAGCTGTTTCCTGTGTGAAATTGTTATCCG
CTCACAATTCCACACAACATAGGAGCCGGAAGCATAAAGTGTAAAGCCTGGGGTGCCTAATGAGTGAGGTAAC
TCACATTAATTGCGTTGCGCTCACTGCCCGCTTTCCAGTCGGGAAACCTGTCGTGCCAGGGATCCGATCTCCTTT
CATTTCTGATAAAAGTAAGGCTTCTCTATTTACCTTTTAACCTACATATTCATAGTTGGAAGTTATCCTTCTAAGTA
CGTATACAATATTAATTCAACGTAAAAACAAAACTTACTGTAAATATGTGTAAAAAAATCTATTAAATTCATGG
CAGTTTCAAGAAAAGAAAACTATTATGGTCTGGTCACGTGTATACAAATTATTAATTTTAAAACTATATAATTTAT
TATTTTTTATTTTGAAGTTTAGAGTAATTTTAGTAGTATTTTATATTTTAAATAAATATGCTTTAAATTTTTACTTA
ATATTTTATTATTTTTAAATACAACGTTTTTATTTAAAACAAAATTATAAGTTAAAAAGTTGTTCCGAAAGTAAAA
TATATTTTATGGGTTTTACAAAAATAAATTATTTTTAATGTATTTTTTAATTATATTTTTGTATGTAATTATATCCA
CAGGTATTATGTTGAATTTAGCTGTTTTAGTTTACCTGTGTGGTACTATGATTTTTTTAGAACTCTCCTCTTAGAAA
TAGGTGGTGTTGCGGTTGACTTTTAACGATATATCATTTTCAATTTATTTATTTTAAAGTGACATAGAGAGATTCC
TTTTAATTTTTTAATTTTTATTTTCAATAATTTTAAAAATGGGGACTTTTAAATTGGAACAAAATGAAAAATATCT
GTTATACGTGCAACTGAATTTTACTGACCTTAAAGGACTATCTCGAACTTGGTTCGGAAATCCTTGAAATGATTG
ATATTTTGGTGGATTTTCTCTGATTTTCAAACAAGTAGTATTTTATTTAATATTTATTATATTTTTTACATTTTTTTAT
```

-continued

```
ATTTTTTTATTGTTTGGAAGGTAAAGCAACAATTACTTTCAAAATATATAAATCAAACTGAAATACTTAATAAGAG
ACAAATAACATTCAAGAATCAAATACTGGGTTATTAATCAAAAGATCTCTCTACATGCGCCCAAATTCACTATTTA
AATTTACTATACCACTGACAGAATATATGAACCCAGATTAAGTAGCCAGAGGCTCTTCCACTATATTGAGTATAT
AGCCTTACATATTTTCTGCGCATAATTTACTGATGTAAAATAAACAAAAATAGTTAGTTTGTAGTTATGAAAAAA
GGCTTTTGGAAAATGCGAAATACGTGTTATTTAAGGTTAATCAACAAAACGCATATCCATAGTGGATAGTTGGA
TAAAACTTCAATTGATGCGGCCGCCTGCATTAATGAATCGGCCAACGCGCGGGAGAGGCGGTTTGCGTATTG
GGCGCTCTTCCGCTTCCTCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAAAGGCCAGC
AAAAGGCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTACAGAGTTC
TTGAAGTGGTGGCCTAACTACGGCTACACTAGAAGGACAGTATTTGGTATCTGCGCTCTGCTGAAGCCAGTTAC
CTTCGGAAAAAGAGTTGGTAGCTCTTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGATCTTCACCTAGATCCTTTTAAAT
TAAAAATGAAGTTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTGTAGATAACTACGA
TACGGGAGGGCTTACCATCTGGCCCCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTGTTGCCATTGCTAC
AGGCATCGTGGTGTCACGCTCGTCGTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCATGCCATCCGTAAGATGCTTTTCTGTG
ACTGGTGAGTACTCAACCAAGTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAAACGTTCTTCGGGGCGAAAAC
TCTCAAGGATCTTACCGCTGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAAAGGGAATAAGGGCGACA
CGGAAATGTTGAATACTCATACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACATTTCCCCGAAAAGTGCCACCT
GAACGAAGCATCTGTGCTTCATTTTGTAGAACAAAAATGCAACGCGAGAGCGCTAATTTTTCAAACAAAGAATC
TGAGCTGCATTTTTACAGAACAGAAATGCAACGCGAAAGCGCTATTTTACCAACGAAGAATCTGTGCTTCATTTT
TGTAAAACAAAAATGCAACGCGAGAGCGCTAATTTTTCAAACAAAGAATCTGAGCTGCATTTTTACAGAACAGA
AATGCAACGCGAGAGCGCTATTTTACCAACAAAGAATCTATACTTCTTTTTTGTTCTACAAAAATGCATCCCGAG
AGCGCTATTTTTCTAACAAAGCATCTTAGATTACTTTTTTTCTCCTTTGTGCGCTCTATAATGCAGTCTCTTGATAA
CTTTTTGCACTGTAGGTCCGTTAAGGTTAGAAGAAGGCTACTTTGGTGTCTATTTTCTCTTCCATAAAAAAAGCCT
GACTCCACTTCCCGCGTTTACTGATTACTAGCGAAGCTGCGGGTGCATTTTTTCAAGATAAAGGCATCCCCGATT
```

-continued

ATATTCTATACCGATGTGGATTGCGCATACTTTGTGAACAGAAAGTGATAGCGTTGATGATTCTTCATTGGTCAG

AAAATTATGAACGGTTTCTTCTATTTTGTCTCTATATACTACGTATAGGAAATGTTTACATTTTCGTATTGTTTTCG

ATTCACTCTATGAATAGTTCTTACTACAATTTTTTTGTCTAAAGAGTAATACTAGAGATAAACATAAAAAATGTAG

AGGTCGAGTTTAGATGCAAGTTCAAGGAGCGAAAGGTGGATGGGTAGGTTATATAGGGATATAGCACAGAGA

TATATAGCAAAGAGATACTTTTGAGCAATGTTTGTGGAAGCGGTATTCGCAATATTTTAGTAGCTCGTTACAGTC

CGGTGCGTTTTTGGTTTTTTGAAAGTGCGTCTTCAGAGCGCTTTTGGTTTTCAAAAGCGCTCTGAAGTTCCTATAC

TTTCTAGAGAATAGGAACTTCGGAATAGGAACTTCAAAGCGTTTCCGAAAACGAGCGCTTCCGAAAATGCAACG

CGAGCTGCGCACATACAGCTCACTGTTCACGTCGCACCTATATCTGCGTGTTGCCTGTATATATATATACATGAG

AAGAACGGCATAGTGCGTGTTTATGCTTAAATGCGTACTTATATGCGTCTATTTATGTAGGATGAAAGGTAGTCT

AGTACCTCCTGTGATATTATCCCATTCCATGCGGGGTATCGTATGCTTCCTTCAGCACTACCCTTTAGCTGTTCTAT

ATGCTGCCACTCCTCAATTGGATTAGTCTCATCCTTCAATGCTATCATTTCCTTTGATATTGGATCATATTAAGAAA

CCATTATTATCATGACATTAACCTATAAAAATAGGCGTATCACGAGGCCCTTTCGTC

Codon Optimized Herceptin HC

SEQ ID NO: 15

ACAGAAATTTCTAAAGAGAACCAAATTCACCCCAGAAACAACCGCACAAATACGACATCCATCCACCTTTCTTTT

ATCTTCTTTTTCTGATCTGATAATTAGTTTCATATACAATACGTAGAAACAGGCGCACAGCACCCAGACCTGGCTT

CTGCCCCAGTGTATAAGCAATGTAGCATAATTGGAAAAAAAAACGAAAAATACCGAAAATAAGTGGGAAGCTG

GGCCACAGGAGTGGGGCGGGATGCGACTGGTTCTGAGCGGGACCGGGTAATAAGGTTGAAAAACTTTGAATT

GATGGAATAAGAAACTTCTTTCTTTTCGCTGGCGGGAGAAGGAAAAAAAAAATTTTTTTTTCCTTCTGTTTAGT

ACTGGAACATTGAGAAGGCGTGTCAATTTTGAATAATTAGAGTGGTCAAAAAAATTTTTTTGCTTGGGATACCC

TTTTTCGATAATGTAAATTTTTTTGAATATAAAAGGAGATTGAAAAATTTTTCTAGCAGAAATGTTTTCAAGTT

TTAATTGCAAGTTTCGTTTGAGTATTCAGTTGTATTTTAGTTGATTTGTAGTTTATTTACTAGTATTCTCATAGTTC

TAACTCCAAGAGAAGTAACATTAAAGATGCGTTTTCCATCTATTTTTACTGCTGTGTTGTTTGCAGCCTCAAGTGC

TTTAGCTGAGGTACAATTAGTGGAGTCAGGTGGTGGTTTAGTGCAACCCGGTGGATCTTTGAGACTATCATGCG

CAGCGAGTGGTTTCAACATTAAGGACACATATATCCATTGGGTAAGGCAAGCTCCAGGTAAAGGTTTGGAATG

GGTGGCTAGAATTTATCCAACTAATGGTTACACTCGTTACGCTGATTCTGTTAAGGGAAGATTCACTATCTCCGC

CGATACCTCGAAGAACACGGCTTATCTTCAAATGAACTCTCTTAGAGCGGAAGACACTGCGGTTTATTATTGTTC

AAGATGGGGTGGTGATGGGTTTTACGCTATGGATTATTGGGGTCAGGGAACGCTTGTGACTGTTTCGTCAGCTT

CAACTAAGGGTCCCTCAGTATTCCCCCTAGCTCCCTCTAGTAAGTCAACGTCTGGAGGTACGGCAGCACTTGGTT

GTTTGGTGAAGGACTATTTCCCAGAACCTGTCACCGTGTCGTGGAATAGTGGTGCTCTAACCTCGGGAGTGCAC

ACATTCCCTGCCGTATTGCAATCTTCTGGTTTGTATAGTTTATCTTCAGTCGTCACCGTTCCATCCTCCTCATTAGG

CACGCAAACTTACATATGTAACGTCAACCATAAGCCATCGAACACCAAAGTAGATAAGAAAGTTGAACCGAAGT

CATGTGATAAAACCCATACTTGTCCACCATGTCCAGCGCCAGAATTATTAGGCGGTCCTTCAGTTTTTCTTTTCCC

TCCAAAGCCCAAAGATACGCTAATGATCAGTCGTACGCCAGAAGTTACGTGTGTAGTCGTTGATGTTAGTCATG

AGGACCCGGAAGTGAAATTCAACTGGTACGTGGATGGAGTCGAAGTACACAATGCTAAAACCAAACCAAGGGA

AGAACAATACAATTCTACTTACCGTGTTGTTTCTGTATTAACGGTTTTACATCAGGACTGGTTAAACGGGAAAGA

ATATAAGTGCAAGGTTTCCAACAAAGCTTTACCCGCTCCTATTGAAAAGACAATCTCGAAGGCTAAAGGTCAAC

CCCGTGAACCTCAGGTTTACACGTTGCCTCCATCGCGTGAAGAAATGACAAAGAATCAGGTTTCTTTGACCTGTC

TAGTTAAGGGCTTCTATCCATCCGATATCGCTGTCGAATGGGAGTCAAATGGTCAACCTGAGAATAACTATAAG

ACAACCCCACCAGTTTTAGACTCCGATGGTTCTTTCTTTTTGTACTCTAAGTTGACTGTAGATAAGTCGAGATGGC

AACAAGGGAATGTATTTAGTTGTTCTGTCATGCATGAAGCCTTACACAATCACTATACGCAGAAGTCGTTAAGTT

-continued

TATCACCAGGCAAGTAAAGTGCTTTTAACTAAGAATTATTAGTCTTTTCTGCTTATTTTTTCATCATAGTTTAGAAC
ACTTTATATTAACGAATAGTTTATGAATCTATTTAGGTTTAAAAATTGATACAGTTTTATAAGTTACTTTTTCAAAG
ACTCGTGCTGTCTATTGCATAATGCACTGGAAGGGGAAAAAAAGGTGCACACGCGTGGCTTTTTCTTGAATTT
GCAGTTTGAAAAATAACTACATGGATGATAAGAAAACATGGAGTACAGTCACTTTGAGAACCTTCAATCAGCTG
GTAACGTCTTCGTTAATTGGATACTCAAAAAGATGGATAGCATGAATCACAAGATGGAAGGAAATGCGGGCC
ACGACCACAGTGATATGCATATGGGAGATGGAGATGATACCTGTTCGATGAATATGCTATTTTCGTGGTCATAC
AAGAATACGTGTGTCGTCTTTGAATGGTGGCATATCAAGACCCTGCCTGGACTGAT

Codon Optimized Herceptin LC                                                    SEQ ID NO: 16

ACAGAAATTTCTAAAGAGAACCAAATTCACCCCAGAAACAACCGCACAAATACGACATCCATCCACCTTTCTTTT
ATCTTCTTTTTCTGATCTGATAATTAGTTTCATATACAATACGTAGAAACAGGCGCACAGCACCCAGACCTGGCTT
CTGCCCCAGTGTATAAGCAATGTAGCATAATTGGAAAAAAAACGAAAAATACCGAAAATAAGTGGGAAGCTG
GGCCACAGGAGTGGGGCGGGATGCGACTGGTTCTGAGCGGGACCGGGTAATAAGGTTGAAAAACTTTGAATT
GATGGAATAAGAAACTTCTTTCTTTTCGCTGGCGGGAGAAGGAAAAAAAAAATTTTTTTTTCCTTCTGTTTAGT
ACTGGAACATTGAGAAGGCGTGTCAATTTTGAATAATTAGAGTGGTCAAAAAAATTTTTTTTGCTTGGGATACCC
TTTTTCGATAATGTAAATTTTTTTTGAATATAAAAGGAGATTGAAAAATTTTTTCTAGCAGAAATGTTTTCAAGTT
TTAATTGCAAGTTTCGTTTGAGTATTCAGTTGTATTTTAGTTGATTTGTAGTTTATTTACTAGTATTCTCATAGTTC
TAACTCCAAGAGAAGTAACATTAAAGATGCGTTTTCCATCTATTTTCACTGCTGTATTGTTTGCTGCATCCTCTGC
ATTGGCCGACATACAAATGACCCAAAGTCCATCTTCCTTATCCGCTTCTGTAGGTGATCGTGTAACTATAACTTGT
AGAGCTTCACAAGATGTTAATACTGCTGTGGCTTGGTATCAACAAAAACCAGGCAAGGCACCTAAATTACTAAT
CTATTCTGCCTCTTTTTTGTACTCAGGCGTCCCTAGTAGATTCAGTGGTTCAAGGTCCGGAACTGATTTTACATTG
ACAATCAGTTCCCTACAACCGGAAGACTTCGCCACATACTATTGCCAGCAACACTACACCACCCCACCGACCTTT
GGTCAAGGTACAAAAGTCGAAATTAAACGTACTGTGGCCGCCCCTTCGGTATTTATTTTCCCGCCTTCAGATGAG
CAATTGAAGTCTGGCACAGCATCAGTAGTGTGTTTGCTTAATAACTTCTATCCAAGAGAGGCAAAGGTTCAGTG
GAAAGTTGATAACGCTCTACAATCGGGTAACTCTCAAGAATCTGTTACCGAACAAGACTCTAAGGATTCAACTTA
TTCGTTAAGTAGTACGTTGACATTGTCCAAAGCTGACTACGAGAAGCACAAAGTCTACGCCTGTGAAGTTACTCA
TCAAGGTCTATCTTCGCCTGTAACGAAGAGTTTCAATAGAGGTGAATGTTGAGAGTATGCTTCTCTTTTTTTTGT
AGGCCAGTGATAGGAAAGAACAATAGAATATAAATACGTCAGAATATAATAGATATGTTTTATATTTAGACCT
CGTACATAGGAATAATTGACGTTTTTTTTGGCCAACATTTGAAATTTTTTTTGTTACCTCGCGCTGAGCCCAAA
CGGGCTCCACTACCCG

Codon Optimized Rituxan HC                                                       SEQ ID NO: 17

ACAGAAATTTCTAAAGAGAACCAAATTCACCCCAGAAACAACCGCACAAATACGACATCCATCCACCTTTCTTTT
ATCTTCTTTTTCTGATCTGATAATTAGTTTCATATACAATACGTAGAAACAGGCGCACAGCACCCAGACCTGGCTT
CTGCCCCAGTGTATAAGCAATGTAGCATAATTGGAAAAAAAACGAAAAATACCGAAAATAAGTGGGAAGCTG
GGCCACAGGAGTGGGGCGGGATGCGACTGGTTCTGAGCGGGACCGGGTAATAAGGTTGAAAAACTTTGAATT
GATGGAATAAGAAACTTCTTTCTTTTCGCTGGCGGGAGAAGGAAAAAAAAAATTTTTTTTTCCTTCTGTTTAGT
ACTGGAACATTGAGAAGGCGTGTCAATTTTGAATAATTAGAGTGGTCAAAAAAATTTTTTTTGCTTGGGATACCC
TTTTTCGATAATGTAAATTTTTTTTGAATATAAAAGGAGATTGAAAAATTTTTTCTAGCAGAAATGTTTTCAAGTT
TTAATTGCAAGTTTCGTTTGAGTATTCAGTTGTATTTTAGTTGATTTGTAGTTTATTTACTAGTATTCTCATAGTTC
TAACTCCAAGAGAAGTAACATTAAAGATGCGTTTTCCATCTATTTTTACTGCTGTCCTTTTTGCCGCGTCATCAGC

-continued

TTTAGCCCAAGTTCAATTACAACAACCAGGTGCCGAGCTTGTCAAACCAGGCGCTTCTGTCAAAATGTCATGTAA
GGCGTCAGGTTACACTTTTACCTCATATAACATGCATTGGGTGAAACAGACTCCAGGTAGAGGTTTAGAGTGGA
TTGGAGCAATCTATCCAGGTAACGGAGACACTTCCTATAACCAAAAGTTTAAGGGGAAGGCAACTTTGACTGCA
GATAAATCCTCGTCTACCGCATACATGCAATTGTCTTCGCTTACATCAGAAGACTCAGCAGTTTACTATTGTGCTC
GTAGTACTTACTATGGAGGGGACTGGTATTTCAATGTGTGGGGTGCTGGCACCACTGTGACAGTTTCAGCAGCG
TCAACAAAGGGCCCATCTGTTTTCCCCCTAGCTCCCTCATCTAAGTCCACAAGTGGAGGTACGGCAGCATTGGGT
TGCTTAGTAAAAGATTACTTCCCTGAACCAGTGACTGTTTCATGGAACTCTGGTGCTTTGACTTCAGGTGTACAC
ACCTTTCCAGCCGTCTTGCAATCCTCAGGTCTTTACTCTTTATCTTCTGTTGTCACTGTGCCATCTTCTTCTTTGGGT
ACTCAAACATACATTTGTAACGTCAACCACAAACCCTCCAACACCAAGGTTGATAAGAAGGCCGAACCTAAGAG
TTGCGACAAAACACACACCTGTCCTCCCTGCCCAGCCCCAGAACTTCTTGGCGGTCCCAGTGTCTTTTTATTTCCA
CCGAAGCCAAAGGATACTCTAATGATTTCTCGTACTCCCGAAGTAACATGCGTCGTAGTAGATGTTTCACACGAA
GATCCAGAGGTTAAATTCAACTGGTACGTAGATGGTGTGGAAGTACATAACGCAAAAACCAAACCGCGTGAAG
AACAGTATAACTCTACCTACAGAGTTGTGAGTGTACTAACAGTTTTACATCAAGATTGGCTTAATGGGAAGGAA
TACAAGTGTAAAGTCTCTAACAAAGCCTTACCTGCCCCTATTGAGAAGACAATCTCAAAGGCTAAAGGTCAACCC
CGTGAACCTCAGGTTTACACATTGCCTCCTTCACGTGACGAACTTACGAAGAACCAAGTTAGTTTGACATGCTTG
GTTAAAGGCTTCTACCCATCGGATATAGCTGTGGAGTGGGAATCAAATGGACAACCTGAGAACAACTACAAGA
CAACACCACCGGTTTTGGATTCTGACGGCTCATTCTTCTTGTACTCTAAATTGACAGTCGATAAGTCTCGTTGGCA
ACAGGGTAACGTTTTCTCATGTTCCGTGATGCATGAGGCCTTACATAACCACTACACCCAAAAGTCTTTAAGTTT

GTCACCCGGTAAGTAAAGTGCTTTTAACTAAGAATTATTAGTCTTTTCTGCTTATTTTTTCATCATAGTTTAGAACA

CTTTATATTAACGAATAGTTTATGAATCTATTTAGGTTTAAAAATTGATACAGTTTTATAAGTTACTTTTTCAAAGA

CTCGTGCTGTCTATTGCATAATGCACTGGAAGGGGAAAAAAAAGGTGCACACGCGTGGCTTTTTCTTGAATTTG

CAGTTTGAAAAATAACTACATGGATGATAAGAAAACATGGAGTACAGTCACTTTGAGAACCTTCAATCAGCTGG
TAACGTCTTCGTTAATTGGATACTCAAAAAAGATGGATAGCATGAATCACAAGATGGAAGGAAATGCGGGCCA
CGACCACAGTGATATGCATATGGGAGATGGAGATGATACCTGTTCGATGAATATGCTATTTTCGTGGTCATACA
AGAATACGTGTGTCGTCTTTGAATGGTGGCATATCAAGACCCTGCCTGGACTGAT

Codon Optimized Rituxan LC

SEQ ID NO: 18

ACAGAAATTTCTAAAGAGAACCAAATTCACCCCAGAAACAACCGCACAAATACGACATCCATCCACCTTTCTTTT

ATCTTCTTTTTCTGATCTGATAATTAGTTTCATATACAATACGTAGAAACAGGCGCACAGCACCCAGACCTGGCTT

CTGCCCCAGTGTATAAGCAATGTAGCATAATTGGAAAAAAAAACGAAAAATACCGAAAATAAGTGGGAAGCTG

GGCCACAGGAGTGGGGCGGGATGCGACTGGTTCTGAGCGGGACCGGGTAATAAGGTTGAAAAACTTTGAATT

GATGGAATAAGAAACTTCTTTCTTTTCGCTGGCGGGAGAAGGAAAAAAAAAATTTTTTTTTCCTTCTGTTTAGT

ACTGGAACATTGAGAAGGCGTGTCAATTTTGAATAATTAGAGTGGTCAAAAAAATTTTTTTGCTTGGGATACCC

TTTTTCGATAATGTAAATTTTTTTGAATATAAAAGGAGATTGAAAAATTTTTCTAGCAGAAATGTTTTCAAGTT

TTAATTGCAAGTTTCGTTTGAGTATTCAGTTGTATTTTAGTTGATTTGTAGTTTATTTACTAGTATTCTCATAGTTC

TAACTCCAAGAGAAGTAACATTAAAGATGCGTTTTCCATCTATTTTCACTGCCGTTTTATTTGCTGCGTCGTCTGC

TTTAGCCCAGATCGTGCTAAGTCAATCGCCCGCCATCCTTTCAGCATCTCCCGGTGAAAAGGTGACAATGACCTG

CAGAGCCTCTTCGTCCGTCAGTTACATACATTGGTTCCAACAAAAACCAGGTTCTTCACCAAAACCCTGGATCTA

CGCTACGTCTAATCTTGCATCTGGTGTCCCTGTTAGATTTAGTGGATCGGGTAGTGGCACGTCCTATTCCTTGAC

AATATCGCGTGTTGAAGCAGAAGATGCCGCGACATATTACTGTCAGCAATGGACATCAAACCCACCTACATTCG

GTGGTGGTACTAAGCTTGAAATAAAAAGAACCGTTGCCGCACCATCTGTTTTCATCTTTCCTCCTTCTGATGAAC

AGTTAAAGAGTGGTACAGCATCGGTTGTCTGCTTATTGAACAATTTCTATCCAAGAGAAGCTAAGGTTCAATGG

AAGGTTGATAATGCACTTCAATCTGGTAATTCTCAAGAGTCTGTTACCGAACAAGACTCTAAAGATTCCACATAC

TCATTGAGTTCGACACTAACATTATCTAAGGCCGACTACGAGAAGCATAAGGTATATGCTTGTGAAGTAACACA

TCAGGGTTTATCTAGTCCAGTCACGAAATCTTTCAACAGAGGGGAGTGTTGAGAGTATGCTTCTCTTTTTTTTGT

AGGCCAGTGATAGGAAAGAACAATAGAATATAAATACGTCAGAATATAATAGATATGTTTTTATATTTAGACCT

CGTACATAGGAATAATTGACGTTTTTTTTTGGCCAACATTTGAAATTTTTTTTGTTACCTCGCGCTGAGCCCAAA

CGGGCTCCACTACCCG

```

What is claimed:

1. A method for modifying a target site in a *Kluyveromyces* host cell genome, the method comprising:
   (a) contacting a *Kluyveromyces* host cell, which has a reduced non-homologous end joining (NHEJ) activity, wherein the NHEJ activity is reduced by integrating a nucleic acid at YKU70 or YKU80, with:
      (i) a nuclease capable of cleaving the target site; and
      (ii) a donor DNA molecule comprising a nucleic acid sequence encoding a polypeptide, wherein the donor DNA molecule is capable of homologous recombination at the cleaved target site, whereby homologous recombination in the host cell results in integration of the donor linear nucleic acid at the target site;
   (b) contacting the host cell with a linear nucleic acid capable of homologous recombination with itself or with one or more additional linear nucleic acids contacted with the host cell, whereby homologous recombination in the host cell converts the linear nucleic acid or the linear nucleic acid and the one or more additional linear nucleic acids into a circular extrachromosomal nucleic acid comprising a coding sequence for a selectable marker; and
  (c) selecting a transformed host cell in which the donor DNA molecule is integrated into the target site wherein the host cell secretes the polypeptide encoded by the nucleic acid sequence.

2. The method of claim 1, wherein the circular extrachromosomal nucleic acid further comprises a stability element derived from *K. marxianus*.

3. The method of claim 1, wherein the circular extrachromosomal nucleic acid further comprises a coding sequence for a guide RNA capable of guiding the nuclease to the target site.

4. The method of claim 1, wherein the nuclease is an RNA-guided DNA endonuclease and the method further comprises introducing into the host cell, during or after step (a), a guide RNA capable of guiding the RNA-guided DNA endonuclease to the target site, wherein the guide RNA is encoded on a plasmid comprising a stability element derived from *K. marxianus*.

5. The method of claim 1, wherein the nuclease is an RNA-guided DNA endonuclease and the method further comprises, during or after step (a), contacting the host cell with:
  (i) a linear nucleic acid comprising
    (1) a nucleic acid sequence encoding a guide RNA capable of guiding the RNA-guided DNA endonuclease to the target site; or
    (2) the guide RNA.

\* \* \* \* \*

                          SEQUENCE LISTING

<160> NUMBER OF SEQ ID NOS: 22

<210> SEQ ID NO 1
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ggatccgatc tcctttcatt tctgataaaa gtaaggcttc tctatttacc ttttaaccta      60
catattcata gttggaagtt atccttctaa gtacgtatac aatattaatt caacgtaaaa     120
acaaaactta ctgtaaatat gtgtaaaaaa aatctattaa attcatggca gtttcaagaa     180
aagaaaacta ttatggtctg gtcacgtgta tacaaattat taattttaaa actatataat     240
ttattatttt tttatttttga agtttagagt aatttagta gtatttata ttttaaataa      300 atatgcttta aattttttact taatatttta ttattttaa atacaacgtt tttatttaaa    360
acaaaattat aagttaaaaa gttgttccga agtaaaata tattttatgg gttttacaaa     420
aataaattat ttttaatgta ttttttttaat tatattttttg tatgtaatta tatccacagg   480
tattatgttg aatttagctg ttttagttta cctgtgtggt actatgattt ttttagaact     540
ctcctcttag aaataggtgg tgttgcggtt gactttaac gatatatcat tttcaattta      600 tttatttttaa agtgacatag agagattcct tttaattttt taattttatt ttcaataat    660 tttaaaaatg ggggactttt aaattggaac aaaatgaaaa atatctgtta tacgtgcaac    720
tgaattttac tgaccttaaa ggactatctc gaacttggtt cggaaatcct tgaaatgatt    780
gatattttgg tggattttct ctgatttca acaagtagt attttattta atatttatta      840 tatttttac atttttttat attttttttat tgtttggaag gtaaagcaac aattactttc   900
aaaatatata atcaaactg aaatacttaa taagagacaa ataacattca agaatcaaat    960
actgggttat taatcaaaag atctctctac atgcgcccaa attcactatt taaatttact  1020
ataccactga cagaatatat gaacccagat taagtagcca gaggctcttc cactatattg  1080
agtatatagc cttacatatt ttctgcgcat aatttactga tgtaaaataa acaaaaatag  1140
ttagtttgta gttatgaaaa aaggcttttg gaaatgcga aatacgtgtt atttaaggtt  1200
aatcaacaaa acgcatatcc atagtggata gttggataaa acttcaattg atgcggccgc  1260

<210> SEQ ID NO 2
<211> LENGTH: 193
<212> TYPE: DNA
```

-continued

<213> ORGANISM: Artificial Sequence
<220> FEATURE:
<223> OTHER INFORMATION: Description of Artificial Sequence: Synthetic
      polynucleotide

<400> SEQUENCE: 2
tcacgtgtat acaaattatt aattttaaaa ctatataatt tattattttt ttattttgaa    60
gtttagagta atttagtag tattttatat tttaaataaa tatgctttaa atttttactt   120 aatatttat tatttttaaa tacaacgttt ttatttaaaa caaaattata agttaaaaag   180
ttgttccgaa agt                                                      193

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttttattgtt tg                                                        12

<210> SEQ ID NO 4
<211> LENGTH: 1205
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gatccaagtc tgaaggttgg tttggcacta actttactct tgttatattc agaattgtat    60
caagtttatt tggtagagtg gagccttttt ttatccgtaa cacttttcc ctgctccatt   120 ttgaaaaacg atttcaggcc atcttggcta ttccgaatga atttggaata tgtttaaatt   180
aataaaaata aaataaaata aaataaaaat taaatcaaat taaattaaat                240
taaattaaat taaattaaat taaataaaaa taaatacaac caatacaaca tggtaatatt   300
cttgcatcgt aatgaatatt aaatatcact ttattaatct catcatgttt tattgttttt   360
gtaaggactt taatatattt gaatcaatat tctttcaatt actagtactt ttttatatg   420 actaaaattg ttacacattg gactgacagt aattttaaa atttatgatt tattcttact   480
ttatatcttt aaaagtagaa atattatacg gacgctttga atacaattga caacttatct   540
tactagtgtg aatcaaccct atcgatgtag tactcttaaa atacggcctt cttgataaag   600
tgttaaattc atttgggtaa tgattttcg aaaaccacat tgaatgaacg atctaaataa   660 atataggat caaaagcatt ttaataattc agaaacaaac aaattattaa acaggagcag   720
ttgaacggta tgttagcgag ttttgtaaag ggtgagtaca tttatagctc tattgaacat   780
aataaataca tataaatagt attttttgac cctctatgaa gatggcttac cagcaactta   840
tgtcttttaa ttcacgtgac tactaaacaa aaaatatgt tatttaaaaa atatttatt    900 aaatttttaa actattatag attatttgtg aatgcattat ttttttaattt attaattaaa   960 agaattgcta tttacttaaa ataagaataa agcttttta tttttttaaa agaaaaatat  1020
attaaaaaca cttttccgaa agttaaaata attttatatt tatcggtagc tgcaatttat  1080
agacataata ttttatattt tttaaaattt attattattt tgtttgaaat aataacgtcg  1140
gtgagtgttt aaggtgaact aagactgaaa aagtacataa ttttttgttaa ttttatgata  1200

```
tgatc                                                                      1205
```

```
<210> SEQ ID NO 5
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
tcacgtgact actaaacaaa aaaatatgtt atttaaaaaa tatttattta aatttttaaa        60
ctattataga ttatttgtga atgcattatt ttttaattta ttaattaaaa gaattgctat       120
ttacttaaaa taagaataaa agcttttat tttttaaaa gaaaatata ttaaaaacac          180 ttttccgaaa gt                                                           192

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttttattgtt ttt                                                           13

<210> SEQ ID NO 7
<211> LENGTH: 2411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aacagattgg tgggtggtca acgcacaagc gatatcccaa cacagtcgga aaaactctcg        60
ttcattccaa aactgattgc ttcagatcac aactccgctg gagaagatga gtccgtcact       120
ttctttcaag atttgattaa cgttgatcgt ttgaaacgtc tcagaaatgt cactggtatg       180
tctatcgaaa tcgtgcttgg gacgcataga gaaatcccac agcaacagca gcagcagcag       240
gagtcacctg tagcagaagg tgttccggtc gcccaggata tggacatgt aaccacgaac        300 gacaatgcgg caaatacttc attggaagaa ccaagttcac ccattgacca ggtttatgga       360
tacctcctac aacagaacat gtctacgttg ccagaagtta cactttcgga agtgatatc        420 gctatgagct acccgacgga tccagtaccc tcttacagca gcaactttaa caactttgct       480
ctgcctacta ttgccgatga caaacaagaa ttagaacaga tgagattaaa ggagctagaa       540
agtgaacctc ctatctgaac acttaacgag aaatatttat atgtgtgttt ttgtttgtat       600
gtatgtatgt atgtatgcct gtgtatcatt aaatatatta gcggatcccg gagttttat        660 tatcgtgttc ttttcattat atagtgaacc taaagtgact ttcaattcca aattatggaa       720
agattcctgg cattatgcct tataataatc acttgtttac aacattccat taacaacaca       780
tgtacactca aattccattc cataaaacca aaaaaaacct tattgaattc tccagacctc       840
tctgtcggct tgactttgct tgctcaattc gcgtttggct gaagatcact ccagaaccta       900
ggacgtcatt attgaaatct gatcacgtga ttcgcatatt catatagacg tatattttc        960 gccactttc tctcttgaaa aaagttgtg ctagatgaac tttgagaaca aaacacattg        1020
```

```
aaagaaaagt ggaacattat aataattgga aagaatagta gattgggtgg ccaagtggaa   1080
gaatttagta actttagtgg ttagagcttg tttgaacgac caatccagta aactaatcaa   1140
ccattgaaca atgagtattc ctatctttgg agatcaagtt accgaagaga gagcagaaaa   1200
tgctcgtatg agtgcctttg ttggtgccat cgccgttggt gatctagtga aaactacact   1260
aggtccaaaa ggtatggata agttacttca aagtgcatcc aatagctcga gtttggttac   1320
aaacgatggt gctaccattc taaaatctat tcctttggac aaccctgctg ccaaggtgct   1380
tgttaacatc agtaaagtgc aagatgatga agttggtgac ggtacaacaa gtgttactgt   1440
tctaagtgca gaattattga gggaagctga aaaacttgtt gaacaaggca gaattcaccc   1500
acaaactatc atcgagggtt acagaattgc ttctgctgct gccctctctg cattggaaaa   1560
ggctgctgtg gacaactcca agaataaaga agaattttac aatgatttga tcagcatcgc   1620
caacacaacg ctatcttcta aaattctatc tcaagataag gctcacttct ctaagttggc   1680
taccgatgct atcttaagat taaagggctc tacgaacttg gaacacattc aaattattaa   1740
gatcattggt ggtaaattat cggattcttt cctagatgaa ggtttcattt tgccaaagag   1800
atttggtacc aaccaaccaa aacgtgttga aaatgcgaag attttgattg ccaacacttc   1860
tctagataca gacaaggtta aaatctttgg taccaaattt aaggtcgact ctacttccaa   1920
gttagctgaa ctagaaaaag ctgagcgtga aaaaatgaag agaaagatag aaaagattgc   1980
acaattcaac attaatacct ttatcaacag acaattaatc tatgactacc ctgaacagat   2040
gtttaccgac atgggtatca actccatcga acatgctgac tttgaaggtg ttgaaagatt   2100
agcacttgtc actggcggtg aggttgtttc tacatttgac aacccagaaa aatgtaagct   2160
aggtgaatgt aagttgatcg aagaagttat aattggtgag gaaatcttta ctaaatttac   2220
cgggtgcaag tctggtgaag cttgtaccat tgttctaagg ggtgccactg agcaagtctt   2280
ggatgaagca gaaagatctc tacatgatgc cctatctgtt ctttcccaaa caacaaagga   2340
gactagaacc gttcttggtg gtggttgtgc agaaatgata atgtctaaag cagttgatac   2400
tgcagctcaa a                                                        2411
```

<210> SEQ ID NO 8
<211> LENGTH: 529
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
actttcggaa agtgatatcg ctatgagcta cccgacggat ccagtaccct cttacagcag     60
caactttaac aactttgctc tgcctactat tgccgatgac aaacaagaat tagaacagat    120
gagattaaag gagctagaaa gtgaacctcc tatctgaaca cttaacgaga aatatttata    180
tgtgtgtttt tgtttgtatg tatgtatgta tgtatgcctg tgtatcatta aatatattag    240
cggatcccgg agtttttatt atcgtgttct tttcattata tagtgaacct aaagtgactt    300
tcaattccaa attatggaaa gattcctggc attatgcctt ataataatca cttgtttaca    360
acattccatt aacaacacat gtacactcaa attccattcc ataaaaccaa aaaaaacctt    420
attgaattct ccagacctct ctgtcggctt gactttgctt gctcaattcg cgtttggctg    480
aagatcactc cagaacctag gacgtcatta ttgaaatctg atcacgtga                529
```

<210> SEQ ID NO 9

| <211> LENGTH: 10
| <212> TYPE: DNA
| <213> ORGANISM: Artificial Sequence
| <220> FEATURE:
| <223> OTHER INFORMATION: Description of Artificial Sequence: Synthetic
|       oligonucleotide

<400> SEQUENCE: 9

```
aaacaacaaa                                                            10
```

| <210> SEQ ID NO 10
| <211> LENGTH: 1583
| <212> TYPE: DNA
| <213> ORGANISM: Artificial Sequence
| <220> FEATURE:
| <223> OTHER INFORMATION: Description of Artificial Sequence: Synthetic
|       polynucleotide

<400> SEQUENCE: 10

```
tcaattacaa agggtggaaa gtgatggggg gaatatcatc tgcacaattt tggctcgctt     60
tatatagtgc cgagattagt agggtctgga taaaaaagcg aaggagaata ggaagaggaa    120
gaaaattttt tttcttcctc tttgaaaggc cgggtaacaa agtctcatcg tcctccaacc    180
tagggctttc ctttccgctt ttttttttctt cttctcctcc aaacaagacc caaccataca    240
cacccacaca gacagaagaa aaagtgtaag gatgagcgtt gtgtcgtttt ttttttttt    300
tttttttttt ttggcggaga atgtgtgcac gtgcacagac acacgggaa gcggctgtgc     360
ctccgtatac ggcaactgcc acgacaaccg agggcacaga tacacgaggt tatgtcaaag    420
aggcgtgctg gcctgggggg gggaggctgc ggatgcctga tactgggcc tgatactgag      480
ccccaaggct cagtctcggt ctctgtctca agctcaagcc aattccttcc ggggaaccca    540
accacctccg gattttttcc gaaagtatcc ccgaacgtct atggattatc catgtataca    600
cagaacaggg agtgagtgag tgagtgcgaa aaacgaaaaa aaatacagta aaacataaac    660
cagagatagc agggaaaaga gccgtggtgc ggcgcactgc gcgccgccct ggggacggcg    720
cctctctcta gttcccccag aaaaaagagt cacgtgtaca cagccgcagc cgcagccgca    780
gccgcagtat ctccgtgtca catagattgg actgaactgg actagactag actagactag    840
agagtagacg agaatagacg agactagacg ctctggcgtt tcagataaca ccaacactat    900
ctatgttatc attacacaca cgatacgtaa tacgttgggg ctccagcggt caaggttggg    960
ggtgtggccc acatacgtaa cgtctcgccc tacaccatac acggcatttt tgtctgcctg   1020
ccggctttgg cttgcgcttt ggtacttggt atttttttcct ctttcttttt gtttccacct   1080
tcaacagaca tctacgcttt tacagttcaa gacattgaaa tttcaagact agaactagaa   1140
ttagaaattg gaaatgaaat tggaattata atagatatta gaaatagata gatattagaa   1200
tagagataga tattcgagta atagaaagga caaaagtcag gaagaagaaa acttagggcg   1260
agcgaagctg ccgtattaat ctattggaaa actgaaatac taggtttcag agaagaagaa   1320
caaacaaaaa gcgcaataac cagcactttta tccaagttac aagtgtgagt gagtgtatat   1380
ctgcaagcaa ggtgtgattg agtgagtgat ccgcttgtga tggattctgt cgctgatagc   1440
acccttgttt ccaaagctgt agcacagcct tcgccgcatc atgctgtgat aaagcgtgaa   1500
catgagcagg aaagagaaag acaaatagaa gccgaagcag aggcagaagc agaggcagaa   1560
gcagaagcag aaacagaaat aga                                           1583
```

| <210> SEQ ID NO 11
| <211> LENGTH: 200

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ttccgaaagt atccccgaac gtctatggat tatccatgta tacacagaac agggagtgag     60
tgagtgagtg cgaaaaacga aaaaaaatac agtaaaacat aaaccagaga tagcagggaa    120
aagagccgtg gtgcggcgca ctgcgcgccg ccctgggac ggcgcctctc tctagttccc     180
ccagaaaaaa gagtcacgtg                                                200

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaacataaa                                                            10

<210> SEQ ID NO 13
<211> LENGTH: 8090
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gacggcacgg ccacgcgttt aaaccgccgt tatagatgat ctttatgact atcacataaa     60
ttttgtaacc tttttcattg gttcaaaggt taaaccattt gatgacacga cattcgcaga   120
tatcttaagg tggggatcaa aagttaatga cactaaaaat tggttatatt ctcatggtcc   180
aaatacaaaa cccataaatg catcgactat taagtctaag gtcaaaagga caaggaaat    240 aaatagagtg aaatttcgct gtcctttaat attagacgaa agagcagact tgttgtttc    300 tgttagtgga tacacaatta tatctcatga gattcctgca tcgaaataca agcttatata   360
tgataatggt acggtcaaac aagaagcgta ctcccgtcgt gaatatcttg atgcggaaac   420
tggagaagtg gtaccaaatg acgaacttgc aaaaaccttt tcatttggag atgaaataat   480
tgagttgtct gaggaagaga actcacaaat tcaaaacata tacggaaatt atgactcatt   540
tttgaagcta ataggattta atctaccga ggaatgctta tgttttaca ataatatcga    600 cgctcgtcca acgccggcgg acctcgaatc cttacatcac acccaatccc ccacaagtga   660 tccccacac accatagctt caaatgtttt ctactccttt tttactcttc cagatttttct   720 cggactccgc gcatcgccgt accacttcaa acacccaag cacagcatac taaatttccc     780 ctcttttcttc ctctagggtg tcgttaatta cccgtactaa aggtttggaa aagaaaaaag   840
agaccgcctc gtttcttttt cttcgtcgaa aaaggcaata aaaatttta tcacgttttct   900 ttttcttgaa aatttttttt tttgatttt ttctctttcg atgacctccc attgatattt    960
aagttaataa acggtcttca atttctcaag tttcagtttc attttcttg ttctattaca   1020 acttttttta cttcttgctc attagaaaga aagcatagca aacctccgc gacctccaaa    1080 atcgaactac cttcacaatg gataagaaat actctatcgg tttggatatt ggtactaact   1140
ccgttggttg ggccgttatc actgatgaat acaaggttcc atctaagaag ttcaaagttt   1200
```

```
tgggtaacac tgatagacac tctatcaaga agaacttgat tggtgctttg ttatttgact    1260
ctggtgaaac cgctgaggct acccgtttaa aagaactgc tagacgtaga tacacccgtc     1320
gtaaaaacag aatctgttat ttgcaagaga tcttctccaa cgaaatggct aaggttgacg    1380
actctttttt ccatagatta gaagaatctt tcttagttga agaagataag aagcacgaac    1440
gtcatccaat cttcggtaac attgtcgacg aagttgctta ccatgaaaag tacccaacta    1500
tctatcactt gagaaagaaa ttggttgatt ctactgacaa agccgacttg agattgatct    1560
acttggcttt agctcatatg atcaaattcc gtggtcattt tttaattgaa ggtgatttga    1620
acccagacaa ctctgacgtt gataaattgt tcatccaatt ggttcaaacc tataaccaat    1680
tgtttgaaga aaacccaatt aacgcttctg gtgttgatgc taaggctatc ttgtctgcta    1740
gattgtctaa atctagaaga ttggaaaact taattgctca attgccaggt gaaaaaaaaa    1800
acggtttgtt cggtaatttg attgctttat ccttgggttt gaccccaaat ttcaagtcca    1860
actttgattt ggctgaagat gccaagttgc aattgtctaa ggatacttac gatgatgatt    1920
tagataactt attggctcaa attggtgatc aatacgctga tttgttttta gctgccaaga    1980
atttgtccga cgccattttg ttgtctgaca tcttgagagt caacactgaa attaccaagg    2040
cccctttgtc tgcttctatg attaagagat atgacgaaca ccaccaagac ttgaccttgt    2100
tgaaggcttt ggttagacaa caattacctg aaaagtataa ggaaattttt ttcgaccaat    2160
ctaagaacgg ttacgctggt tacattgacg gtggtgcctc tcaagaagaa ttctacaaat    2220
tcatcaaacc aatcttggaa aagatggacg gtactgaaga attgttagtt aaattgaaca    2280
gagaagactt gttgagaaaa caaagaacct tgacaacgg ttccattcct caccaaatcc     2340
acttgggtga gttacacgct atttttgagaa gacaagaaga tttctaccca ttcttaaagg    2400
acaaccgtga aaagattgaa aagattttga ccttcagaat tccatactac gtcggtcctt    2460
tggctcgtgg taactccaga ttcgcctgga tgactagaaa gtccgaagaa actattactc    2520
catggaactt cgaagaagtc gttgacaagg gtgcttctgc tcaatccttt atcgaaagaa    2580
tgaccaactt cgacaaaaac ttgccaaacg aaaaagtctt gccaaagcac tctttgttgt    2640
atgaatactt tactgtttat aatgaattga ctaaagttaa gtacgttact gaaggtatga    2700
gaaaaccagc ttttttatct ggtgaacaaa aaaagctat cgtcgatttg ttgttcaaaa     2760
ctaaccgtaa agttaccgtc aagcaattga aggaagatta cttcaagaag attgaatgtt    2820
ttgactccgt cgaaatctcc ggtgttgaag acagattcaa tgcttctttg ggtacttacc    2880
acgacttgtt gaaaattatc aaggacaagg atttcttaga taacgaagaa aacgaagaca    2940
ttttggaaga tattgtcttg actttgactt tgttcgaaga tagagaaatg attgaagaaa    3000
gattgaagac ttatgctcat ttgttcgacg ataaggtcat gaagcaatta aagagaagac    3060
gttacactgg ttggggtaga ttgtctagaa aattgattaa cggtatccgt gataaacaat    3120
ctggtaagac catcttggat ttcttaaagt ctgatggttt tgccaacaga aacttcatgc    3180
aattgatcca cgacgactct tgactttca aggaggacat tcaaaaggct caagtttctg     3240
gtcaaggtga ctcttttgcat gaacacattg ccaacttggc tggttctcca gctattaaga    3300
agggtatctt gcaaactgtt aaggttgttg atgaattagt taaggtcatg ggtagacaca    3360
agccagaaaa catcgtcatc gaaatggcta gagaaaacca aactactcaa aagggtcaaa    3420
agaattctag agaaagaatg aagagaattg aggaaggtat taaggaatta ggttcccaaa    3480
ttttgaagga acatccagtc gaaaacactc aattgcaaaa cgaaaaattg tacttgtact    3540
```

```
acttacaaaa cggtagagat atgtatgtcg accaagagtt ggacatcaac agattgtccg    3600
actacgatgt tgatcacatc gttccacaat ccttcttaaa ggacgactct atcgacaaca    3660
aggtcttaac cagatccgac aaaaacagag gtaagtctga caacgttcca tccgaagaag    3720
ttgttaaaaa gatgaagaac tactggagac aattgttgaa cgccaaattg atcactcaaa    3780
gaaagttcga taatttgacc aaggctgaaa gaggtggttt gtctgaattg ataaggctg     3840
gttttattaa aagacaattg gttgagacta gacaaatcac caagcatgtc gctcaaattt    3900
tagattccag aatgaacact aaatacgacg aaaacgataa gttaattaga gaagttaagg    3960
ttattacctt gaagtctaag ttggtttctg atttcagaaa ggacttccaa ttttacaagg    4020
tcagagaaat taacaactac catcacgctc atgatgctta cttgaacgcc gttgttggta    4080
ccgctttgat taaaaagtac ccaaagttgg aatccgaatt tgtctacggt gactacaagg    4140
tctacgatgt cagaaaaatg atcgctaagt ccgaacaaga gattggtaag gctactgcca    4200
agtacttctt ttactctaac atcatgaact ttttcaagac tgaaatcact ttagctaacg    4260
gtgaaattcg taagagacca ttgattgaaa ccaacggtga gactggtgaa atcgtttggg    4320
ataagggtcg tgatttcgct actgttagaa aggtcttatc tatgccacaa gttaacatcg    4380
tcaagaaaac cgaagttcaa actggtggtt tttctaagga atctatcttg ccaaaaagaa    4440
actctgataa attgattgct agaaagaagg attgggaccc aaagaagtac ggtggtttcg    4500
attccccaac cgtcgcttac tccgtcttgg ttgtcgctaa agttgaaaag ggtaagtcca    4560
agaaattgaa gtctgttaag gaattgttgg gtatcactat catggaaaga tcttccttcg    4620
aaaagaaccc aatcgatttt ttagaggcca agggttataa ggaagttaaa aaggacttaa    4680
ttattaagtt gccaaagtac tctttgttcg aattagaaaa cggtagaaaa agaatgttgg    4740
cctctgctgg tgagttgcaa aaaggtaacg aattggcctt gccatctaag tatgttaact    4800
ttttgtactt ggcctctcat tacgagaagt tgaagggttc cccagaagat aacgaacaaa    4860
agcaattgtt cgtcgaacaa cacaaacatt acttggatga aattatcgaa caaatctccg    4920
agttttccaa acgtgttatc ttggctgacg ccaatttgga taaggttttg tctgcttata    4980
ataagcatag agataagcca attagagaac aagccgagaa catcattcac ttgttcactt    5040
tgactaattt aggtgctcca gctgccttca atatttcga caccaccatt gatagaaaga    5100
gatacacctc cactaaggaa gtcttggatg ccaccttgat tcaccaatct atcactggtt    5160
tgtacgaaac tagaatcgat ttgtctcaat taggtggtga ttcccgtgcc gacccaaaga    5220
agaagagaaa ggtctaaaca ggccccttt cctttgtcga tatcatgtaa ttagttatgt     5280
cacgcttaca ttcacgccct ccccccacat ccgctctaac cgaaaggaa ggagttagac      5340
aacctgaagt ctaggtccct atttatttt ttatagttat gttagtatta agaacgttat      5400
ttatatttca aattttttctt ttttttctgt acaaacgcgt gtacgcatgt aacattatac    5460
tgaaaacctt gcttgagaag gttttggcat cccgcgtgc ttggccggcc gtttaatcag       5520
cgcccagaga ctagcactga atgatcaacg ggtagttcac acgatgcacg agcgcaacgc    5580
tcacaatgac agtctggaca tcaatagtca cactacagaa ggtgatctct caacttcagc    5640
agaccatagc gtgtaataaa tgcataatta ttttctcta aaaaaactc agctgaaatt         5700
ttatataagt actacatttt atatacatat tacatactga acaataagcg cgtttgacat    5760
tttaattttc gaagaccgcg aatccttaca tcacacccag tccccaata gttccccac        5820
acaccatgct tcaaaacgc actgtactcc ttttactct tccggatttt ctcggactct        5880
ccgcatcgcc gcacgagcca agccacaccc acacacctca taccatgttt ccctctcttg    5940
```

```
actctttcgt gcggctccat tacccgcatg aaactgtata aaagtaacaa aagactattt    6000
cgtttctttt tctttgtcgg aaaaggcaaa aaaaaaaatt tttatcacat ttcttttct    6060 tgaaaatttt ttttgggatt ttttctcttt cgatgacctc ccattgatat ttaagttaat    6120
aaaaggtctc ccgttttcca agttttaatt tgttcctctt gtttagtcat tcttcttctc    6180
agcattggtc aattagaaag agagcatagc aaactgatct aagttttaat taccatatga    6240
aaaagcctga actcaccgcg acgtctgtcg agaagtttct gatcgaaaag ttcgacagcg    6300
tctccgacct gatgcagctc tcggagggcg aagaatctcg tgctttcagc ttcgatgtag    6360
gagggcgtgg atatgtcctg cgggtaaata gctgcgccga tggtttctac aaagatcgtt    6420
atgtttatcg gcactttgca tcggccgcgc tcccgattcc ggaagtgctt gacattgggg    6480
aattcagcga gagcctgacc tattgcatct cccgccgtgc acagggtgtc acgttgcaag    6540
acctgcctga aaccgaactg cccgctgttc tgcagccggt cgcggaggcc atggatgcga    6600
tcgctgcggc cgatcttagc cagacgagcg gttcggccc attcggaccg caaggaatcg    6660
gtcaatacac tacatggcgt gatttcatat gcgcgattgc tgatccccat gtgtatcact    6720
ggcaaactgt gatggacgac accgtcagtg cgtccgtcgc gcaggctctc gatgagctga    6780
tgctttgggc cgaggactgc cccgaagtcc ggcacctcgt gcacgcggat ttcggctcca    6840
acaatgtcct gacggacaat ggccgcataa cagcggtcat tgactggagc gaggcgatgt    6900
tcggggattc ccaatacgag gtcgccaaca tcttcttctg gaggccgtgg ttggcttgta    6960
tggagcagca gacgcgctac ttcgagcgga ggcatccgga gcttgcagga tcgccgcggc    7020
tccgggcgta tatgctccgc attggtcttg accaactcta tcagagcttg gttgacggca    7080
atttcgatga tgcagcttgg gcgcagggtc gatgcgacgc aatcgtccga tccggagccg    7140
ggactgtcgg gcgtacacaa atcgcccgca gaagcgcggc cgtctggacc gatggctgtg    7200
tagaagtact cgccgatagt ggaaaccgac gccccagcac tcgtccgagg gcaaaggaat    7260
agggaaattg ataagacttt tctagttgca tatctttat atttaaatct tatctattag    7320 ttaattttt gtaatttatc cttatatagt ctggttattc taaaatatca tttcagtatc    7380
taaaatagtt cttttttttt ttgagttaga ttttatggg ggagagttga agtgttgaat    7440
tttcccactt tgcttcggga ttgtgggtca ttctgtcgat aactgatatc acatcatcaa    7500
tagaacctct tagatgcacg agcgcaacgc tcacaattaa tcagcgccca gagactagca    7560
ctgaatgatc aacgggtagt tcacacaggt ccgccggcgt tggacgagcg ctatcgtata    7620
ccatttatag atgaagtcag gaaactacct actttatcga gctatccaga actactagaa    7680
agtgatgatt atcaagtact cagtagagtc actgaaacgc tcgtgaattt tttcaatttg    7740
aaaaatgggg acaagccttc tgattaccac agcccagcgc ttcaaagaca cttcacggta    7800
ctcagagagt atcttctcca gattgaaagt aaggaaacta agatcaaga tgaagatgac    7860 gaaactcttc tgaaagtcaa acagattcac gaaagaattg ctgcttctgc tcaatcagat    7920
gatcctaaac agcaaagact agtaaagtat ttgaaactat ggaattcata ttacaatcgc    7980
tataataatt tggaaattga atcaaaacca aaacagaata aacggagtaa atttaatata    8040
taatatataa taatattcta tcggcggttt aaacgcgtgg ccgtgccgtc              8090
```

<210> SEQ ID NO 14  
<211> LENGTH: 7254  
<212> TYPE: DNA  
<213> ORGANISM: Artificial Sequence  
<220> FEATURE:

<223> OTHER INFORMATION: Description of Artificial Sequence: Synthetic
polynucleotide

<400> SEQUENCE: 14

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
aaatacacat catcgtccta caagttcatc aaagtgttgg acagacaact ataccagcat     240
ggatctcttg tatcggttct tttctcccgc tctctcgcaa taacaatgaa cactgggtca     300
atcatagcct acacaggtga acagagtagc gtttatacag ggtttatacg gtgattccta     360
cggcaaaaat ttttcatttc taaaaaaaaa aagaaaaatt tttctttcca acgctagaag     420
gaaaagaaaa atctaattaa attgatttgg tgattttctg agagttccct ttttcatata     480
tcgaattttg aatataaaag gagatcgaaa aaattttttct attcaatctg ttttctggtt     540
ttatttgata gttttttttgt gtattattat tatgggattag tactggttta tatgggtttt     600
tctgtataac ttcttttttat tttagtttgt ttaatcttat tttgagttac attatagttc     660
cctaactgca agagaagtaa cattaaaaat gaccactctt gacgcacgg cttaccggta     720
ccgcaccagt gtcccggggg acgccgaggc catcgaggca ctggatgggt ccttcaccac     780
cgacaccgtc ttccgcgtca ccgccaccgg ggacggcttc accctgcggg aggtgccggt     840
ggacccgccc ctgaccaagg tgttccccga cgacgaatcg gacgacgaat cggacgccgg     900
ggaggacggc gacccggact cccggacgtt cgtcgcgtac ggggacgacg gcgacctggc     960
gggcttcgtg gtcgtctcgt actccggctg gaaccgccgg ctgaccgtcg aggacatcga    1020
ggtcgccccg gagcaccggg ggcacggggt cgggcgcgcg ttgatggggc tcgcgacgga    1080
gttcgcccgc gagcggggcg ccgggcacct ctggctggag gtcaccaacg tcaacgcacc    1140
ggcgatccac gcgtaccggc ggatggggtt caccctctgc ggcctggaca ccgcctgta    1200
cgacggcacc gcctcggacg gcgagcaggc gctctacatg agcatgccct gccctgagt    1260
ttaacttgat actactagat ttttctctt catttataaa attttggtt ataattgaag    1320
ctttagaagt atgaaaaaat cctttttttt cattctttgc aaccaaaata agaagcttct    1380
tttattcatt gaatgatga atataaacct aacaaaagaa aaagactcga atatcaaaca    1440
ttaaaaaaaa ataaagagg ttatctgttt tcccatttag ttggagtttg cattttctaa    1500
tagatagaac tctcaattaa tgtggattta gtttctctgt tcgttttttt ttgttttgtt    1560
ctcactgtat ttacatttct atttagtatt tagttattca tataatctta acttgcggtg    1620
tgaaataccg cacagatgcg taaggagaaa ataccgcatc aggaaattgt aagcgttaat    1680
attttgttaa aattcgcgtt aaattttttgt taaatcagct cattttttaa ccaataggcc    1740
gaaatcggca aaatccctta taaatcaaaa gaatagaccg atagggggtt gagtgttgtt    1800
ccagtttgga acaagagtcc actattaaag aacgtggact ccaacgtcaa agggcgaaaa    1860
accgtctatc agggcgatgg cccactacgt gaaccatcac cctaatcaag tttttggg    1920
tcgaggtgcc gtaaagcact aaatcggaac cctaaaggga gccccgattt tagagcttga    1980
cggggaaagc ctctttgaaa agataatgta tgattatgct ttcactcata tttatacaga    2040
aacttgatgt tttctttcga gtatatacaa ggtgattaca tgtacgtttg aagtacaact    2100
ctagattttg tagtgccctc ttgggctagc ggtaaaggtg cgcatttttt cacccctac    2160
aatgttctgt tcaaaagatt ttggtcaaac gctgtagaag tgaaagttgg tgcgcatgtt    2220
```

```
tcggcgttcg aaacttctcc gcagtgaaag ataaatgatc gcagttccct tggcgtactc    2280
gttttagagc tagaaatagc aagttaaaat aaggctagtc cgttatcaac ttgaaaaagt    2340
ggcaccgagt cggtggtgct ttttttgttt tttatgtctc agcttttgtt cccttttagtg   2400 agggttaatt gcgcgcttgg cgtaatcatg gtcatagctg tttcctgtgt gaaattgtta    2460
tccgctcaca attccacaca acataggagc cggaagcata aagtgtaaag cctggggtgc    2520
ctaatgagtg aggtaactca cattaattgc gttgcgctca ctgcccgctt tccagtcggg    2580
aaacctgtcg tgccagggat ccgatctcct ttcatttctg ataaaagtaa ggcttctcta    2640
tttacctttt aacctacata ttcatagttg aagttatcc ttctaagtac gtatacaata     2700
ttaattcaac gtaaaaacaa aacttactgt aaatatgtgt aaaaaaaatc tattaaattc    2760
atggcagttt caagaaaaga aaactattat ggtctggtca cgtgtataca aattattaat    2820
tttaaaacta tataatttat tatttttta ttttgaagtt tagagtaatt ttagtagtat     2880
tttatatttt aaataaatat gctttaaatt tttacttaat attttattat ttttaaatac    2940
aacgttttta tttaaaacaa aattataagt taaaaagttg ttccgaaagt aaaatatatt    3000
ttatgggttt tacaaaaata aattattttt aatgtatttt tttaattata ttttgtatg    3060 taattatatc cacaggtatt atgttgaatt tagctgtttt agtttacctg tgtggtacta    3120 tgatttttt agaactctcc tcttagaaat aggtggtgtt gcggttgact tttaacgata     3180
tatcattttc aatttattta ttttaaagtg acatagagag attccttta attttttaat    3240 ttttattttc aataatttta aaaatggggg acttttaaat tggaacaaaa tgaaaaatat    3300
ctgttatacg tgcaactgaa ttttactgac cttaaaggac tatctcgaac ttggttcgga    3360
aatccttgaa atgattgata ttttggtgga ttttctctga ttttcaaaca agtagtattt    3420
tatttaatat ttattatatt ttttacattt ttttatattt ttttattgtt tggaaggtaa    3480
agcaacaatt actttcaaaa tatataaatc aaactgaaat acttaataag agacaaataa    3540
cattcaagaa tcaaatactg ggttattaat caaaagatct ctctacatgc gcccaaattc    3600
actatttaaa tttactatac cactgacaga atatatgaac ccagattaag tagccagagg    3660
ctcttccact atattgagta tatagcctta catattttct gcgcataatt tactgatgta    3720
aaataaacaa aaatagttag tttgtagtta tgaaaaaagg cttttggaaa atgcgaaata    3780
cgtgttattt aaggtaatc aacaaaacgc atatccatag tggatagttg gataaaactt     3840
caattgatgc ggccgcctgc attaatgaat cggccaacgc gcggggagag gcggtttgcg    3900
tattgggcgc tcttccgctt cctcgctcac tgactgctg cgctcggtcg ttcggctgcg     3960
gcgagcggta tcagctcact caaaggcggt aatacggtta tccacagaat cagggataa    4020 cgcaggaaag aacatgtgag caaaaggcca gcaaaaggcc aggaaccgta aaaaggccgc    4080
gttgctggcg ttttccata ggctccgccc ccctgacgag catcacaaaa atcgacgctc     4140
aagtcagagg tggcgaaacc cgacaggact ataaagatac caggcgtttc ccctggaag    4200 ctccctcgtg cgctctcctg ttccgaccct gccgcttacc ggatacctgt ccgcctttct    4260
cccttcggga agcgtggcgc tttctcatag ctcacgctgt aggtatctca gttcggtgta    4320
ggtcgttcgc tccaagctgg gctgtgtgca cgaaccccc gttcagcccg accgctgcgc     4380
cttatccggt aactatcgtc ttgagtccaa cccggtaaga cacgacttat cgccactggc    4440
agcagccact ggtaacagga ttagcagagc gaggtatgta ggcggtgcta cagagttctt    4500
gaagtggtgg cctaactacg gctacactag aaggacagta tttggtatct gcgctctgct    4560
gaagccagtt accttcggaa aaagagttgg tagctcttga tccggcaaac aaaccaccgc    4620
```

```
tggtagcggt ggttttttg tttgcaagca gcagattacg cgcagaaaaa aaggatctca    4680
agaagatcct ttgatctttt ctacggggtc tgacgctcag tggaacgaaa actcacgtta    4740
agggattttg gtcatgagat tatcaaaaag gatcttcacc tagatccttt taaattaaaa    4800
atgaagtttt aaatcaatct aaagtatata tgagtaaact tggtctgaca gttaccaatg    4860
cttaatcagt gaggcaccta tctcagcgat ctgtctattt cgttcatcca tagttgcctg    4920
actccccgtc gtgtagataa ctacgatacg ggagggctta ccatctggcc ccagtgctgc    4980
aatgataccg cgagacccac gctcaccggc tccagattta tcagcaataa accagccagc    5040
cggaagggcc gagcgcagaa gtggtcctgc aactttatcc gcctccatcc agtctattaa    5100
ttgttgccgg gaagctagag taagtagttc gccagttaat agtttgcgca acgttgttgc    5160
cattgctaca ggcatcgtgg tgtcacgctc gtcgtttggt atggcttcat tcagctccgg    5220
ttcccaacga tcaaggcgag ttacatgatc ccccatgttg tgcaaaaaag cggttagctc    5280
cttcggtcct ccgatcgttg tcagaagtaa gttggccgca gtgttatcac tcatggttat    5340
ggcagcactg cataattctc ttactgtcat gccatccgta agatgctttt ctgtgactgg    5400
tgagtactca accaagtcat tctgagaata gtgtatgcgg cgaccgagtt gctcttgccc    5460
ggcgtcaata cgggataata ccgcgccaca tagcagaact ttaaaagtgc tcatcattgg    5520
aaaacgttct cggggcgaaa actctcaag gatcttaccg ctgttgagat ccagttcgat    5580
gtaacccact cgtgcaccca actgatcttc agcatctttt actttcacca gcgtttctgg    5640
gtgagcaaaa acaggaaggc aaaatgccgc aaaaaaggga ataagggcga cacggaaatg    5700
ttgaatactc atactcttcc ttttcaata ttattgaagc atttatcagg gttattgtct    5760
catgagcgga tacatatttg aatgtattta gaaaaataaa caataggggt tccgcgcac    5820
atttccccga aaagtgccac ctgaacgaag catctgtgct tcattttgta gaacaaaat    5880
gcaacgcgag agcgctaatt tttcaaacaa agaatctgag ctgcattttt acagaacaga    5940
aatgcaacgc gaaagcgcta ttttaccaac gaagaatctg tgcttcattt ttgtaaaaca    6000
aaaatgcaac gcgagagcgc taattttttca aacaaagaat ctgagctgca tttttacaga    6060
acagaaatgc aacgcgagag cgctatttta ccaacaaaga atctatactt ctttttgtt    6120
ctacaaaat gcatcccgag agcgctattt ttctaacaaa gcatcttaga ttactttttt    6180
tctcctttgt gcgctctata atgcagtctc ttgataactt tttgcactgt aggtccgtta    6240
aggttagaag aaggctactt tggtgtctat tttctcttcc ataaaaaag cctgactcca    6300
cttcccgcgt ttactgatta ctagcgaagc tgcgggtgca ttttttcaag ataaaggcat    6360
ccccgattat attctatacc gatgtggatt gcgcatactt tgtgaacaga aagtgatagc    6420
gttgatgatt cttcattggt cagaaaatta tgaacggttt cttctatttt gtctctatat    6480
actacgtata ggaaatgttt acattttcgt attgttttcg attcactcta tgaatagttc    6540
ttactacaat tttttttgtct aaagagtaat actagagata aacataaaaa atgtagaggt    6600
cgagtttaga tgcaagttca aggagcgaaa ggtggatggg taggttatat agggatatag    6660
cacagagata tatagcaaag agatactttt gagcaatgtt tgtggaagcg gtattcgcaa    6720
tattttagta gctcgttaca gtccggtgcg ttttggttt tttgaaagtg cgtcttcaga    6780
gcgcttttgg ttttcaaaag cgctctgaag ttcctatact ttctagagaa taggaacttc    6840
ggaataggaa cttcaaagcg tttccgaaaa cgagcgcttc cgaaaatgca acgcgagctg    6900
cgcacataca gctcactgtt cacgtcgcac ctatatctgc gtgttgcctg tatatatata    6960
```

```
tacatgagaa gaacggcata gtgcgtgttt atgcttaaat gcgtacttat atgcgtctat    7020
ttatgtagga tgaaaggtag tctagtacct cctgtgatat tatcccattc catgcggggt    7080
atcgtatgct tccttcagca ctacccttta gctgttctat atgctgccac tcctcaattg    7140
gattagtctc atccttcaat gctatcattt cctttgatat tggatcatat taagaaacca    7200
ttattatcat gacattaacc tataaaaata ggcgtatcac gaggcccttt cgtc           7254

<210> SEQ ID NO 15
<211> LENGTH: 2523
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
acagaaattt ctaaagagaa ccaaattcac cccagaaaca accgcacaaa tacgacatcc      60
atccaccttt cttttatctt cttttttctga tctgataatt agtttcatat acaatacgta    120
gaaacaggcg cacagcaccc agacctggct tctgccccag tgtataagca atgtagcata    180
attggaaaaa aaaacgaaaa ataccgaaaa taagtgggaa gctgggccac aggagtgggg    240
cgggatgcga ctggttctga gcgggaccgg gtaataaggt tgaaaaactt tgaattgatg    300
gaataagaaa cttctttctt ttcgctggcg ggagaaggaa aaaaaaaatt tttttttcc    360 ttctgtttag tactggaaca ttgagaaggc gtgtcaattt gaataatta gagtggtcaa    420 aaaaattttt tttgcttggg ataccctttt tcgataatgt aaattttttt tgaatataaa    480
aggagattga aaaattttt ctagcagaaa tgttttcaag ttttaattgc aagtttcgtt    540
tgagtattca gttgtatttt agttgatttg tagtttattt actagtattc tcatagttct    600
aactccaaga gaagtaacat taaagatgcg ttttccatct atttttactg ctgtgttgtt    660
tgcagcctca agtgctttag ctgaggtaca attagtggag tcaggtggtg gtttagtgca    720
acccggtgga tctttgagac tatcatgcgc agcgagtggt ttcaacatta aggacacata    780
tatccattgg gtaaggcaag ctccaggtaa aggtttggaa tgggtggcta gaatttatcc    840
aactaatggt tacactcgtt acgctgattc tgttaaggga agattcacta tctccgccga    900
tacctcgaag aacacggctt atcttcaaat gaactctctt agagcggaag acactgcggt    960
ttattattgt tcaagatggg gtggtgatgg gttttacgct atggattatt ggggtcaggg   1020
aacgcttgtg actgtttcgt cagcttcaac taagggtccc tcagtattcc ccctagctcc   1080
ctctagtaag tcaacgtctg gaggtacggc agcacttggt tgtttggtga aggactattt   1140
cccagaacct gtcaccgtgt cgtggaatag tggtgctcta acctcgggag tgcacacatt   1200
ccctgccgta ttgcaatctt ctggtttgta tagtttatct tcagtcgtca ccgttccatc   1260
ctcctcatta ggcacgcaaa cttacatatg taacgtcaac cataagccat cgaacaccaa   1320
agtagataag aaagttgaac cgaagtcatg tgataaaacc catacttgtc caccatgtcc   1380
agcgccagaa ttattaggcg gtccttcagt tttctttttc cctccaaagc ccaaagatac   1440
gctaatgatc agtcgtacgc cagaagttac gtgtgtagtc gttgatgtta gtcatgagga   1500
cccggaagtg aaattcaact ggtacgtgga tggagtcgaa gtacacaatg ctaaaaccaa   1560
accaagggaa gaacaataca attctactta ccgtgttgtt tctgtattaa cggttttaca   1620
tcaggactgg ttaaacggga agaatataa gtgcaaggtt tccaacaaag ctttacccgc   1680
tcctattgaa aagacaatct cgaaggctaa aggtcaaccc cgtgaacctc aggtttacac   1740
```

| | | | | |
|---|---|---|---|---|
| gttgcctcca | tcgcgtgaag | aaatgacaaa | gaatcaggtt | tctttgacct gtctagttaa | 1800 |
| gggcttctat | ccatccgata | tcgctgtcga | atgggagtca | atggtcaac ctgagaataa | 1860 |
| ctataagaca | accccaccag | ttttagactc | cgatggttct | ttcttttgt actctaagtt | 1920 |
| gactgtagat | aagtcgagat | ggcaacaagg | gaatgtattt | agttgttctg tcatgcatga | 1980 |
| agccttacac | aatcactata | cgcagaagtc | gttaagttta | tcaccaggca agtaaagtgc | 2040 |
| ttttaactaa | gaattattag | tcttttctgc | ttatttttc | atcatagttt agaacacttt | 2100 |
| atattaacga | atagtttatg | aatctattta | ggtttaaaaa | ttgatacagt tttataagtt | 2160 |
| actttttcaa | agactcgtgc | tgtctattgc | ataatgcact | ggaaggggaa aaaaaaggtg | 2220 |
| cacacgcgtg | gctttttctt | gaatttgcag | tttgaaaaat | aactacatgg atgataagaa | 2280 |
| aacatggagt | acagtcactt | tgagaacctt | caatcagctg | gtaacgtctt cgttaattgg | 2340 |
| atactcaaaa | aagatggata | gcatgaatca | caagatggaa | ggaaatgcgg ccacgacca | 2400 |
| cagtgatatg | catatgggag | atggagatga | tacctgttcg | atgaatatgc tattttcgtg | 2460 |
| gtcatacaag | aatacgtgtg | tcgtctttga | atggtggcat | atcaagaccc tgcctggact | 2520 |
| gat | | | | | 2523 |

<210> SEQ ID NO 16
<211> LENGTH: 1517
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

| | | | | |
|---|---|---|---|---|
| acagaaattt | ctaaagagaa | ccaaattcac | cccagaaaca | accgcacaaa tacgacatcc | 60 |
| atccaccttt | cttttatctt | cttttttctga | tctgataatt | agtttcatat acaatacgta | 120 |
| gaaacaggcg | cacagcaccc | agacctggct | tctgccccag | tgtataagca atgtagcata | 180 |
| attggaaaaa | aaaacgaaaa | ataccgaaaa | taagtgggaa | gctgggccac aggagtgggg | 240 |
| cgggatgcga | ctggttctga | gcgggaccgg | gtaataaggt | tgaaaaactt tgaattgatg | 300 |
| gaataagaaa | cttcttcttc | ttcgctggcg | ggagaaggaa | aaaaaaaatt ttttttttcc | 360 |
| ttctgtttag | tactggaaca | ttgagaaggc | gtgtcaattt | tgaataatta gagtggtcaa | 420 |
| aaaaattttt | tttgcttggg | ataccctttt | tcgataatgt | aaattttttt tgaatataaa | 480 |
| aggagattga | aaatttttt | ctagcagaaa | tgttttcaag | ttttaattgc aagtttcgtt | 540 |
| tgagtattca | gttgtatttt | agttgatttg | tagtttattt | actagtattc tcatagttct | 600 |
| aactccaaga | gaagtaacat | taaagatgcg | ttttccatct | attttcactg ctgtattgtt | 660 |
| tgctgcatcc | tctgcattgg | ccgacataca | aatgacccaa | agtccatctt ccttatccgc | 720 |
| ttctgtaggt | gatcgtgtaa | ctataacttg | tagagcttca | caagatgtta atactgctgt | 780 |
| ggcttggtat | caacaaaaac | caggcaaggc | acctaaatta | ctaatctatt ctgcctcttt | 840 |
| tttgtactca | ggcgtcccta | gtagattcag | tggttcaagg | tccggaactg attttacatt | 900 |
| gacaatcagt | tccctacaac | cggaagactt | cgccacatac | tattgccagc aacactacac | 960 |
| caccccaccg | acctttggtc | aaggtacaaa | agtcgaaatt | aaacgtactg tggccgcccc | 1020 |
| ttcggtattt | attttcccgc | cttcagatga | gcaattgaag | tctggcacag catcagtagt | 1080 |
| gtgtttgctt | aataacttct | atccaagaga | ggcaaaggtt | cagtgaaag ttgataacgc | 1140 |
| tctacaatcg | ggtaactctc | aagaatctgt | taccgaacaa | gactctaagg attcaactta | 1200 |

```
ttcgttaagt agtacgttga cattgtccaa agctgactac gagaagcaca aagtctacgc    1260
ctgtgaagtt actcatcaag gtctatcttc gcctgtaacg aagagtttca atagaggtga    1320
atgttgagag tatgcttctc ttttttttg  taggccagtg ataggaaaga acaatagaat    1380
ataaatacgt cagaatataa tagatatgtt tttatattta gacctcgtac ataggaataa    1440
ttgacgtttt tttttggcca acatttgaaa ttttttttg  ttacctcgcg ctgagcccaa    1500
acgggctcca ctacccg                                                   1517
```

<210> SEQ ID NO 17
<211> LENGTH: 2526
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
acagaaattt ctaaagagaa ccaaattcac cccagaaaca accgcacaaa tacgacatcc      60
atccaccttt cttttatctt cttttttctga tctgataatt agtttcatat acaatacgta    120
gaaacaggcg cacagcaccc agacctggct tctgccccag tgtataagca atgtagcata    180
attggaaaaa aaacgaaaa  ataccgaaaa taagtgggaa gctgggccac aggagtgggg    240
cgggatgcga ctggttctga gcgggaccgg gtaataaggt tgaaaaactt tgaattgatg    300
gaataagaaa cttctttctt ttcgctggcg ggagaaggaa aaaaaaatt  tttttttcc     360 ttctgtttag tactggaaca ttgagaaggc gtgtcaattt tgaataatta gagtggtcaa    420
aaaaattttt tttgcttggg ataccctttt tcgataatgt aaattttttt tgaatataaa    480
aggagattga aaaattttt  ctagcagaaa tgttttcaag ttttaattgc aagtttcgtt    540
tgagtattca gttgtatttt agttgatttg tagtttattt actagtattc tcatagttct    600
aactccaaga gaagtaacat taaagatgcg ttttccatct attttactg  ctgtcctttt    660 tgccgcgtca tcagctttag cccaagttca attacaacaa ccaggtgccg agcttgtcaa    720
accaggcgct tctgtcaaaa tgtcatgtaa ggcgtcaggt tacacttta  cctcatataa    780 catgcattgg gtgaaacaga ctccaggtag aggtttagag tggattggag caatctatcc    840
aggtaacgga gacacttcct ataaccaaaa gtttaagggg aaggcaactt gactgcaga     900 taaatcctcg tctaccgcat acatgcaatt gtcttcgctt acatcagaag actcagcagt    960
ttactattgt gctcgtagta cttactatgg aggggactgg tatttcaatg tgtggggtgc   1020
tggcaccact gtgacagttt cagcagcgtc aacaaagggc ccatctgttt tcccccctagc  1080 tccctcatct aagtccacaa gtggaggtac ggcagcattg ggttgcttag taaaagatta   1140
cttccctgaa ccagtgactg tttcatgaa  ctctggtgct ttgacttcag gtgtacacac   1200
ctttccagcc gtcttgcaat cctcaggtct ttactcttta tcttctgttg tcactgtgcc   1260
atcttcttct ttgggtactc aaacatacat tgtaacgtc  aaccacaaac cctccaacac   1320
caaggttgat aagaaggccg aacctaagag ttgcgacaaa acacacacct gtcctccctg   1380
cccagcccca gaacttcttg gcggtcccag tgtctttta  tttccaccga agccaaagga   1440
tactctaatg atttctcgta ctcccgaagt aacatgcgtc gtagtagatg tttcacacga   1500
agatccagag gttaaattca actggtacgt agatggtgtg gaagtacata acgcaaaaac   1560
caaaccgcgt gaagaacagt ataactctac ctacagagtg gtgagtgtac taacagtttt   1620
acatcaagat tggcttaatg ggaaggaata caagtgtaaa gtctctaaca aagccttacc   1680
```

```
tgccccTatt gagaagacaa tctcaaggc taaaggtcaa ccccgtgaac ctcaggttta    1740
cacattgcct ccttcacgtg acgaacttac gaagaaccaa gttagtttga catgcttggt    1800
taaaggcttc tacccatcgg atatagctgt ggagtgggaa tcaaatggac aacctgagaa    1860
caactacaag acaacaccac cggttttgga ttctgacggc tcattcttct tgtactctaa    1920
attgacagtc gataagtctc gttggcaaca gggtaacgtt ttctcatgtt ccgtgatgca    1980
tgaggcctta cataaccact acacccaaaa gtctttaagt tgtcacccg gtaagtaaag     2040 tgcttttaac taagaattat tagtcttttc tgcttatttt ttcatcatag tttagaacac    2100
tttatattaa cgaatagttt atgaatctat ttaggtttaa aaattgatac agttttataa    2160
gttacttttt caagactcg tgctgtctat tgcataatgc actggaaggg gaaaaaaaag     2220
gtgcacacgc gtggcttttt cttgaatttg cagtttgaaa ataactaca tggatgataa     2280 gaaaacatgg agtacagtca ctttgagaac cttcaatcag ctggtaacgt cttcgttaat    2340
tggatactca aaaagatgg atagcatgaa tcacaagatg gaaggaaatg cgggccacga     2400
ccacagtgat atgcatatgg gagatggaga tgatacctgt tcgatgaata tgctattttc    2460
gtggtcatac aagaatacgt gtgtcgtctt tgaatggtgg catatcaaga ccctgcctgg    2520
actgat                                                              2526
```

<210> SEQ ID NO 18
<211> LENGTH: 1514
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
acagaaattt ctaaagagaa ccaaattcac cccagaaaca accgcacaaa tacgacatcc      60
atccaccttt cttttatctt cttttttctga tctgataatt agtttcatat acaatacgta    120
gaaacaggcg cacagcaccc agacctggct tctgccccag tgtataagca atgtagcata    180
attggaaaaa aaacgaaaa ataccgaaaa taagtgggaa gctgggccac aggagtgggg     240
cgggatgcga ctggttctga gcgggaccgg gtaataaggt tgaaaaactt tgaattgatg    300
gaataagaaa cttctttctt ttcgctggcg ggagaaggaa aaaaaaatt tttttttcc     360 ttctgtttag tactggaaca ttgagaaggc gtgtcaattt tgaataatta gagtggtcaa    420 aaaaatttt tttgcttggg atacccttt tcgataatgt aaatttttt tgaatataaa      480 aggagattga aaaatttttt ctagcagaaa tgttttcaag ttttaattgc aagtttcgtt    540
tgagtattca gttgtatttt agttgatttg tagtttattt actagtattc tcatagttct    600
aactccaaga gaagtaacat taaagatgcg ttttccatct attttcactg ccgttttatt    660
tgctgcgtcg tctgctttag cccagatcgt gctaagtcaa tcgcccgcca tcctttcagc    720
atctcccggt gaaaggtga caatgacctg cagagcctct tcgtccgtca gttacataca    780
ttggttccaa caaaaaccag gttcttcacc aaaaccctgg atctacgcta cgtctaatct    840
tgcatctggt gtccctgtta gatttagtgg atcgggtagt ggcacgtcct attccttgac    900
aatatcgcgt gttgaagcag aagatgccgc gacatattac tgtcagcaat ggacatcaaa    960
cccacctaca ttcggtggtg gtactaagct tgaaataaaa agaaccgttg ccgcaccatc   1020
tgttttcatc tttcctcctt ctgatgaaca gttaaagagt ggtacagcat cggttgtctg   1080
cttattgaac aatttctatc caagagaagc taaggttcaa tggaaggttg ataatgcact   1140
```

-continued

```
tcaatctggt aattctcaag agtctgttac cgaacaagac tctaaagatt ccacatactc    1200
attgagttcg acactaacat tatctaaggc cgactacgag aagcataagg tatatgcttg    1260
tgaagtaaca catcagggtt tatctagtcc agtcacgaaa tctttcaaca gaggggagtg    1320
ttgagagtat gcttctcttt tttttgtag gccagtgata ggaaagaaca atagaatata     1380
aatacgtcag aatataatag atatgttttt atatttagac ctcgtacata ggaataattg    1440
acgttttttt ttggccaaca tttgaaattt tttttgtta cctcgcgctg agcccaaacg     1500
ggctccacta cccg                                                     1514
```

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gccgcgggca acagcccgc                                                19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatggtgccg aggcggcgg                                                19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gctacaagcg agcccggct                                                19

<210> SEQ ID NO 22
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 22

Leu Ala Gly Leu Ile Asp Ala Asp Gly
1               5
```